(12) United States Patent
Stupp et al.

(10) Patent No.: US 12,214,076 B2
(45) Date of Patent: Feb. 4, 2025

(54) DRUG DELIVERY VEHICLES FOR ATHEROSCLEROSIS NANOMEDICINE

(71) Applicants: Northwestern University, Evanston, IL (US); The University of North Carolina at Chapel Hill, Durham, NC (US)

(72) Inventors: Samuel I. Stupp, Chicago, IL (US); Melina R. Kibbe, Chapel Hill, NC (US); Mark R. Karver, Chicago, IL (US); Erica B. Peters, Durham, NC (US); Miranda So, Highland Park, NJ (US); Neel Anand Mansukhani, Chicago, IL (US); Mazen Albaghdadi, Brookline, MA (US); Nick D. Tsihlis, Durham, NC (US)

(73) Assignees: Northwestern University, Evanston, IL (US); The University of North Carolina at Chapel Hill, Durham, NC (US)

( * ) Notice: Subject to any disclaimer, the term of this patent is extended or adjusted under 35 U.S.C. 154(b) by 643 days.

(21) Appl. No.: 16/792,474

(22) Filed: Feb. 17, 2020

(65) Prior Publication Data
US 2020/0289416 A1 Sep. 17, 2020

Related U.S. Application Data

(60) Provisional application No. 62/807,092, filed on Feb. 18, 2019.

(51) Int. Cl.
| | | |
|---|---|---|
| A61K 9/127 | (2006.01) | |
| A61K 31/195 | (2006.01) | |
| A61K 38/17 | (2006.01) | |
| A61K 47/65 | (2017.01) | |
| A61P 9/10 | (2006.01) | |
| C07K 14/775 | (2006.01) | |

(52) U.S. Cl.
CPC ............ *A61K 9/127* (2013.01); *A61K 31/195* (2013.01); *A61K 38/1709* (2013.01); *A61K 47/65* (2017.08); *A61P 9/10* (2018.01); *C07K 14/775* (2013.01)

(58) Field of Classification Search
CPC .. A61K 31/195; A61K 38/1709; A61K 47/62; A61K 47/65; A61K 47/6953; A61K 9/127; A61K 9/145; A61K 9/5169; A61K 9/70; A61P 9/10; B82Y 5/00; C07K 14/775
See application file for complete search history.

(56) References Cited

U.S. PATENT DOCUMENTS

| | | | |
|---|---|---|---|
| 7,030,167 | B2 | 4/2006 | Gunther |
| 7,371,719 | B2 | 5/2008 | Stupp |
| 7,452,679 | B2 | 11/2008 | Stupp |
| 7,491,690 | B2 | 2/2009 | Stupp |
| 7,534,761 | B1 | 5/2009 | Stupp et al. |
| 7,544,661 | B2 | 6/2009 | Stupp et al. |
| 7,554,021 | B2 | 6/2009 | Stupp et al. |
| 7,683,025 | B2 | 3/2010 | Stupp et al. |
| 7,745,708 | B2 | 6/2010 | Stupp et al. |
| 7,838,491 | B2 | 11/2010 | Stupp et al. |
| 7,851,445 | B2 | 12/2010 | Stupp et al. |
| 8,063,014 | B2 | 11/2011 | Stupp et al. |
| 8,076,295 | B2 | 12/2011 | Hulvat et al. |
| 8,080,262 | B2 | 12/2011 | Lee et al. |
| 8,114,834 | B2 | 2/2012 | Hsu et al. |
| 8,114,835 | B2 | 2/2012 | Mata et al. |
| 8,124,583 | B2 | 2/2012 | Stupp et al. |
| 8,138,140 | B2 | 3/2012 | Stupp et al. |
| 8,236,800 | B2 | 8/2012 | Degrado et al. |
| 8,450,271 | B2 | 5/2013 | Shah et al. |
| 8,512,693 | B2 | 8/2013 | Capito et al. |
| 8,546,338 | B2 | 10/2013 | Donners et al. |
| 8,580,923 | B2 | 11/2013 | Stupp et al. |
| 8,748,569 | B2 | 6/2014 | Stupp et al. |
| 8,772,228 | B2 | 7/2014 | Stupp et al. |
| 9,011,914 | B2 | 4/2015 | Po et al. |
| 9,040,626 | B2 | 5/2015 | Chien et al. |
| 9,044,514 | B2 | 6/2015 | Xu et al. |
| 2017/0367989 | A1* | 12/2017 | Dhar ................. A61K 47/6927 |

OTHER PUBLICATIONS

Miranda M. So, Peptide Amphiphile Nanostructures for Targeting of Atherosclerotic Plaque and Drug Delivery, Cardiovascular Nanoscale Therapies, published Feb. 12, 2018, pp. 1-7, vol. 2.*
Eun Ji Chung, Targeting and therapeutic peptides in nanomedicine for atherosclerosis, Experimental Biology and Medicine 2016; 241: 891-898.*
Shann S. Yu, Physiologically Relevant Oxidative Degradation of Oligo(proline) Cross-Linked Polymeric Scaffolds, Biomacromolecules 2011, 12, 4357-4366.*
Zhenhua Song, Self-assembly of peptide amphiphiles for drug delivery: the role of peptide primary and secondary structures, Biomater. Sci., 2017, 5, 2369.*
Datta, et al., Effects of increasing hydrophobicity on the physical-chemical and biological properties of a class A amphipathic helical peptide. J Lipid Res. Jul. 2001;42(7):1096-104.

* cited by examiner

*Primary Examiner* — Julie Ha
*Assistant Examiner* — Erinne R Dabkowski
(74) *Attorney, Agent, or Firm* — Casimir Jones, S.C.; Rikki A. Hullinger

(57) ABSTRACT

Provided herein are peptide amphiphiles (PAs). In some embodiments, provided herein are targeting PAs comprising a PA backbone and a targeting moiety. In some embodiments, provided herein are therapeutic PAs comprising a PA backbone and a therapeutic agent. In some embodiments, the peptide amphiphiles are co-assembled into nanofibers. In some embodiments, the nanofibers may be used for the treatment of atherosclerosis or related disease.

6 Claims, 74 Drawing Sheets
(70 of 74 Drawing Sheet(s) Filed in Color)
Specification includes a Sequence Listing.

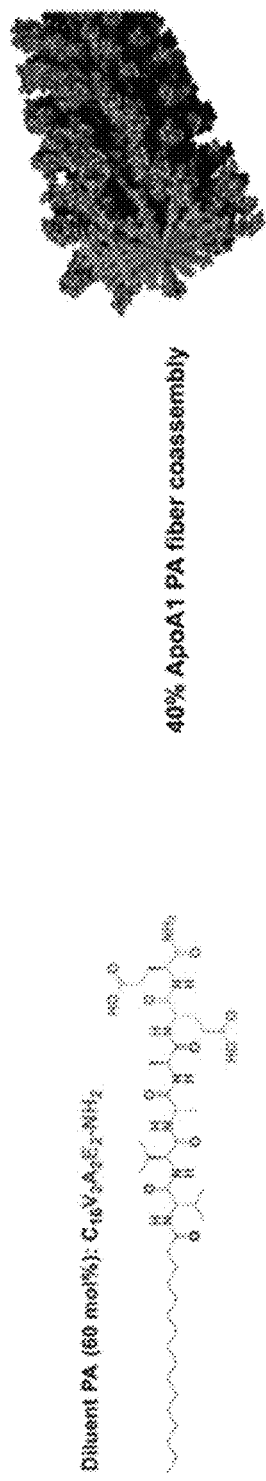
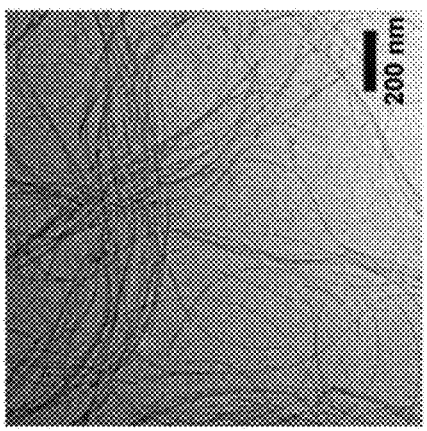
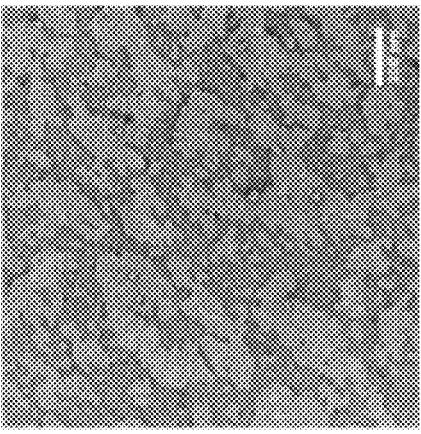
FIG. 1A
FIG. 1B
FIG. 1C

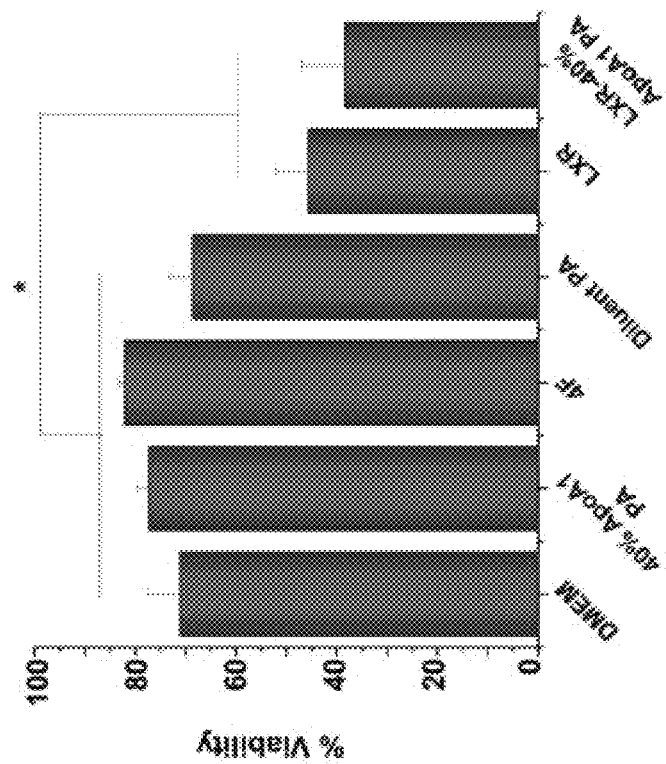
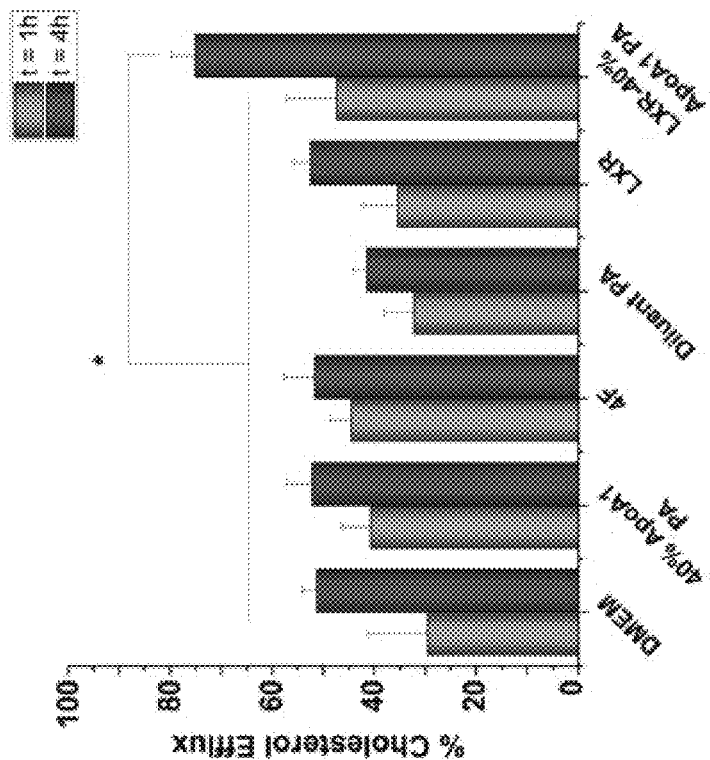
FIG. 3E
FIG. 3D

FIG. 6A
FIG. 6B
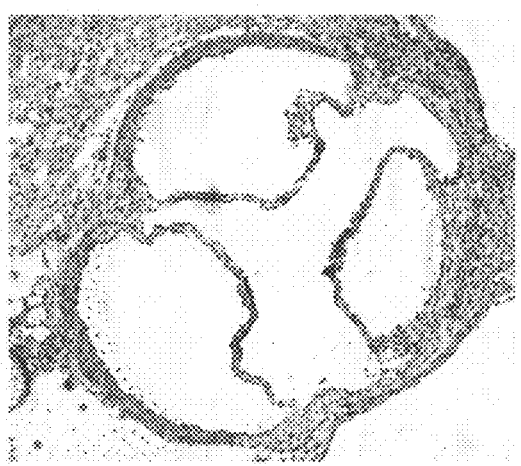
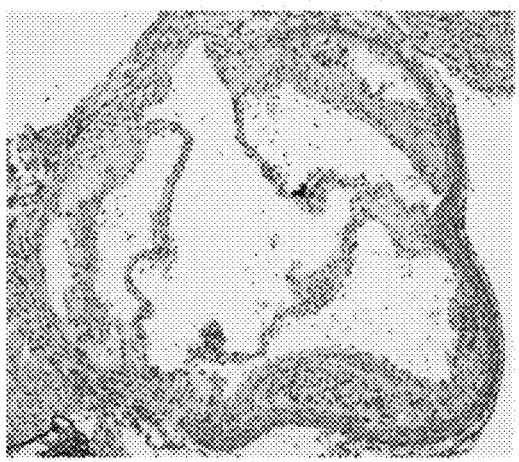
FIG. 6C
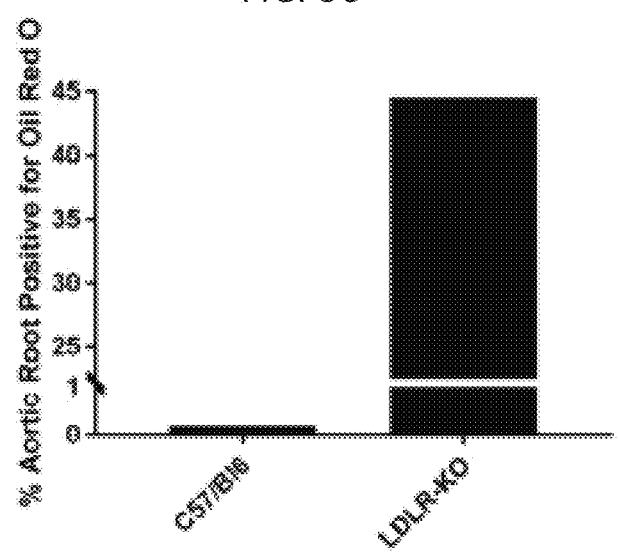

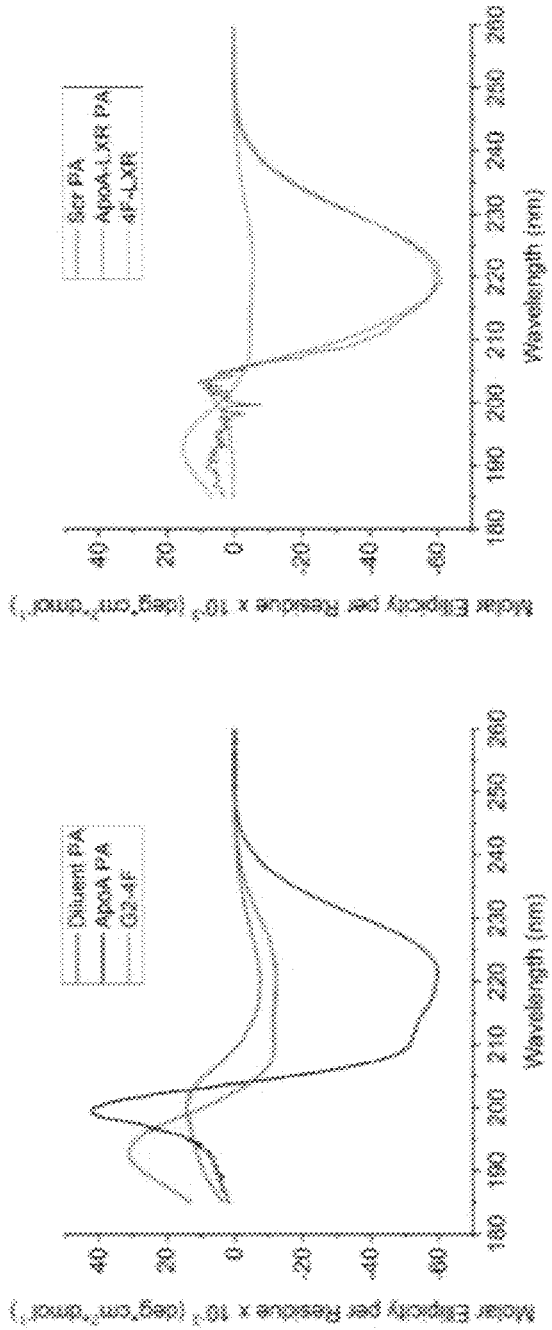
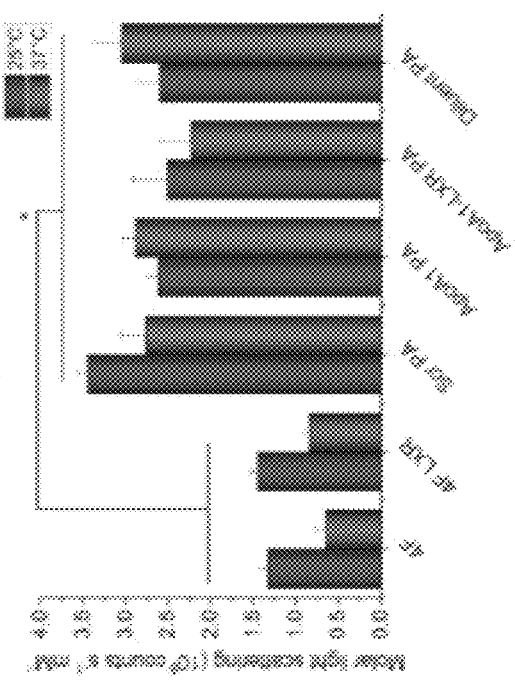
FIG. 20A
FIG. 20B
FIG. 20C

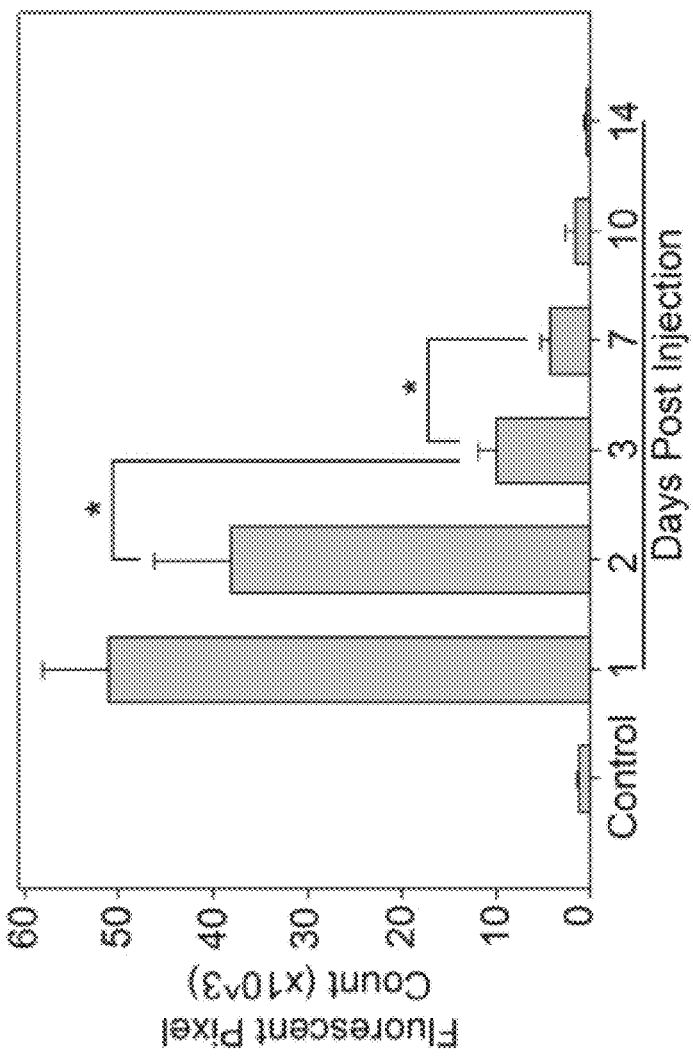
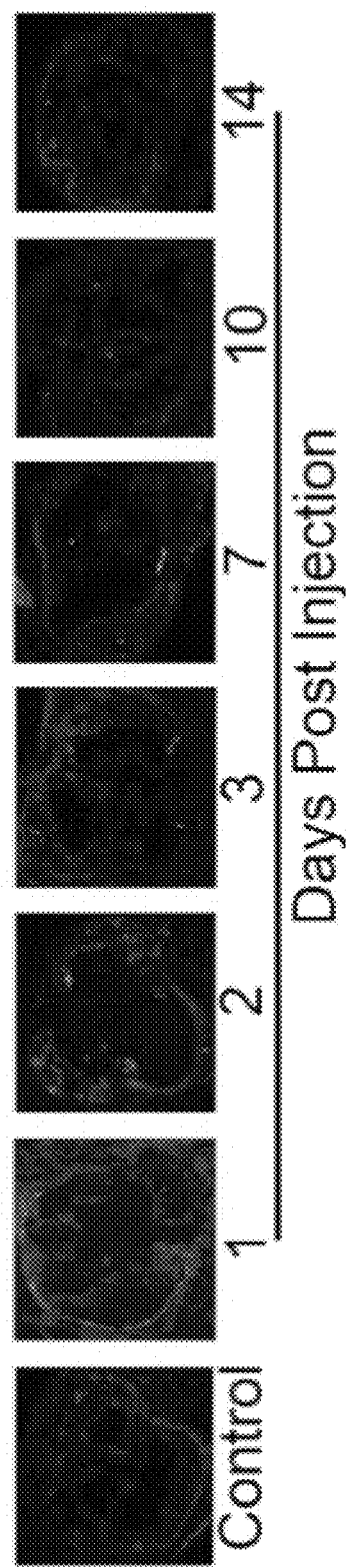

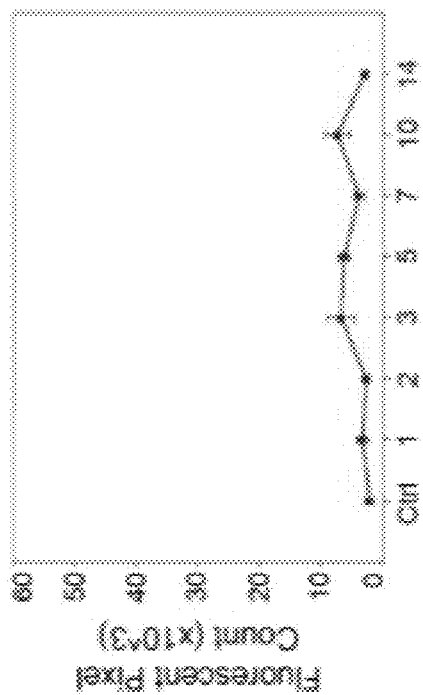
FIG. 26A
Lung
FIG. 26C
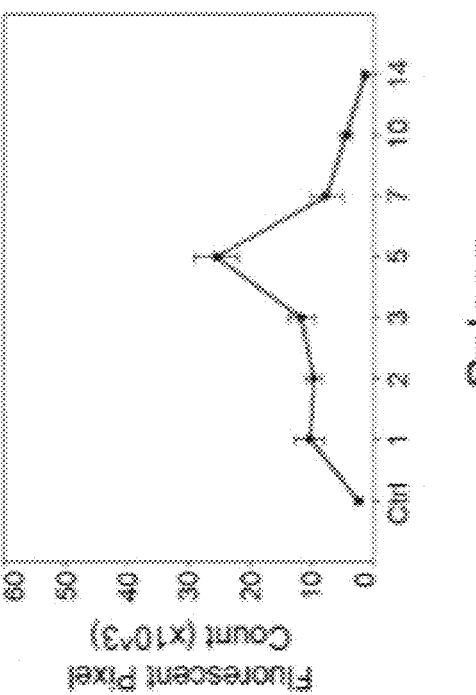
FIG. 26B
Liver
FIG. 26D
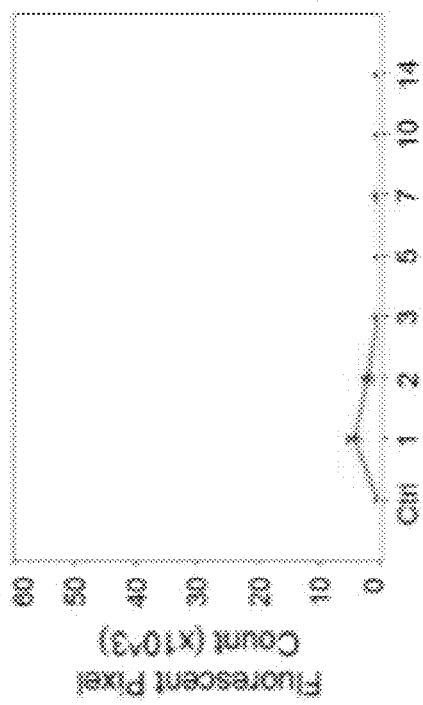
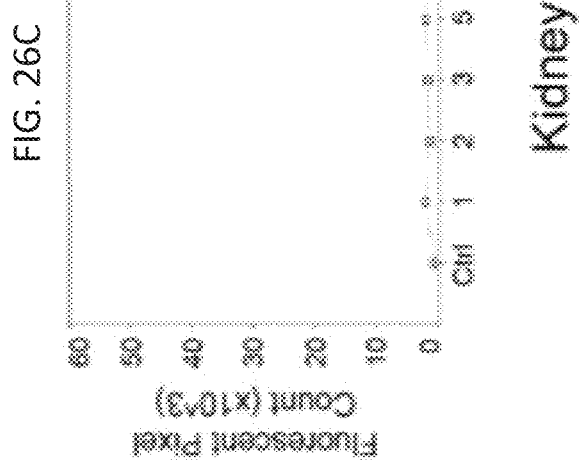
Spleen
Kidney

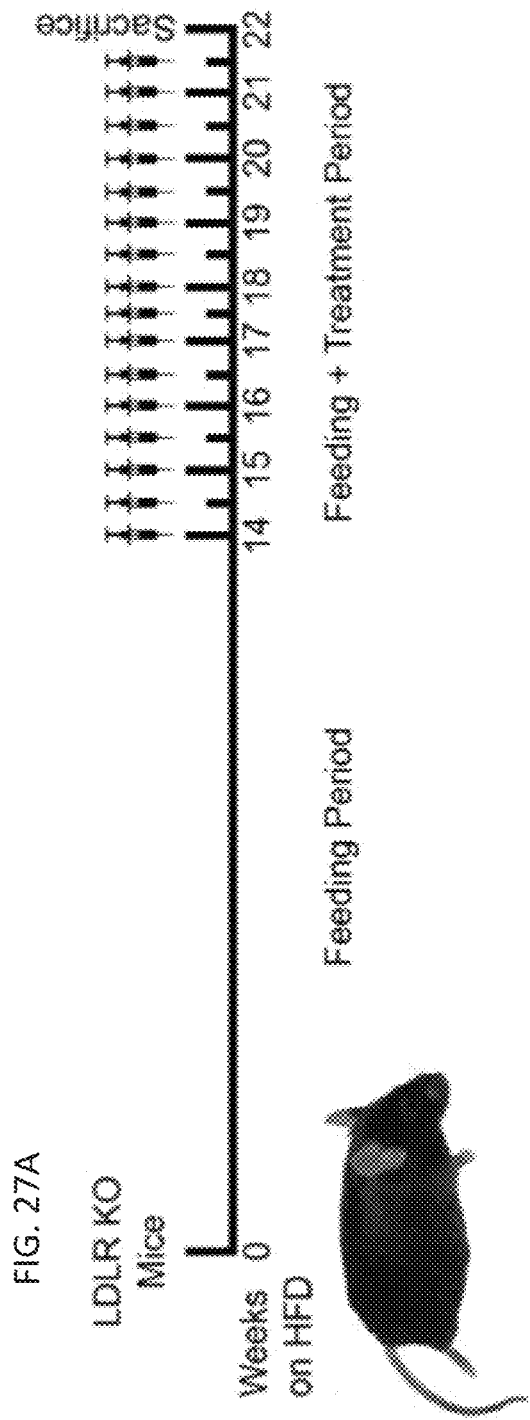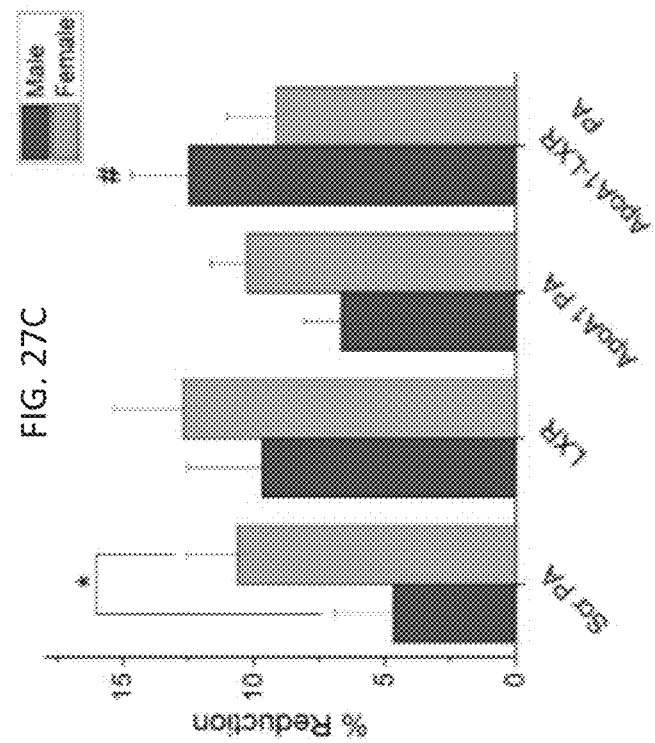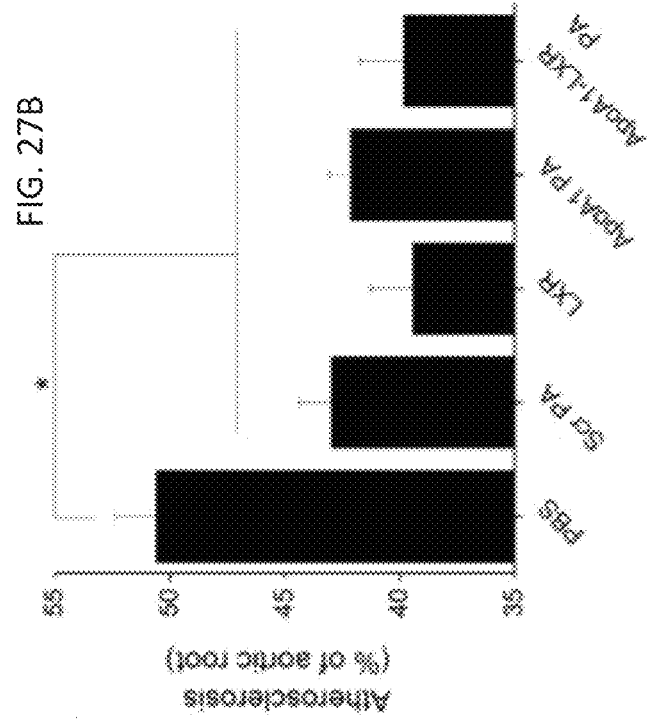

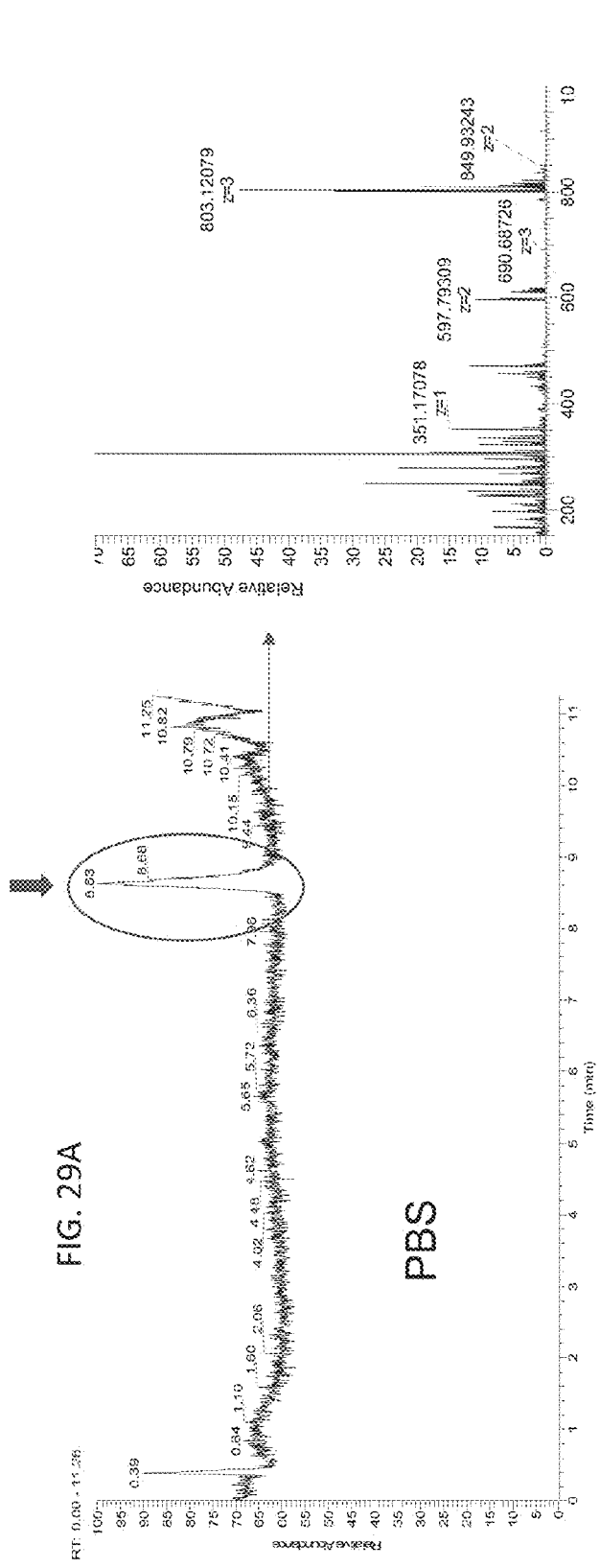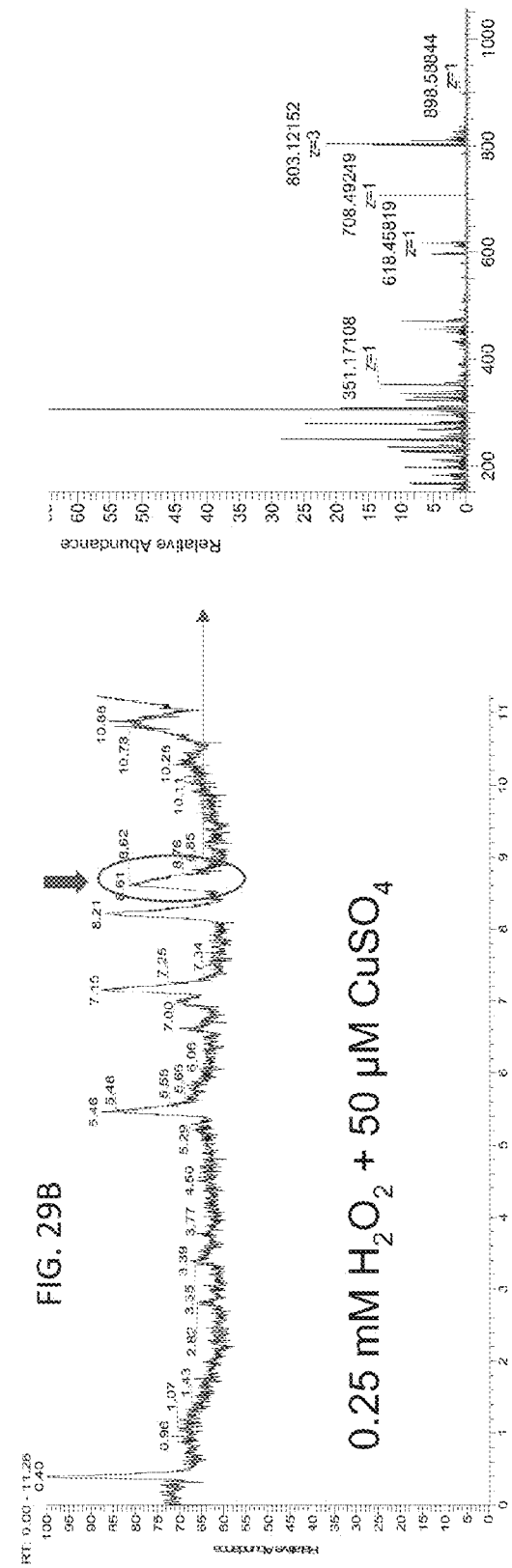

1 week
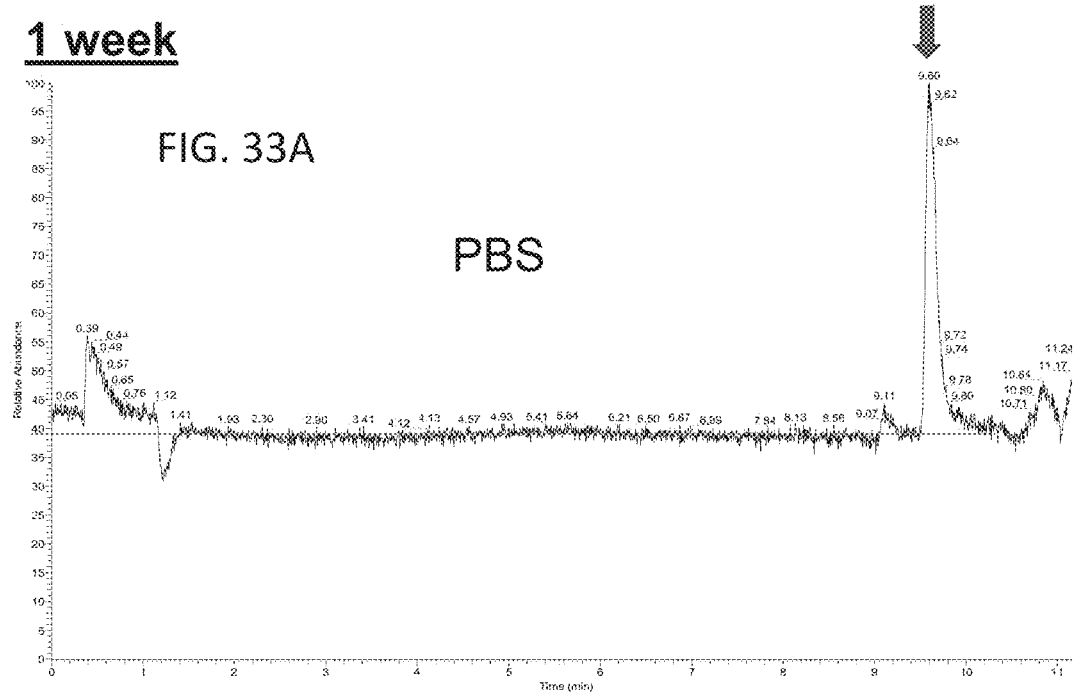
FIG. 33A PBS
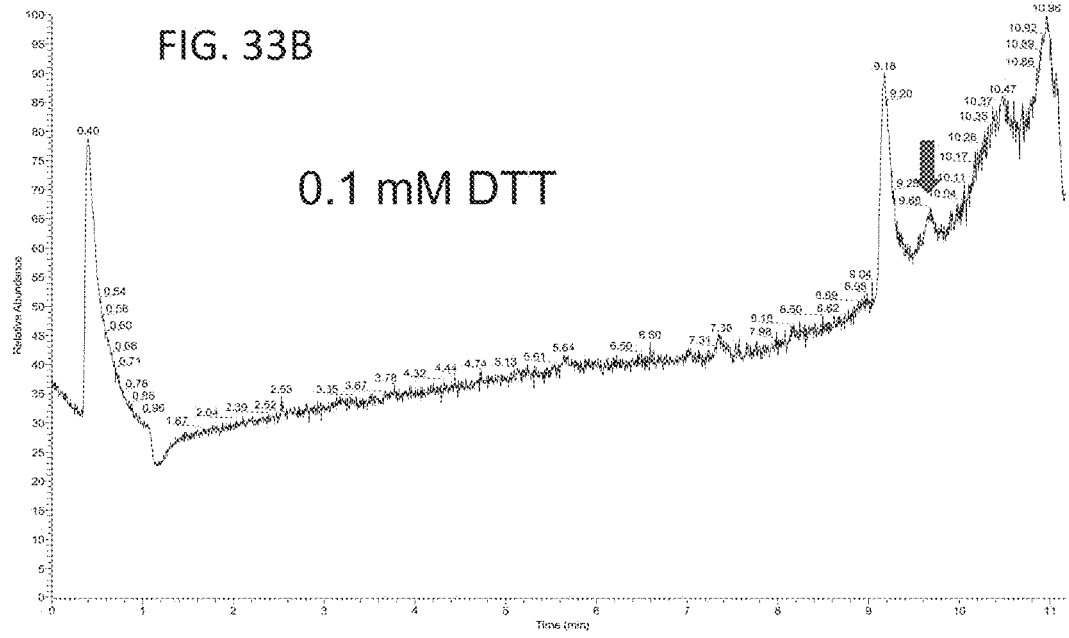
FIG. 33B 0.1 mM DTT

DRUG DELIVERY VEHICLES FOR ATHEROSCLEROSIS NANOMEDICINE

CROSS-REFERENCE TO RELATED APPLICATION

The present application claims priority to U.S. Provisional Patent Application Ser. No. 62/807,092, filed Feb. 18, 2019, which is hereby incorporated by reference in its entirety.

STATEMENT REGARDING FEDERALLY SPONSORED RESEARCH OR DEVELOPMENT

This invention was made with government support under grant numbers HL 116577, CA016086, and TR001422, awarded by the National Institutes of Health, and grant number 1542205 awarded by the National Science Foundation. The government has certain rights in the invention.

INCORPORATION-BY-REFERENCE OF MATERIAL SUBMITTED ELECTRONICALLY

The computer readable sequence listing filed herewith, titled "2023-03-29_37592-202_SQL_ST25", created Mar. 29, 2023, having a file size of 4,614 bytes, is hereby incorporated by reference in its entirety.

FIELD

Provided herein are peptide amphiphiles (PAs). In some embodiments, provided herein are targeting PAs comprising a PA backbone and a targeting moiety. In some embodiments, provided herein are therapeutic PAs comprising a PA backbone and a therapeutic agent. In some embodiments, the peptide amphiphiles are assembled into nanofibers. In some embodiments, the nanofibers may be used for the treatment of atherosclerosis or related disease.

BACKGROUND

Atherosclerosis is a chronic systemic disease of the vasculature characterized by impaired lipid metabolism and associated inflammatory responses, leading to stenotic or occluded arteries and tissue ischemia. Current interventions include pharmacological treatments to optimize the body's lipid profile and procedures to restore normal blood flow impeded by arterial stenosis or occlusion. 3-Hydroxy-3-methylglutaryl-coenzyme A (HMG-CoA) reductase inhibitors (i.e., statins) are the most commonly prescribed lipid regulators, as they effectively increase low density lipoprotein (LDL) catabolism. However, there is still a recurrence rate of over 20% within 30 months of an acute coronary syndrome in patients on statin therapy. Balloon angioplasty and stenting, surgical endarterectomy, or bypass grafting may be required when arterial stenosis or occlusion becomes severe, but restenosis or reocclusion often occurs postintervention due to neointimal hyperplasia. Hence, there is great need for alternative therapeutic strategies for the treatment of atherosclerosis and similar diseases.

SUMMARY

In some aspects, provided herein are peptide amphiphiles. In some embodiments, provided herein are peptide amphiphiles comprising a hydrophobic tail, a structural peptide segment, and a charged peptide segment. In some embodiments, the peptide amphiphile further comprises a targeting peptide capable of binding to an atherosclerotic lesion in a subject, or a therapeutic agent for the treatment of atherosclerosis in a subject. In some embodiments, the targeting peptide comprises an ApoA1-mimetic peptide. For example, the targeting peptide may comprise an ApoA1-mimetic peptide having at least 90% sequence identity to the amino acid sequence DWFKAFYDKVAEKFKEAF (SEQ ID NO: 2).

In some embodiments, the hydrophobic tail comprises an 8-24 carbon alkyl chain ($C_{8-24}$). In some embodiments, the structural peptide segment has a propensity for forming β-sheet conformations. For example, the structural peptide segment may comprise $V_2A_2$ (SEQ ID NO: 8). In some embodiments, the charged peptide segment comprises EE, EEE, or EEEE (SEQ ID NO: 11).

The targeting peptide may be attached to the charged peptide segment by a linker. In some embodiments, the linker is a single glycine (G) residue.

In some embodiments, the peptide amphiphile comprises a therapeutic agent for the treatment of atherosclerosis in a subject. In some embodiments, the therapeutic agent comprises an annexin A1 protein derivative or an LXR agonist. For example, the therapeutic agent may comprise Ac2-26 or GW3965. In some embodiments, the therapeutic agent is attached to the charged peptide segment by a cleavable linker. In some embodiments, the cleavable linker comprises a ROS-sensitive proline linker, a glutathione-sensitive disulfide linker, or an MMP2/9-sensitive linker. For example, the cleavable linker may comprise GGGPQGIWGQGK (SEQ ID NO: 1), KPPPPK (SEQ ID NO: 17), KPPPPPK (SEQ ID NO: 10), KPPPPPPK (SEQ ID NO: 18), KPPPPPPPK (SEQ ID NO: 19), KPPPPPPPPK (SEQ ID NO: 20), succinimidyl 3-(2-pyridyldithio)propionate (SPDP), or 4-nitrophenyl-2-(2-pyridyldithio)ethyl carbonate (NDEC).

In particular embodiments, the peptide amphiphile comprises $C_{8-24}$-$V_2A_2$ (SEQ ID NO: 8) $E_2$-(G)DWFKAFYDK-VAEKFKEAF (SEQ ID NO: 2), $C_{8-24}$-$V_2A_2$ (SEQ ID NO: 8)$E_2$-KP$_5$K (SEQ ID NO: 10)-AMVSEFLKQAWFIENE-EQEYVQTVK (SEQ ID NO: 7), $C_{8-24}$-$V_2A_2$ (SEQ ID NO: 8)-$E_2$-GGGPQGIWGQGK (SEQ ID NO: 1)-AMVSE-FLKQAWFIENEEQEYVQTVK (SEQ ID NO: 7), $C_{8-24}$-$V_2A_2$ (SEQ ID NO: 8)-$E_2$-KP$_5$K (SEQ ID NO: 10)-GW3965, $C_{8-24}$-$V_2A_2$ (SEQ ID NO: 8)-$E_2$-SDSP-GW3965, or $C_{8-24}$-$V_2A_2$ (SEQ ID NO: 8)-$E_2$-NDEC-GW3965.

In some aspects, provided herein are nanofibers comprising the peptide amphiphiles described herein. In some embodiments, provided herein are nanofibers comprising a targeting peptide amphiphile (e.g. a peptide amphiphile comprising a hydrophobic tail, a structural peptide segment, a charged peptide segment, and a targeting peptide capable of binding to an atherosclerotic lesion in a subject). In some embodiments, provided herein are nanofibers comprising a therapeutic peptide amphiphile (e.g. a peptide amphiphile comprising a hydrophobic tail, a structural peptide segment, a charged peptide segment, and a therapeutic agent for the treatment of atherosclerosis in a subject). In accordance with any of the embodiments described herein, the nanofiber further comprises one or more filler peptide amphiphiles. The filler peptide amphiphiles comprise a hydrophobic tail, a structural peptide segment, and a charged peptide segment, and do not comprise a targeting moiety or a therapeutic agent for the treatment of atherosclerosis in a subject.

In some embodiments, the nanofiber comprises a targeting peptide amphiphile comprising a hydrophobic tail, a structural peptide segment, a charged peptide segment, and a targeting peptide, wherein the targeting peptide is capable of binding to an atherosclerotic lesion in a subject, and one or more filler peptide amphiphiles, wherein the filler peptide amphiphiles comprise a hydrophobic tail, a structural peptide segment, and a charged peptide segment, and wherein the filler peptide amphiphiles do not comprise a targeting moiety.

In some embodiments, the targeting peptide comprises an ApoA1-mimetic peptide having at least 90% sequence identity to the amino acid sequence DWFKAFYDKVAEKFKEAF (SEQ ID NO: 2). In some embodiments, the hydrophobic tail comprises an 8-24 carbon alkyl chain ($C_{8-24}$). In some embodiments, the structural peptide segment has a propensity for forming β-sheet conformations. For example, the structural peptide segment may comprise $V_2A_2$ (SEQ ID NO: 8).

In some embodiments, the charged peptide segment comprises EE, EEE, or EEEE (SEQ ID NO: 11). In some embodiments, the targeting peptide is attached to the charged peptide segment by a linker. For example, the linker may be a single glycine (G) residue. In some embodiments, the peptide amphiphile comprises $C_{8-24}$-$V_2A_2$ (SEQ ID NO: 8)-$E_2$-(G)DWFKAFYDKVAEKFKEAF (SEQ ID NO: 2).

In some embodiments, the nanofiber further comprises therapeutic agent for the treatment of atherosclerosis in a subject. For example, the nanofiber comprising a targeting peptide amphiphile and one or more filler peptide amphiphiles may further comprise a therapeutic agent for the treatment of atherosclerosis in a subject. The therapeutic agent may be an LXR agonist.

For example, the therapeutic agent may be the LXR agonist GW3965. In some embodiments, the therapeutic agent is encapsulated within the nanofiber.

In some embodiments, the nanofiber comprises a targeting peptide amphiphile, one or more filler peptide amphiphiles, and a therapeutic peptide amphiphile (e.g. a peptide amphiphile comprising a hydrophobic tail, a structural peptide segment, a charged peptide segment, and a therapeutic agent for the treatment of atherosclerosis in a subject). In some embodiments, the therapeutic agent comprises an annexin A1 protein derivative or an LXR agonist. For example, the therapeutic agent may comprise Ac2-26 or GW3965. In some embodiments, the therapeutic agent is attached to the charged peptide segment by a cleavable linker. In some embodiments, the cleavable linker comprises a ROS-sensitive proline linker, a glutathione-sensitive disulfide linker, or an MMP2/9-sensitive linker. For example, the cleavable linker may comprise GGGPQGIWGQGK (SEQ ID NO: 1), KPPPPK (SEQ ID NO: 17), KPPPPPK (SEQ ID NO: 10), KPPPPPPK (SEQ ID NO: 18), KPPPPPPPK (SEQ ID NO: 19), KPPPPPPPPK (SEQ ID NO: 20), succinimidyl 3-(2-pyridyldithio)propionate (SPDP), or 4-nitrophenyl 2-(2-pyridyldithio)ethyl carbonate (NDEC). In some embodiments, the therapeutic peptide amphiphile comprises $C_{8-24}$-$V_2A_2$ (SEQ ID NO: 8)-$E_2$-KP$_5$K (SEQ ID NO: 10)-AMVSEFLKQAWFIENE-EQEYVQTVK (SEQ ID NO: 7), $C_{8-24}$-$V_2A_2$ (SEQ ID NO: 8)-$E_2$-GGGPQGIWGQGK (SEQ ID NO: 1)-AMVSEFLKQAWFIENEEQEYVQTVK (SEQ ID NO: 7), $C_{8-24}$-$V_2A_2$ (SEQ ID NO: 8)-$E_2$-KP$_5$K (SEQ ID NO: 10)-GW3965, $C_{8-24}$-$V_2A_2$ (SEQ ID NO: 8)-$E_2$-SDSP-GW3965, or $C_{8-24}$-$V_2A_2$ (SEQ ID NO: 8)-$E_2$-NDEC-GW3965.

In some aspects, provided herein are methods of treating atherosclerosis in a subject. The methods comprise providing to a subject a nanofiber as described herein. In some embodiments, the method comprises providing a nanofiber comprising a targeting peptide amphiphile, one or more filler peptide amphiphiles, and a therapeutic agent encapsulated within the nanofiber to the subject. In some embodiments, the method comprises providing a nanofiber comprising a targeting peptide amphiphile, one or more filler peptide amphiphiles, and a therapeutic peptide amphiphile to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1C shows structure and characterization of ApoA1 PA and 40% ApoA1 PA coassembled with 60% diluent PA. FIG. 1A shows chemical structures of ApoA1 PA and diluent PA along with a molecular graphics representation of the coassembly. FIG. 1B shows room-temperature TEM of 100% ApoA1 PA, showing formation of aggregates rather than nanofibers. FIG. 1C shows Cryo-TEM of 40% ApoA1 PA.

FIG. 3A-3E shows characterization of LXR-40% ApoA1 PA encapsulation. FIG. 3A shows cryo-TEM, showing formation of nanofibers similar to those of PA without encapsulated LXR agonist. FIG. 3B shows LXR-encapsulation by 40% ApoA1 PA resulted in a more β-sheet-like CD spectrum. FIG. 3C shows tryptophan fluorescence quenching of PA occurred upon encapsulation of LXR agonist. FIG. 3D shows that neither the PA, 4F, LXR, nor the LXR-PA treatments increased percent cholesterol efflux above the control (DMEM) at t=1 h, but LXR-40% ApoA1 PA did induce significant (*$p<0.05$) efflux above the control, 4F, 40% ApoA1 PA, Diluent PA, and LXR at t=4 h. FIG. 3E shows the effect of PA, peptide, and LXR treatments upon macrophage cell viability in vitro. * indicates $p<0.05$ versus LXR-40% ApoA1 PA and LXR.

FIG. 6A-6G. Bright field images of aortic roots of (FIG. 6A) a nonatherogenic wild type C57/B16 mice on regular chow stained with H&E and (FIG. 6B) an atherosclerotic LDLR-KO mice fed a high fat diet for 14 weeks stained with H&E and oil-red-O, note lipids/atherosclerosis stained in red. (FIG. 6C) Quantification of Oil Red O staining of aortic root regions in FIG. 6A and FIG. 6B. Fluorescent microscopy of aortic roots of LDLR-KO mouse fed a high fat diet for 14 weeks, injected with (FIG. 6D) nontargeted PA, (FIG. 6E) targeted PA (ApoA1 PA), and (FIG. 6F) therapeutic targeted PA (LXR-40% ApoA1 PA); all mice in C-E sacrificed 24 h after injection. Red fluorescence represents Alexa Fluor 546 and indicates presence of nanofibers. The elastic laminae of the vessel walls are auto fluorescent and were visualized with a green filter. (FIG. 6G) Quantification of PA binding to the aortic root in (FIG. 6D)-(FIG. 6F). Injections were given at a dose of 6 mg kg-1 PA or 6 mg kg-1 PA+6 mg kg-1 LXR. All images were taken with the 5× objective.

(FIG. 9D) PA nanostructure length was quantified with conditions not containing the same letter significantly different, p<0.05, n≥32 nanostructures analyzed per condition.

(FIG. 10A) 10% MMP-Ac2-26 PA treated with 40 nM MMP2 for 24 hours and analyzed for a product scan of m/z=940-948. (FIG. 10B) 10% MMP-Ac2-26 PA without MMP2 treatment. The peak at 6.5-7 minutes contains uncleaved MMP-Ac2-26 PA and ApoA1 PA, the peak near 8.2 minutes indicates E2 filler PA (FIG. 10C) ROS-Ac2-26 PA treated with 100 µM SIN-1 for 24 hours and analyzed for a product scan of m/z=947-1030. (FIG. 10D) ROS-Ac2-26 PA without SIN-1 treatment. Uncleaved ROS-Ac2-26 PA is present in the peaks at both 5.4 and 6.5 minutes.

(FIG. 16A) The effect of 24 hours of treatment with 10% MMP-Ac2-26 PA, 10% ROS-Ac2-26 PA, or Ac2-26 peptide on J774.2 macrophage viability. No significant differences (p<0.05) were observed between groups. n≥3 independent experiments per condition. (FIG. 16B) Cellular uptake of PAs assessed by the integrated pixel density of Alexa Fluor 546-tagged PAs found within the cell. *p<0.05, #p<0.05 vs. 24 hours 10% ROS-Ac2-26 PA, ˆp<0.05 vs. 24 hours 10% MMP-Ac2-26 PA. n≥32 cells analyzed per condition. (FIG. 16C) Manders colocalization coefficient values after 24 hours of treatment with 10% ROS- or MMP-Ac2-26 PAs. M1 indicates colocalization of AF546 PA pixels vs. LAMP1 pixels, M2 indicates the reverse. *p<0.05, n≥180 cells analyzed per condition. (FIG. 16D) Representative images of ApoA1-Ac2-26 PA colocalization to macrophages after 24 hours of treatment. Scale bar equals 20 µm.

(FIG. 18A) Ratio of nitric oxide (NO) production in comparison to the stimulated control. Letters not connected by the same letter are significantly different (p<0.05). n≥7 independent experiments for each condition. Error bars indicate S.E.M. (FIG. 18B) Cellular metabolic activity measured by an MTT assay using absorbance at 560 nm. n=3 per condition. *p<0.05. (FIG. 18C) Percentage of cells expressing iNOS assayed by flow cytometry. *p<0.05, $p<0.05 vs. Stimulated, #p<0.05 vs. 40ApoA1 PA, n≥4 per condition. (FIG. 18D) Representative histogram for effect of PA and peptide treatments upon iNOS expression. RL1-A indicates the APC channel used to measure fluorescence. The dotted lines indicate reference peak values for unstimulated and stimulated conditions.

FIG. 20A-20D. Characterization of PAs and peptides. (FIG. 20A-20B) Circular dichroism spectroscopy analysis for secondary structure of ApoA1 PA co-assembly, diluent PA, 4F peptide (4F), 4F-LXR, ApoA1-LXR PA co-assembly, and scrambled PA (Scr PA) co-assembly taken at 25° C. (FIG. 20C) Dynamic light scattering analysis of PAs and peptides taken at 25° C. and 37° C., n=3 independent experiments analyzed per condition, error bars represent SEM, *p<0.05. (FIG. 20D) TEM images of 4F and 4F-LXR peptides; ApoA1, ApoA1-LXR, and Scr PA co-assemblies; and diluent PA. Scale bar equals 200 nm.

(FIG. 23A) Timeline for low density lipoprotein receptor knockout mice (LDLR KO) fed the high fat diet, injection, and sacrifice. (FIG. 23B) Spectrally unmixed confocal images of aortic root sections. Blue=DAPI-stained cell nuclei, Green=autofluorescent elastic laminae and atherosclerosis, and Red=Alexa Fluor® 546-labeled injected compound.

(FIG. 24A) Determination of optimum concentration of ApoA1 PA in PBS at 8 mg/kg dose with (FIG. 24B) representative images. (FIG. 24C) Determination of optimum dose of ApoA1 in at 2 mg/mL concentration in PBS with (FIG. 24D) representative images. (FIG. 24E) Comparison of targeting efficacy of ApoA1 PA between males and females with (FIG. 24F) representative images. All images are fluorescent microscopy of representative sections displayed at 5× magnification, n=3-5 per group. *p<0.05.

FIG. 25A-25B. Binding duration of ApoA1-targeted nanofiber in the aortic root. (FIG. 25A) Red fluorescent pixel quantification in the aortic root. (FIG. 25B) Fluorescent microscopy images of representative sections at 5× magnification, n=3-5 per group. *p<0.05.

FIG. 26A-26E. Pharmacokinetics of ApoA1 PA circulation through internal organs. Red fluorescent pixel quantification in the Lung (FIG. 26A), Liver (FIG. 26B), Kidney (FIG. 26C), and Spleen (FIG. 26D) from 1 day to 2 weeks post injection. (FIG. 26E) Fluorescent microscopy images of representative sections at 20× magnification, n=3-5 per group.

FIG. 27A-D. Atherosclerosis Treatment Study. (FIG. 27A) Timeline for low density lipoprotein receptor knockout (LDLR KO) mice fed the high fat diet, treatment injections, and sacrifice. (FIG. 27B) Effects of treatment on atherosclerosis progression. *p<0.05, error bars are S.E.M. Atherosclerosis represented as percentage of aortic root in all mice. PBS: n=8 mice-5 male, 3 female; Scr PA: n=10 mice-5 male, 5 female; LXR: n=9 mice-4 male, 5 female; ApoA1 PA: n=10 mice-5 male, 5 female; ApoA1 LXR PA: n=9 mice-4 male, 5 female. At least four cross sections were analyzed per treatment. (FIG. 27C) Effects of treatment and sex on plaque size reduction. With respect to sex, the percentage of atherosclerosis per treatment was subtracted from the averaged PBS control. *p<0.05, #p<0.05 against male scrambled PA. Error bars are S.E.M. (FIG. 27D) Brightfield images of representative sections of Oil Red O-stained aortic roots at 5× magnification.

FIG. 29A-30B shows cleavage after treatment with physiologically relevant levels of $H_2O_2$+$CuSO_4$ for ROS-LXR PAs. Results after 24 hours are shown.

FIG. 30A-30B show cleavage after treatment with $H_2O_2$+$CuSO_4$ for ROS-LXR PAs. FIG. 30A shows results after 4 days. FIG. 30B shows results after 1 week. The ROS-LXR PA is completely cleaved by 4 days of 0.25 mM $H_2O_2$+$CuSO_4$ treatment.

FIG. 33A-33C show results for SPDP-LXR PAs after treatment with PBS (FIG. 33A) or DTT (FIG. 33B-33C). FIG. 33B shows results after treatment with 0.1 mM DTT. FIG. 33C shows results after treatment with 10 mM DTT. Results after 1 week are shown.

FIG. 37A shows 10% PEG-ROS-LXR PA. FIG. 37B shows 10% PEG-SPDP-LXR-PA.

FIG. 37C shows 40% PEG-ApoA1 PA. FIG. 37D shows the E2 PA.

DEFINITIONS

Figure 2B:
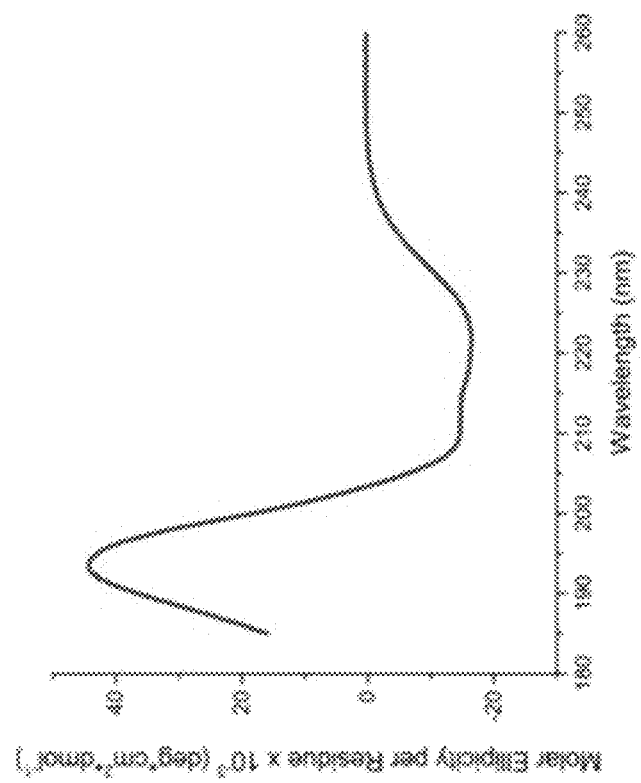
FIG. 2B shows CD spectra of the 4F peptide.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a peptide amphiphile" is a reference to one or more peptide amphiphiles and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO:Z (e.g., 100 amino acids) may have up to X substitutions (e.g., 10) relative to SEQ ID NO:Z, and may therefore also be expressed as "having X (e.g., 10) or fewer substitutions relative to SEQ ID NO:Z."

As used herein, the term "nanofiber" refers to an elongated or threadlike filament (e.g., having a significantly greater length dimension that width or diameter) with a diameter typically less than 100 nanometers.

As used herein, the term "scaffold" refers to a material capable of supporting growth and differentiation of a cell.

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

As used herein, the term "peptide amphiphile" refers to a molecule that, at a minimum, includes a non-peptide lipophilic (hydrophobic) segment, a structural peptide segment and/or charged peptide segment (often both). The peptide amphiphile may express a net charge at physiological pH, either a net positive or negative net charge, or may be zwitterionic (i.e., carrying both positive and negative charges).

The term "peptide amphiphile backbone", "backbone", or "PA backbone" is used herein to refer to a peptide amphiphile comprising a hydrophobic segment, a structural peptide segment, and a charged peptide segment. The PA backbone may be attached to a targeting peptide or a therapeutic peptide to generate a "targeting peptide amphiphile" or a "therapeutic peptide amphiphile", respectively.

Certain peptide amphiphiles consist of or comprise (1) a hydrophobic, non-peptide segment (e.g., comprising an acyl group of six or more carbons), (2) a structural peptide segment; (3) a charged peptide segment, and (4) a targeting moiety segment. Certain peptide amphiphiles consist of or comprise: (1) a hydrophobic, non-peptide segment (e.g., comprising an acyl group of six or more carbons), (2) a structural peptide segment; (3) a charged peptide segment, and (4) a therapeutic agent.

The term "peptide amphiphile" includes both a "targeting peptide amphiphile" and a "therapeutic peptide amphiphile". A "targeting peptide amphiphile" or "targeting PA" refers to a peptide amphiphile containing a non-peptide lipophilic (hydrophobic) segment, a structural peptide segment and/or charged peptide segment, and a targeting moiety. A "therapeutic peptide amphiphile" or a "therapeutic PA" refers to a peptide amphiphile containing a non-peptide lipophilic (hydrophobic) segment, a structural peptide segment and/or charged peptide segment, and a therapeutic agent. For example, the therapeutic PA may comprise a therapeutic agent for the treatment and/or prevention of atherosclerosis.

As used herein and in the appended claims, the term "lipophilic moiety" or "hydrophobic moiety" refers to the moiety (e.g., an acyl, ether, sulfonamide, or phosphodiester moiety) disposed on one terminus (e.g., C-terminus, N-terminus) of the peptide amphiphile, and may be herein and elsewhere referred to as the lipophilic or hydrophobic segment or component. The hydrophobic segment should be of a sufficient length to provide amphiphilic behavior and aggregate (or nanosphere or nanofiber) formation in water or another polar solvent system.

Accordingly, in the context of the embodiments described herein, the hydrophobic component preferably comprises a single, linear acyl chain of the formula: $C_{n-1}H_{2n-1}C(O)$— where n=2-25. In some embodiments, a linear acyl chain is the lipophilic group (saturated or unsaturated carbons), palmitic acid. However, other lipophilic groups may be used in place of the acyl chain such as steroids, phospholipids and fluorocarbons.

As used interchangeably herein, the terms "structural peptide" or "structural peptide segment" refer to a portion of a peptide amphiphile, typically disposed between the hydrophobic segment and the charged peptide segment. The structural peptide is generally composed of three to ten amino acid residues with non-polar, uncharged side chains (e.g., His (H), Val (V), Ile (I), Leu (L), Ala (A), Phe (F)) selected for their propensity to form hydrogen bonds or other stabilizing interactions (e.g., hydrophobic interactions, van der Waals' interactions, etc.) with structural peptide segments of adjacent structural peptide segments. In some embodiments, nanofibers of peptide amphiphiles having structural peptide segments display linear or 2D structure when examined by microscopy and/or α-helix and/or β-sheet character when examined by circular dichroism (CD).

As used herein, the term "beta (β)-sheet-forming peptide segment" refers to a structural peptide segment that has a propensity to display β-sheet-like character (e.g., when analyzed by CD). In some embodiments, amino acids in a beta (β)-sheet-forming peptide segment are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used. Peptide segments capable of interacting to form beta sheets and/or with a propensity to form beta sheets are understood (See, e.g., Mayo et al. Protein Science (1996), 5:1301-1315; herein incorporated by reference in its entirety).

As used herein, the term "charged peptide segment" refers to a portion of a peptide amphiphile that is rich (e.g., >50%, >75%, etc.) in charged amino acid residues, or amino acid residue that have a net positive or negative charge under physiologic conditions. A charged peptide segment may be acidic (e.g., negatively charged), basic (e.g., positively charged), or zwitterionic (e.g., having both acidic and basic residues).

As used herein, the terms "carboxy-rich peptide segment," "acidic peptide segment," and "negatively-charged peptide segment" refer to a peptide sequence of a peptide amphiphile that comprises one or more amino acid residues that have side chains displaying carboxylic acid side chains (e.g., Glu (E), Asp (D), or non-natural amino acids). A carboxy-rich peptide segment may optionally contain one or more additional (e.g., non-acidic) amino acid residues. Non-natural amino acid residues, or peptidomimetics with acidic side chains could be used, as will be evident to one ordinarily skilled in the art. There may be from about 2 to about 7 amino acids, and or about 3 or 4 amino acids in this segment.

As used herein, the terms "amino-rich peptide segment", "basic peptide segment," and "positively-charged peptide segment" refer to a peptide sequence of a peptide amphiphile that comprises one or more amino acid residues that have side chains displaying positively-charged acid side chains (e.g., Arg (R), Lys (K), His (H), or non-natural amino acids, or peptidomimetics). A basic peptide segment may optionally contain one or more additional (e.g., non-basic) amino acid residues. Non-natural amino acid residues with basic side chains could be used, as will be evident to one ordinarily skilled in the art. There may be from about 2 to about 7 amino acids, and or about 3 or 4 amino acids in this segment.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%.

As used herein, "biodegradable" as used to describe the polymers, hydrogels, and/or wound dressings herein refers to compositions degraded or otherwise "broken down" under exposure to physiological conditions. In some embodiments, a biodegradable substance is a broken down by cellular machinery, enzymatic degradation, chemical processes, hydrolysis, etc. In some embodiments, a wound dressing or coating comprises hydrolyzable ester linkages that provide the biodegradability.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the terms "treat," "treatment," and "treating" refer to reducing the amount or severity of a particular condition, disease state (e.g., atherosclerosis), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the terms "prevent," "prevention," and preventing" refer to reducing the likelihood of a particular condition or disease state (e.g., atherosclerosis) from occurring in a subject not presently experiencing or afflicted with the condition or disease state. The terms do not necessarily indicate complete or absolute prevention. For example "preventing atherosclerosis" refers to reducing the likelihood of atherosclerosis occurring in a subject not presently experiencing or diagnosed with atherosclerosis. In order to "prevent atherosclerosis" a composition or method need only reduce the likelihood of atherosclerosis, not completely block any possibility thereof. "Prevention," encompasses any administration or application of a therapeutic or technique to reduce the likelihood of a disease developing (e.g., in a mammal, including a human). Such a likelihood may be assessed for a population or for an individual.

As used herein, the terms "co-administration" and "co-administering" refer to the administration of at least two agent(s) or therapies to a subject (e.g., a PA nanofiber and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION

In some aspects, provided herein are peptide amphiphiles (PAs). In some embodiments, provided herein are PAs comprising a targeting moiety (e.g. targeting PAs). In some aspects, provided herein are PAs comprising a therapeutic agent (e.g. therapeutic PAs). In some embodiments, provided herein are nanofibers comprising the targeting PAs and/or therapeutic PAs described herein. Further provided herein are methods of use of the targeting PAs, therapeutic PAs, and nanofibers disclosed herein.

In some embodiments, the peptide amphiphile molecules and compositions of the embodiments described herein are synthesized using preparatory techniques well-known to those skilled in the art, preferably, by standard solid-phase peptide synthesis, with the addition of a fatty acid in place of a standard amino acid at the N-terminus (or C-terminus) of the peptide, in order to create the lipophilic segment (although in some embodiments, alignment of nanofibers is performed via techniques not previously disclosed or used in the art (e.g., extrusion through a mesh screen). Synthesis typically starts from the C-terminus, to which amino acids are sequentially added using either a Rink amide resin (resulting in an —NH2 group at the C-terminus of the peptide after cleavage from the resin), or a Wang resin (resulting in an —OH group at the C-terminus). Accordingly, some embodiments described herein encompass peptide amphiphiles having a C-terminal moiety that may be selected from the group consisting of —H, —OH, —COOH, —CONH2, and —NH2.

In some embodiments, peptide amphiphiles comprise a hydrophobic segment (i.e. a hydrophobic tail) linked to a peptide. In some embodiments, the peptide comprises a structural peptide segment. In some embodiments, the structural peptide segment is a hydrogen-bond-forming segment, or beta-sheet-forming segment. In some embodiments, the structural peptide segment has the propensity to form random coil structures. In some embodiments, the peptide comprises a charged segment (e.g., acidic segment, basic segment, zwitterionic segment, etc.).

In some embodiments, the peptide further comprises linker or spacer segments for adding solubility, flexibility, distance between segments, etc. In some embodiments, peptide amphiphiles comprise a spacer segment (e.g., peptide and/or non-peptide spacer) at the opposite terminus of the peptide from the hydrophobic segment. In some embodiments, the spacer segment comprises peptide and/or non-peptide elements. In some embodiments, the spacer segment comprises one or more bioactive groups (e.g., alkene, alkyne, azide, thiol, etc.). In some embodiments, various segments may be connected by linker segments (e.g., peptide or non-peptide (e.g., alkyl, OEG, PEG, etc.) linkers).

The lipophilic or hydrophobic segment is typically incorporated at the N- or C-terminus of the peptide after the last amino acid coupling, and is composed of a fatty acid or other acid that is linked to the N- or C-terminal amino acid through an acyl bond. In aqueous solutions, PA molecules may self-assemble (e.g., into cylindrical micelles (a.k.a., nanofibers)) to bury the lipophilic segment in their core. In some embodiments, the targeting PA alone does not self-assemble into a nanofiber. In such cases, the targeting PA may be coassembled with a filler PA (e.g. diluent PA) to induce assembly into a nanofiber formation. In some embodiments, targeting PAs, diluent PAs, and therapeutic PAs may coassemble into a nanofiber. In some embodiments, the structural peptide undergoes intermolecular hydrogen bonding to form beta sheets that orient parallel to the long axis of the micelle.

In some embodiments, compositions described herein comprise PA building blocks that in turn comprise a hydrophobic segment and a peptide segment. In certain embodiments, a hydrophobic (e.g., hydrocarbon and/or alkyl/alkenyl/alkynyl tail, or steroid such as cholesterol) segment of sufficient length (e.g., 2 carbons, 3 carbons, 4 carbons, 5 carbons, 6 carbons, 7 carbons, 8 carbons, 9 carbons, 10 carbons, 11 carbons, 12 carbons, 13 carbons, 14 carbons, 15 carbons, 16 carbons, 17 carbons, 18 carbons, 19 carbons, 20 carbons, 21 carbons, 22 carbons, 23 carbons, 24 carbons, 25 carbons, 26 carbons, 27 carbons, 28 carbons, 29 carbons, 30 carbons or more, or any ranges there between.) is covalently coupled to peptide segment (e.g., a peptide comprising a segment having a preference for beta-strand conformations or other supramolecular interactions) to yield a peptide amphiphile molecule. In some embodiments, a plurality of such PAs will self-assemble in water (or aqueous solution) into a nanostructure (e.g., nanofiber). In various embodiments, the relative lengths of the peptide segment and hydrophobic segment result in differing PA molecular shape and nanostructural architecture. For example, a broader peptide segment and narrower hydrophobic segment results in a generally conical molecular shape that has an effect on the assembly of PAs (See, e.g., J. N. Israelachvili Intermolecular and surface forces; 2nd ed.; Academic: London San Diego, 1992; herein incorporated by reference in its entirety). Other molecular shapes have similar effects on assembly and nanostructural architecture.

In some embodiments, to induce self-assembly of an aqueous solution of peptide amphiphiles, the pH of the solution may be changed (raised or lowered) or multivalent ions, such as calcium, or charged polymers or other macromolecules may be added to the solution. In some embodiments, to induce self-assembly one or more diluent PAs may be added to an aqueous solution containing targeting and/or therapeutic PAs.

In some embodiments, the hydrophobic segment is a non-peptide segment (e.g., alkyl/alkenyl/alkynyl group). In some embodiments, the hydrophobic segment comprises an alkyl chain (e.g., saturated) of 4-25 carbons (e.g., 4, 5, 6, 7, 8, 9, 10, 11, 12, 13, 14, 15, 16, 17, 18, 19, 20, 21, 22, 23, 24, 25), fluorinated segments, fluorinated alkyl tails, heterocyclic rings, aromatic segments, pi-conjugated segments, cycloalkyls, oligothiophenes etc. In some embodiments, the hydrophobic segment comprises an acyl/ether chain (e.g., saturated) of 2-30 carbons (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30).

In some embodiments, PAs comprise one or more peptide segments. Peptide segment may comprise natural amino acids, modified amino acids, unnatural amino acids, amino acid analogs, peptidomimetics, or combinations thereof. In some embodiments, peptide segment comprise at least 50% sequence identity or similarity (e.g., conservative or semi-conservative) to one or more of the peptide sequences described herein.

In some embodiments, peptide amphiphiles comprise a charged peptide segment. The charged segment may be acidic, basic, or zwitterionic.

In some embodiments, peptide amphiphiles comprise an acidic peptide segment. For example, in some embodiments, the acidic peptide comprises one or more (e.g., 1, 2, 3, 4, 5, 6, 7, or more) acidic residues (D and/or E) in sequence. In some embodiments, the acidic peptide segment comprises up to 7 residues in length and comprises at least 50% acidic residues. In some embodiments, an acidic peptide segment comprises $(Xa)_{1-7}$, wherein each Xa is independently D or E. In some embodiments, an acidic peptide segment comprises EE, EEE, or EEEE (SEQ ID NO: 11). For example, in some embodiments an acidic peptide segment comprises EE. In some embodiments, an acidic peptide segment comprises EEE. In other embodiments, an acidic peptide segment comprises EEEE (SEQ ID NO: 11).

In some embodiments, peptide amphiphiles comprise a basic peptide segment. For example, in some embodiments, the acidic peptide comprises one or more (e.g., 1, 2, 3, 4, 5, 6, 7, or more) basic residues (R, H, and/or K) in sequence. In some embodiments, the basic peptide segment comprises up to 7 residues in length and comprises at least 50% basic residues. In some embodiments, an acidic peptide segment comprises $(Xb)_{1-7}$, wherein each Xb is independently R, H, and/or K.

In some embodiments, peptide amphiphiles comprises a structural peptide segment. In some embodiments, the structural peptide segment is a beta-sheet-forming segment. In some embodiments, the structural peptide segment displays weak hydrogen bonding and has the propensity to form random coil structures rather than rigid beta-sheet conformations. In some embodiments, the structural peptide segment is rich in one or more of H, I, L, F, V, G, and A residues. In some embodiments, the structural peptide segment comprises an alanine- and valine-rich peptide segment (e.g., VVAA (SEQ ID NO: 8), VVVAAA (SEQ ID NO: 14), AAVV (SEQ ID NO: 15), AAAVVV (SEQ ID NO: 16), or other combinations of V and A residues, etc.). In some embodiments, the structural peptide segment comprises 4 or more consecutive A and/or V residues, or conservative or semi-conservative substitutions thereto. In some embodiments, the structural peptide segment comprises $V_2A_2$ (SEQ ID NO: 8).

In some embodiments, peptide amphiphiles comprise a spacer or linker segment. In some embodiments, the spacer or linker segment is located at the opposite terminus of the peptide from the hydrophobic segment. In some embodiments, the linker segment is a non-peptide linker. In some embodiments, the spacer or linker segment provides the attachment site for a bioactive group. In some embodiments, the spacer or linker segment provides a reactive group (e.g., alkene, alkyne, azide, thiol, maleimide etc.) for functionalization of the PA. In some embodiments, the spacer or linker is a substantially linear chain of $CH_2$, O, $(CH_2)_2O$, $O(CH_2)_2$, NH, and C=O groups (e.g., $CH_2(O(CH_2)_2)_2NH$, $CH_2(O(CH_2)_2)_2NHCO(CH_2)_2CCH$, etc.). In some embodiments, a spacer or linker further comprises additional bioactive groups, substituents, branches, etc. In some embodiments, the linker segment is a single glycine (G) residue.

In some embodiments, the linker segment is a peptide segment. In some embodiments, the linker segment is cleavable. For example, the linker segment may comprise a cleavable linker that cleaves in response to the atherosclerotic environment. In some embodiments, the linker segment may be an MMP2/9-sensitive peptide sequence. For example, the linker segment may be the MMP2/9-sensitive peptide sequence GGGPQGIWGQGK (SEQ ID NO: 1). The sequence is also described herein as GGGPQGIWGQGK (SEQ ID NO: 1), with J denoting the cleavage site. In some embodiments, the linker segment may be a reactive oxygen species (ROS) sensitive linker. For example, the linker segment may be a ROS-sensitive (e.g. ROS-cleavable) linker comprising two or more proline residues. For example, the linker segment may comprise two, three, four, five, six, seven, eight, nine, ten, or more than ten proline residues. In particular embodiments, the proline-based ROS sensitive linker may further comprise lysine residues to enhance stability. For example, the linker segment may comprise KPPPPK (SEQ ID NO: 17), KPPPPPK (SEQ ID NO: 10), KPPPPPPK (SEQ ID NO: 18), KPPPPPPPK (SEQ ID NO: 19), KPPPPPPPPK (SEQ ID NO: 20). For example, the linker segment may comprise $KP_5K$ (SEQ ID NO: 10).

In some embodiments, the linker segment is a glutathione (GSH) sensitive linker. For example, the linker segment may be a GSH-sensitive disulfide linker. Exemplary linkers include, for example, succinimidyl 3-(2-pyridyldithio)propionate (SPDP), or 4-nitrophenyl 2-(2-pyridyldithio)ethyl carbonate (NDEC). The structures of SPDP and NDEC are shown below:

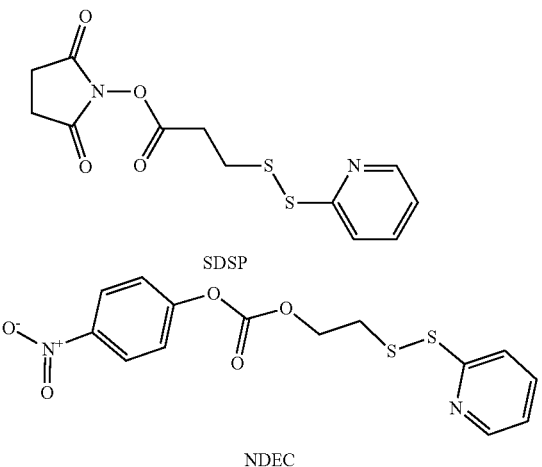

SDSP

NDEC

In some embodiments, peptide amphiphiles comprise a targeting moiety. Peptide amphiphiles comprising a targeting moiety are referred to herein as "targeting peptide amphiphiles". A targeting moiety may be any suitable moiety that enables targeted delivery of the PA to a desired location. For example, the targeting moiety may be a targeting peptide. In some embodiments, the targeting moiety enables targeted delivery of the PA to the arteries of the heart. For example, the targeting moiety may be a peptide that binds to one or more components of arteries affected by atherosclerosis (e.g. atherosclerotic lesions). Atherosclerotic lesions, also referred to herein as atherosclerotic plaques or atheroma, comprise lipids, cholesterol, calcium, and fibrous connective tissue. Accordingly, the targeting moiety may bind to any one or more of these components of atheroma. For example, the targeting moiety may be a peptide capable of binding to atherosclerotic lesions. ApoA1 is the primary protein component of high-density lipoprotein particles, and its amphipathic α-helices are instrumental in lipid binding, transport, and metabolism. In some embodiments, the targeting peptide may be an ApoA1 peptide or an ApoA1 mimetic peptide. For example, the targeting peptide may comprise an amino acid sequence with at least 80% sequence identity (e.g. 80%, 85%, 90%, 91%, 92%, 93%, 94%, 95%, 96%, 97%, 98%, 99%, or 100%) to DWFKAFYDKVAEKFKEAF (SEQ ID NO: 2). As another example, the targeting peptide may comprise a peptide with at least 80% sequence identity to any of the following other ApoA1 mimetic peptides: CGVLESFKASFLSALEE-WTKKLQ (SEQ ID NO: 3), DWLKAFYDKVAEKLKEAF (18A, SEQ ID NO: 4), DWLKAFYDK-VAEKLKEAFPDWLKAFYDKVAEKLKEAF (37 pA, SEQ ID NO: 5), and FAEKFKEAVKDYFAKFWD (SEQ ID NO: 6).

In some embodiments, the targeting peptides may target endothelial cells, macrophages, smooth muscle cells, monocytes, macrophages, platelets, collagen, and/or fibrin. For example, the targeting peptides may target VCAM1, IL-4 receptor, stabilin, CCR2, CCR5, Lyp-1, Apo E, integrin, GPIIb-IIIa, Type 1 collagen, type IV collagen, or fibrin.

In some embodiments, peptide amphiphiles comprise a therapeutic agent. The peptide amphiphile may comprise a therapeutic agent for the treatment and/or prevention of atherosclerosis. The therapeutic agent may be attached (e.g. tethered) to the cleavable linker. In some embodiments, the therapeutic agent is attached to the cleavable linker by an attachment residue, such as a lysine residue. An emerging therapeutic strategy to reduce plaque burden is to address the cell-mediated inflammation involved in atherosclerosis. In particular, Ac2-26, a peptide derived from the glucocorticoid annexin A1 protein, can resolve inflammation within atherosclerotic lesions through its pleiotropic interactions with formyl peptide receptor 2 (FPR2), which is expressed on vascular endothelial cells, leukocytes, and macrophages. Accordingly, in some embodiments the therapeutic agent may comprise an annexin A1 protein derivative, such as Ac2-26.

In some embodiments, the therapeutic agent may comprise an LXR agonist. The LXR agonist may be a natural or a synthetic agonist. Suitable LXR agonists include, for example, hypocholamide, T0901317, GW3965, N,N-dimethyl-3beta-hydroxy-cholenamide (DMHCA), T0901317, 22(R)-hydroxycholesterol, and 24(S)-hydroxycholesterol. In some embodiments, the therapeutic agent is the LXR agonist GW3965. In some embodiments, the LXR agonist may be a part of the peptide amphiphile (e.g. attached to one or more other segments of the PA). For example, the LXR agonist may be attached (e.g. tethered) to the cleavable linker. In some embodiments, the therapeutic agent is attached to the cleavable linker by an attachment residue, such as a lysine residue. In other embodiments, the LXR agonist may be encapsulated within a nanofiber comprising a targeting peptide amphiphile and one or more diluent peptide amphiphiles. For example, the LXR agonist GW3965 may be encapsulated within a nanofiber comprising the ApoA1 targeting PA and one or more filler PAs.

The targeting PAs (e.g. ApoA1 PAs) can serve as drug delivery carriers that enable retrofitting of therapeutics shown to be effective in reducing plaque burden, but which are toxic when administered systemically. For example, the liver X receptor (LXR) agonist acts as a cholesterol sensor and induces cholesterol efflux from macrophages. When activated, the LXR on macrophages directly reduces foam cell formation and lesion cholesterol content. However, in systemic doses, LXR agonists cause liver steatosis and are consequently precluded from being used systemically in humans. Therefore, a targeted ApoA1 PA nanofiber may be used to deliver an LXR agonist directly to sites of atherosclerosis, in smaller doses than have been used systemically in the past, to induce atherosclerotic plaque regression.

Suitable peptide amphiphiles for use in the materials herein, as well as methods of preparation of PAs and related materials, amino acid sequences for use in PAs, and materials that find use with PAs, are described in the following patents: U.S. Pat. Nos. 9,044,514; 9,040,626; 9,011,914; 8,772,228; 8,748,569 U.S. Pat. Nos. 8,580,923; 8,546,338; 8,512,693; 8,450,271; 8,236,800; 8,138,140; 8,124,583; 8,114,835; 8,114,834; 8,080,262; 8,076,295; 8,063,014; 7,851,445; 7,838,491; 7,745,708; 7,683,025; 7,554,021; 7,544,661; 7,534,761; 7,491,690; 7,452,679; 7,371,719; 7,030,167; all of which are herein incorporated by reference in their entireties.

The characteristics (e.g., shape, rigidity, hydrophilicity, etc.) of a PA supramolecular structure depend upon the identity of the components of a peptide amphiphile (e.g., lipophilic segment, acidic segment, structural peptide segment, targeting moiety, therapeutic agent, etc.). For example, nanofibers, nanospheres, intermediate shapes, and other supramolecular structures are achieved by adjusting the identity of the PA component parts. In some embodiments, characteristics of supramolecular nanostructures of PAs are altered by post-assembly manipulation (e.g., heating/cooling, stretching, etc.).

In some embodiments, a peptide amphiphile comprises: (a) a hydrophobic tail comprising an alkyl chain of 8-24 carbons; (b) a structural peptide segment (e.g., comprising VVAA (SEQ ID NO: 8)); and (c) a charged segment (e.g., comprising EE, EEE, EEEE (SEQ ID NO: 11), etc.). In some embodiments, any PAs within the scope described herein, comprising the components described herein, or within the skill of one in the field, may find use herein.

In some embodiments, a targeting peptide amphiphile comprises (e.g., from C-terminus to N-terminus or from N-terminus to C-terminus): targeting moiety (e.g. ApoA1 mimetic peptide)—charged segment (e.g., comprising EE, EEE, EEEE (SEQ ID NO: 11), etc.)—structural peptide segment (e.g., $V_2A_2$ (SEQ ID NO: 8))—hydrophobic tail (e.g., comprising an alkyl chain of 8-24 carbons).

In some embodiments, a targeting peptide amphiphile comprises (e.g., from C-terminus to N-terminus or from N-terminus to C-terminus): targeting moiety (e.g. ApoA1 mimetic peptide)—linker (e.g. a single Glycine residue)—charged segment (e.g., comprising EE, EEE, EEEE (SEQ ID NO: 11), etc.)—structural peptide segment (e.g., $V_2A_2$ (SEQ ID NO: 8)) —hydrophobic tail (e.g., comprising an alkyl chain of 8-24 carbons).

In some embodiments, a therapeutic peptide amphiphile comprises (e.g., from C-terminus to N-terminus or from N-terminus to C-terminus): therapeutic agent (e.g. Ac2-26, GW3965) —charged segment (e.g., comprising EE, EEE, EEEE (SEQ ID NO: 11), etc.)—structural peptide segment (e.g., $V_2A_2$ (SEQ ID NO: 8))—hydrophobic tail (e.g., comprising an alkyl chain of 8-24 carbons).

In some embodiments, a peptide amphiphile comprises (e.g., from C-terminus to N-terminus or from N-terminus to C-terminus): therapeutic agent (e.g. Ac2-26, GW3965) —cleavable linker (e.g. ROS or MMP2/9 sensitive linker)—charged segment (e.g., comprising EE, EEE, EEEE (SEQ ID NO: 11), etc.)—structural peptide segment (e.g., $V_2A_2$ (SEQ ID NO: 8)) —hydrophobic tail (e.g., comprising an alkyl chain of 8-24 carbons).

In some embodiments, a PA further comprises an attachment segment or residue (e.g., K) for attachment of one or more segments of the PA to another segment. For example, the PA may further comprise a residue for attachment the hydrophobic tail to the peptide portion of the PA. In some embodiments, the hydrophobic tail is attached to a lysine side chain. In some embodiments, a PA further comprises an attachment segment or residue (e.g., K) for attachment of the therapeutic agent (e.g. LXR agonist) to the cleavable linker (e.g. ROS-sensitive linker, GSH-sensitive linker).

In some embodiments, a peptide amphiphile comprises (e.g., from C-terminus to N-terminus or from N-terminus to C-terminus): therapeutic agent (e.g. Ac2-26, GW3965) —attachment residue (e.g., K)—cleavable linker (e.g. ROS or MMP2/9 sensitive linker)—charged segment (e.g., comprising EE, EEE, EEEE (SEQ ID NO: 11), etc.)—structural peptide segment (e.g., $V_2A_2$ (SEQ ID NO: 8))—hydrophobic tail (e.g., comprising an alkyl chain of 8-24 carbons).

In some embodiments, provided herein are nanofibers and nanostructures assembled from any combination of the peptide amphiphiles described herein. In some embodiments, a nanofiber is prepared by the self-assembly of the PAs described herein. In some embodiments, a nanofiber comprises or consists of targeting PAs and/or therapeutic PAs. In some embodiments, in addition to targeting and/or therapeutic PAs, filler PAs (e.g. diluent PAs) are included in the nanofibers. In some embodiments, filler PAs are peptide amphiphiles, as described herein (e.g., structural peptide segment, charged segment, hydrophobic segment, etc.), but lacking a targeting moiety or a therapeutic agent. In some embodiments, filler peptides are basic or acidic peptides.

In some embodiments, the filler PAs and the targeting and/or therapeutic PAs self-assemble into a nanofiber comprising two or more types of PAs. For example, the filler PAs, targeting PAs, and therapeutic PAs may self-assemble into a nanofiber comprising each type of PA. For example, the nanofiber may comprise a targeting PA (e.g. ApoA1 targeting PA), a therapeutic PA (e.g. Ac2-26 PA, GW3965 PA), and one or more filler PAs. In some embodiments, the nanofiber comprises a therapeutic PA and one or more filler PAs.

In some embodiments, the nanofiber may comprise a targeting PA (e.g. ApoA1 targeting PA) and one or more filler PAs. The nanofiber may additionally contain a therapeutic agent, such as an LXR agonist. For example, the LXR agonist GW3965 may be encapsulated within a nanofiber containing the ApoA1 targeting PA and one or more filler PAs. In some embodiments, nanostructures (e.g., nanofibers) assembled from the peptide amphiphiles described herein are provided.

In some embodiments, filler peptides (e.g., basic peptide, acidic peptides, etc.) impart mechanical characteristics to a material comprising the PA nanofibers described herein. In some embodiments, a nanofiber assembled from 0-75% (mass %) therapeutic/targeting PA and 25-100% (mass %) basic filler PA becomes a gel at basic pH conditions (e.g., pH 8.5-11). In some embodiments, a nanofiber assembled from 75-100% (mass %) therapeutic/targeting PA and 0-25% (mass %) basic filler PA is a liquid at basic pH conditions (e.g., pH 8.5-11). In some embodiments, a nanofiber assembled from 0-20% (mass %) therapeutic/targeting PA and 80-100% (mass %) acidic filler PA becomes a gel at acidic pH conditions (e.g., pH 1-5). In some embodiments, a nanofiber assembled from 20-80% (mass %) therapeutic/targeting PA and 20-80% (mass %) acidic filler PA becomes a gel at neutral pH conditions (e.g., pH 5-8.5). In some embodiments, a nanofiber assembled from 80-100% (mass %) therapeutic/targeting PA and 0-20% (mass %) acidic filler PA is a liquid at acidic pH conditions (e.g., pH 1-5).

In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) targeting PAs. In particular embodiments, nanofibers comprise 40% targeting PAs (e.g. ApoA1-PAs). For example, nanofibers may comprise 40% targeting PAs and 60% filler PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) acidic filler PAs. In some embodiments, nanostructures (e.g., nanofibers) comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) basic filler PAs. In particular embodiments, nanofibers comprise 50% filler PAs. In some embodiments, nanofibers comprise 95%, 90%, 85%, 80%, 75%, 70%, 65%, 60%, 55%, 50% 45%, 40%, 35%, 30%, 25%, 20%, 15%, 10%, 5%, 4%, 3%, 2%, or 1% (or any ranges there between) therapeutic PAs. In particular embodiments, nanofibers comprise 10% therapeutic PAs. In some embodiments, nanofibers comprise 30-50% targeting PAs, 40-60% filler PAs, and 1-20% therapeutic PAs. For example, nanofibers may comprise 35-45% targeting PAs, 45-55% filler PAs, and 5-15% therapeutic PAs. For example, nanofibers may comprise 40% targeting PAs (e.g. ApoA1-PAs), 50% filler PAs, and 10% therapeutic PAs (e.g. Ac2-26 PAs, GW3965-PAs).

In some embodiments, the ratio of therapeutic and/or targeting PAs to acidic and/or basic PAs in a nanofiber determines the mechanical characteristics (e.g., liquid or gel) of the nanofiber material and under what conditions the material will adopt various characteristics (e.g., gelling upon exposure to physiologic conditions, liquifying upon exposure to physiologic conditions, etc.).

Peptide amphiphile (PA) nanofiber solutions may comprise any suitable combination of PAs. In some embodiments, at least 0.05 mg/mL (e.g., 0.10 mg/ml, 0.15 mg/ml, 0.20 mg/ml, 0.25 mg/ml, 0.30 mg/ml, 0.35 mg/ml, 0.40 mg/ml, 0.45 mg/ml, 0.50 mg/ml, 0.60 mg/ml, 0.70 mg/ml, 0.80 mg/ml, 0.90 mg/ml, 1.0 mg/ml, or more, or ranges therebetween), of the solution is a filler PA. In some embodiments, at least 0.25 mg/mL of the solution is a filler PA. In some embodiments, a filler PA is a PA molecule having highly charged glutamic acid residues on the terminal end of the molecule (e.g., surface-displayed end). These negatively charged PAs allow for the gelation to take place between nanofibers via ionic crosslinks. In some embodiments, a filler PA is a PA molecule having highly charged lysine residues on the terminal end of the molecule (e.g., surface-displayed end). These positively charged PAs allow for the gelation to take place under basic conditions. The filler PAs provide the ability to incorporate other PAs molecules (e.g. therapeutic PAs, targeting PAs) into the nanofiber matrix while still ensuring the ability of the nanofibers solution to gel. In some embodiments, the solutions are annealed for increased viscosity and stronger gel mechanics. These filler PAs have sequences are described in, for example, U.S. Pat. No. 8,772,228 (e.g., $C_{16}$-VVVAAAEEE (SEQ ID NO: 12), e.g., $C_{16}$-VVAAEE (SEQ ID NO: 13)), which is herein incorporated by reference in its entirety.

In some embodiments, the PA nanofiber described herein exhibit a small cross-sectional diameter (e.g., <25 nm, <20 nm, <15 nm, about 10 nm, etc.). In some embodiments, the small cross-section of the nanofibers (~10 nm diameter) allows the fibers to permeate the brain parenchyma.

In some embodiments, the PAs and nanofibers described herein may be incorporated into pharmaceutical compositions for use in methods of treating disease. For example, the PAs and nanofibers described herein may be used for methods of treatment or prevention of atherosclerosis in a subject. The composition may be administered in any suitable amount, depending on factors including the age of the subject, weight of the subject, severity of the injury, and the like. The composition may be administered in combination with other suitable treatments for injury or preventative measures to prevent the severity of the injury from worsening.

In some embodiments, the PA and nanofiber compositions herein are formulated for delivery to a subject. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration. In some embodiments, the PA compositions are administered parenterally. In some embodiments, parenteral administration is by intrathecal administration, intracerebroventricular administration, or intraparenchymal administration. The PA compositions herein can be administered as the sole active agent or in combination with other pharmaceutical agents such as other agents used in the treatment of nervous system injury in a subject.

EXAMPLES

Example 1

LXR Agonist

Methods:

PA Synthesis and Purification: Peptide amphiphile molecules were synthesized using 9-fluorenyl methoxycarbonyl (Fmoc) solid-phase peptide chemistry with low-loading Rink amide 4 methylbenzhydrylamine resin (EMD Millipore) for the ApoA1 PA ($C_{16}$-$V_2A_2$ (SEQ ID NO: 8)-$E_2$-G-DWFKAFYDKVAEKFKEAF (SEQ ID NO: 2)-NH2) and scrambled ApoA1 PA ($C_{16}$-$V_2A_2$ (SEQ ID NO: 8)-$E_2$-CDWFAKDYFKKAFVEEFAK (SEQ ID NO: 9)-NH2). Rink amide MBHA resin was used for the non-targeting PA (sequence: $C_{16}$-$V_2A_2$ (SEQ ID NO: 8)-$E_2$-NH2). PA synthesis was performed on the CEM Liberty automated microwave peptide synthesizer. Each amino acid and palmitic acid ($C_{16}$) coupling proceeded as follows: after removal of Fmoc groups with 30% 4-methylpiperidine and 0.1 µM hydroxybenzotriazole (HOBt) in N,N-dimethylformamide (DMF) at 75° C. for 3-4 min, of protected amino acid or palmitic acid (4 eq), O-benzotriazole-N, N, N', N'-tetramethyluronium hexafluorophosphate (HBTU, 4 eq) and N,N-diisopropylethylamine (DIEA, 8 eq) were added to the resin and coupled at 75° C. for 5-10 min.

After synthesis, PAs were cleaved off the resin in a 95:2.5:2.5 trifluoroacetic acid (TFA)/triisopropylsilane (TIPS)/H2O mixture for 2-3 hours. Rotary evaporation and precipitation in cold diethyl ether yielded the crude product. Crude PAs were purified by HPLC on a C18 Phenomenex Gemini column in a water-acetonitrile gradient containing 0.1% v/v NH4OH. Pure fractions were collected and identified using ESI-MS. The combined fractions were subjected to rotary evaporation to remove volatile solvents, frozen in liquid nitrogen, and lyophilized to dryness. Purity (>95%) was verified using LC-MS or analytical HPLC or both. Fluorescently-labelled PAs were synthesized by reacting Alexa Fluor 546-$C_5$-maleimide with a 2- to 3-fold molar excess of ApoA1-C PA (ApoA1 PA containing a single cysteine residue in place of the glycine residue) or the corresponding scrambled PA. After reaction, the mixture was lyophilized and purified as described above to remove unreacted PA. The fluorescently-labelled PA was co-assembled with non-labelled PA at 10 wt % Alexa-PA, with the overall molar concentration of ApoA1 PA or scrambled ApoA1 PA kept at 40%, as described below. Preparation of PA Co-Assemblies and PA-LXR Encapsulations: PA co-assemblies and LXR-PA encapsulations were prepared using a solvent-evaporation method. Briefly, stock solutions of each PA and LXR agonist (GW3965 hydrochloride, used without further purification from *Aurum* Pharmatech) were prepared in 1,1,1,3,3,3-hexafluoro-2-propanol (HFIP) and mixed in pre-determined ratios corresponding to 40 mol % ApoA1 PA (or scrambled ApoA1 PA) and 60 mol % $V_2A_2$ (SEQ ID NO: 8)-$E_2$ PA for the PA co-assemblies. For the LXR-PA encapsulations, LXR agonist was added to the PA co-assembly in a 1:1 weight ratio of LXR/PA. The resulting solutions were transferred to microcentrifuge tubes and sonicated in a water bath for 15 minutes, frozen in liquid nitrogen, and placed under vacuum for 2 hours or until dry. The samples were then reconstituted in ultrapure water and pH-adjusted with 200 mM NaOH (final pH=7.5-8.0). Solutions were then subjected to two cycles of probe sonication (10% amplitude, 10 seconds/cycle), frozen in liquid nitrogen, and lyophilized to dry powder.

The chemical structure of GW3965 is shown below:
The chemical structure of GW3965 is shown below:

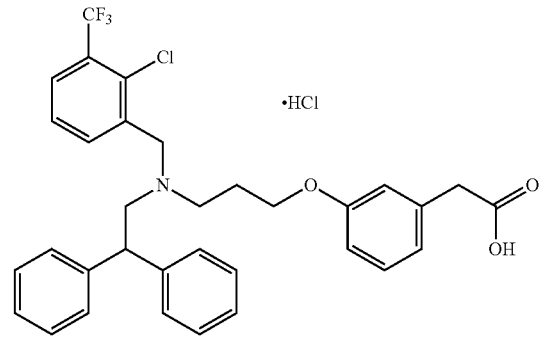 [SMILES: O=C(O)Cc1cccc(OCCCN(Cc2cccc(C(F)(F)F)c2Cl)CC(c2ccccc2)c2ccccc2)c1 ; Cl]

Materials Characterization: Both room-temperature TEM and cryo-TEM were performed using a JEOL 1230 TEM fitted with a $LaB_6$ filament working at an accelerating voltage of 80-100 kV. Images were acquired with a Gatan 832 CCD camera. Room-temperature TEM samples were drop-casted, blotted, and stained with a 2% uranyl acetate solution. Cryo-TEM samples were plunged into liquid ethane using a Vitrobot Mark IV (FEI) operating at 22° C. with 100% humidity. After vitrification, the sample was transferred under liquid nitrogen to a Gatan 626 cryo-holder. All PA samples were imaged at 1 mM in water for room-temperature TEM or phosphate-buffered saline (PBS) for cryo-TEM unless otherwise noted.

Circular dichroism measurements were performed using a Jasco J-815 CD spectrophotometer (PA and LXR-PA samples) or Chirascan®-plus (Applied Photophysics) spectrophotometer (4F peptide sample) at room temperature using a 0.1 mm path length demountable quartz cuvette. Data was averaged over three scans for each sample. PA and LXR-PA solutions were prepared at 500 µM (with respect to PA) in PBS. CD signal from the corresponding buffer blank was subtracted from each sample spectrum.

Fluorescence measurements were performed on an ISS PC1 fluorimeter. The excitation wavelength was set to 295 nm with an emission sweep from 325-400 nm. PA (0.1 mg/mL) and LXR-PA (0.1 mg/mL with respect to each component) samples were dissolved directly in PBS, and PBS background signal was subtracted from each spectrum. Absorbance readings were taken from 280-350 nm in 10 nm increments on an M5 Spectramax Plate Reader (Molecular Devices). Concentrations of PA and LXR-PA were 0.5 mg/mL with respect to PA. The absorbance of PBS was subtracted as background signal.

In Vitro Cholesterol Efflux Assay: J774.2 mouse macrophages (Sigma-Aldrich [ECACC]) were grown in DMEM supplemented with 10% fetal bovine serum (FBS), L-glutamine (2 mM), penicillin (100 U/ml), and streptomycin (100 μg/ml). Cells were plated at a density of 100,000 cells/well in 48-well plates and allowed to grow for 24 hours. Cells were then incubated for 24 hours in culture medium containing 10 μM NBD-cholesterol (Life Technologies), diluted from a 2.5 mM ethanolic stock (0.4% final ethanol concentration), and 2 μg/ml ACAT inhibitor (Sandoz 58-035, Sigma-Aldrich), diluted from a 10 mg/ml stock in dimethylsulfoxide (DMSO). ACAT inhibitor was present at the same concentration throughout the remainder of the experiment; its use was to prevent esterification of NBD-cholesterol which could confound cholesterol efflux calculations. After the labelling period, cells were washed twice in serum-free medium, and then incubated for 18 hours with 0.2% essentially fatty-acid free BSA (Sigma-Aldrich) in medium containing 2.5% FBS. PA, PA-LXR, LXR, and peptide solutions were prepared inside a sterile cell culture hood for this experiment as well as for the viability experiment described in the next section. Cells in treatment wells were washed with serum-free medium. Cells in reference wells (time 0) were washed twice with cold PBS and lysed in cold RIPA buffer (200 μl/well, Life Technologies) for 10-15 minutes at 4° C. Lysates were centrifuged at 4° C. for 15 minutes at 16,000×g, after which 100 μl of supernatant was carefully transferred to a 96-well plate for fluorescence measurement, taking care to avoid transferring any cellular debris. Meanwhile, treatments diluted in serum-free medium were added to cells in treatment wells and incubated for t=1 or 4 hours. LXR agonist GW3965 (LXR) was sonicated to assist solubility in PBS using a Q700 Sonicator (QSonica) at 20 amplitude with two, 10 s pulse cycles. The 4F peptide, LXR, and diluent PA were added to match the concentration of the peptide in LXR-40% ApoA1 PA (11.2, 20, and 5.8 μg/mL, respectively). At each time point, treatment solutions were collected, centrifuged at room temperature for 2 minutes at 100×g to pellet floating cells, and 100 μl of supernatant transferred to a 96-well plate for fluorescence measurement. Simultaneously, cells were washed twice with cold PBS and lysed following the procedure used for the reference wells. Fluorescence intensities of both treatment solutions and corresponding cell lysates were read on the Cytation 3 Multi-Mode Reader (BioTek, Winooski, VT), with excitation set at 473 nm and emission at 530 nm. Percent cholesterol efflux for each treatment was calculated as follows:

$$\% \text{ cholesterol efflux} = \frac{F \cdot I_{t0} - F \cdot I_{tx}}{F \cdot I_{t0}} \times 100\%$$

where F.I.$_{t0}$ is the average fluorescence intensity of cell lysates at time 0 across triplicate wells, and F.L.$_{tx}$ is the average fluorescence intensity of cell lysates at the designated timepoint (x=1 or 4 h) across triplicate wells. Fluorescence intensities of treatment solutions were also measured to ensure corroboration with results from the cell lysates, but were not analyzed quantitatively. MUSE™ Count and Viability Assay: Cell viability experiments were performed with a MUSE™ Count and Viability kit (Millipore) which discriminates between live and dead cells by their permeability to fluorescent, DNA-binding dyes. The cells are analyzed by the MUSE Count & Viability Software Module that generates dot plots to gate and analyze cell size against fluorescence. J774.2 macrophages, cultured and treated under identical conditions as the cholesterol assay, were collected after four hours of treatment by rinsing with PBS and the addition of Accutase™ (STEMCELL™ Technologies) for 15 minutes at 37° C. The cells were diluted 1:2 in MUSE™ Count & Viability Reagent and allowed to mix for five minutes before analysis. A minimum of 1000 cells were analyzed per condition.

Dialysis: LXR agonist release studies were performed using 2K MWCO Slide-A-Lyzer™ MINI Dialysis cups (Life Technologies), which have dialysis membrane-bottoms and are submerged in the solution against which the sample is dialyzed. LXR-40% ApoA1 PA (1 mM with respect to PA) was dissolved in PBS. The LXR agonist without PA was insoluble in deionized water or PBS, so it was dissolved in pH 10 H$_2$O and diluted to the final concentration in PBS (final pH 8.0-8.5) to obtain a working solution. To each dialysis cup 0.1 mL of sample was added with one cup used for each time-point to be measured. All samples were dialyzed against 4 mL of PBS at 37° C. The total contents of one dialysis cup were isolated and kept at 4° C. until measurement at each time point. LXR agonist remaining at each time-point was therefore determined by LC-MS analysis of the contents of the dialysis device as follows: LC-MS was performed on an Agilent 6520 Q-TOF LCMS, using a Phenomenex Gemini C18 analytical column. For LC-MS, a 5 to 95% acetonitrile (0.1% formic acid) gradient was run over 30 min with mobile phase containing 0.1% NH4OH. A total ion chromatogram was obtained in MS mode and integrated using Mass Hunter Agilent software. The peak area corresponding to [M-H]− for GW3965 was recorded for each sample in negative ion mode and normalized according to the volume of sample present. Percent encapsulation was determined as follows:

$$\% \text{ LXR agonist encapsulation} = \frac{NPA_{supernatant}}{NPA_{supernatant} + NPA_{pellet}} \times 100\%$$

where NPA is the normalized peak area corresponding to LXR agonist (normalized for solution volume).

Mouse Model of Atherosclerosis and In Vivo Proof of Concept: LDLR-KO mice were fed a high fat "Western" diet (Teklad TD.88137) starting at 4 weeks of age. This diet consisted of 20% fat, 0.2% cholesterol, and 34% high sucrose. LDLR-KO mice fed this diet typically develop severe hypercholesterolemia (>800 mg/dL) and hypertriglyceridemia (>300 mg/dL) after only 2 weeks, and by 12 weeks on the high fat diet, atherosclerotic lesions are detected in the aortic root and aortic arch. After 14 weeks on the high fat diet, mice received intravenous injections of PA nanofibers dissolved in PBS (dorsal penile vein in males) under sterile conditions. Mice were briefly anesthetized for injection with inhaled isoflurane. After injection, mice were monitored and allowed to recover from anesthesia in a heated oxygen chamber. Mice were sacrificed and euthanized under anesthesia by diaphragm disruption and exsanguination. Phlebotomy was performed through direct right ventricular cardiac puncture. Perfusion was performed through left ventricular cardiac puncture with PBS (10 cc) and 10% sucrose (10 cc). The heart and aortic roots were then flash frozen in Optimal Cutting Temperature embedding medium 4583 (Tissue-Tek®) with liquid nitrogen. Frozen specimens were cryosectioned at 8 μm through the aortic root as described by Baglione and Smith. Aortic root sections in which all three aortic valve leaflets were visible were used for analysis. Fluorescent microscopy was performed on unstained sections to identify the presence of PA nanofibers. Fluorescent histology imaging was performed with a Zeiss LSM-510 microscope (Hallbergmoos, Germany) with a 5× objective. PA fluorescence was assessed with the HE CY3 filter (Zeiss filter #43) using excitation and emission wavelengths of 550-575 nm and 605-670 nm, respectively. Nuclear staining was performed with DAPI (4',6-Diamidino-2-Phenylindole, Dilactate, ThermoFisher, Chicago, IL), and assessed with the DAPI filter (Zeiss filter #49) using excitation and emission wavelengths of 365-395 and 445-450 nm, respectively. Tissue autofluorescence was assessed with the green fluorescent protein filter (Zeiss filter #38) using excitation and emission wavelengths of 470-495 and 525-550 nm, respectively. The development of atherosclerosis within LDLR KO mice was confirmed by quantifying the percentage of aortic root area that contained lipid droplets using Oil Red O staining with ImageJ software. Aortic root sections of wild type C57/Bl6 mice were quantified as a control. PA binding to the aortic root was quantified by converting the images to RGB and quantifying the red channel. All protocols for the animal model and procedures were approved by the Institutions Animal Care and Use Committee.

Statistical Analysis: Data (efflux and viability assays) was analyzed from three independent experiments performed in triplicate with one or two factor ANOVA followed by a post-hoc Student's t-test (JMP® Pro 13 software). The data is presented as mean±SEM and significance was assessed using $*p<0.05$.

Results:

The targeting PA (ApoA1 PA) molecule was designed with a C16 aliphatic tail, the β-sheet-forming sequence $V_2A_2$ (SEQ ID NO: 8), negatively charged $E_2$ amino acid residues, a single glycine residue as a spacer, and the 4F ApoA1 mimetic sequence (DWFKAFYDKVAEKFKEAF (SEQ ID NO: 2)-$NH_2$) displayed as the epitope (FIG. 1A). The two glutamic acid residues were incorporated to render overall negative charge to the PA, since negatively charged particles are typically more soluble in physiologic solutions and are more likely to be taken up by macrophages. Furthermore, PA supramolecular nanostructures with high positive charge may be cytotoxic, a phenomenon commonly reported with positively charged nanoparticles.

The 4F peptide was developed by the Segrest and Ananthamaraiah research groups as a variant of a parent peptide 18A (Datta et al., J. Lipid Res. 2001, 42, 1096), a synthetic structural mimetic of apolipoprotein α-helices. These α-helices promote high affinity binding of lipids —especially oxidized lipids—to the 4F peptide sequence. Since oxidative modification of LDL has been shown to correlate with atherosclerotic severity, high affinity binding to oxidized lipids could offer a valuable targeting strategy. Hence, the ApoA1 PA was developed as a platform to use oxidized-lipid binding to selectively target atherosclerotic plaques.

Figure 2A:
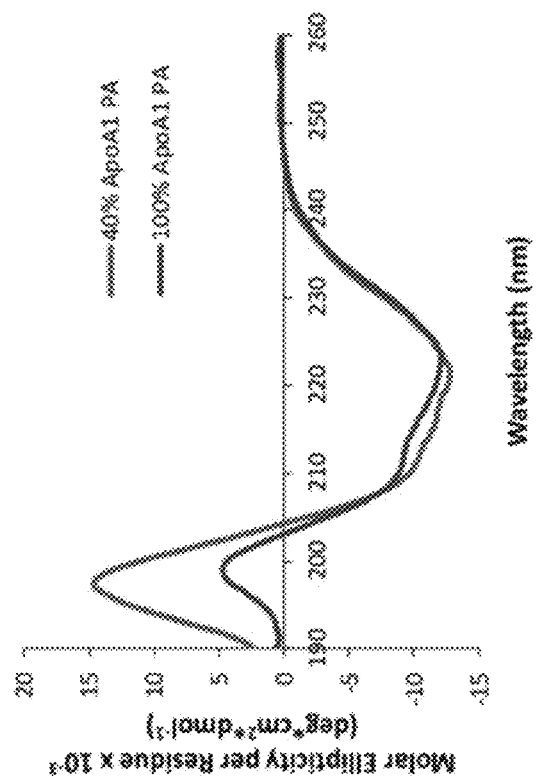
FIG. 2A shows CD spectra of 40% and 100% ApoA1 PA.

The ApoA1 PA alone did not form nanofibers, but instead formed aggregated mesh-like networks (FIG. 1). It was therefore coassembled with a diluent PA ($C_{16}$-$V_2A_2$ (SEQ ID NO: 8)-E2-$NH_2$) that on its own self-assembles into long nanofibers. Coassembly was achieved by mixing solutions of the component PAs in HFIP (1,1,1,3,3,3-hexafluoro-2-propanol), a peptide-disaggregating solvent later removed by evaporation. After coassembly, nanofibers were observed by cryogenic-transmission electron microscopy (cryo-TEM) (FIG. 1C). From a series of coassembled structures characterized by TEM, the 40 mol % coassembly with diluent PA incorporated the highest epitope concentration without compromising the fiber morphology. The PA nanofibers' high aspect ratio makes their exact lengths difficult to determine. However, the presence of fiber ends visible indicates their discrete nature. While the fibers in this image tend to exceed 1 μm in length, other images taken show individual fibers with shorter end-to-end lengths on the order of 300 nm. Circular dichroism (CD) measurements confirmed that the 4F targeting peptide displayed on the ApoA1 PA maintained the expected α-helical conformation (FIG. 2A) upon nanofiber assembly (FIG. 2B).

Figures 3A, 3B, 3C:
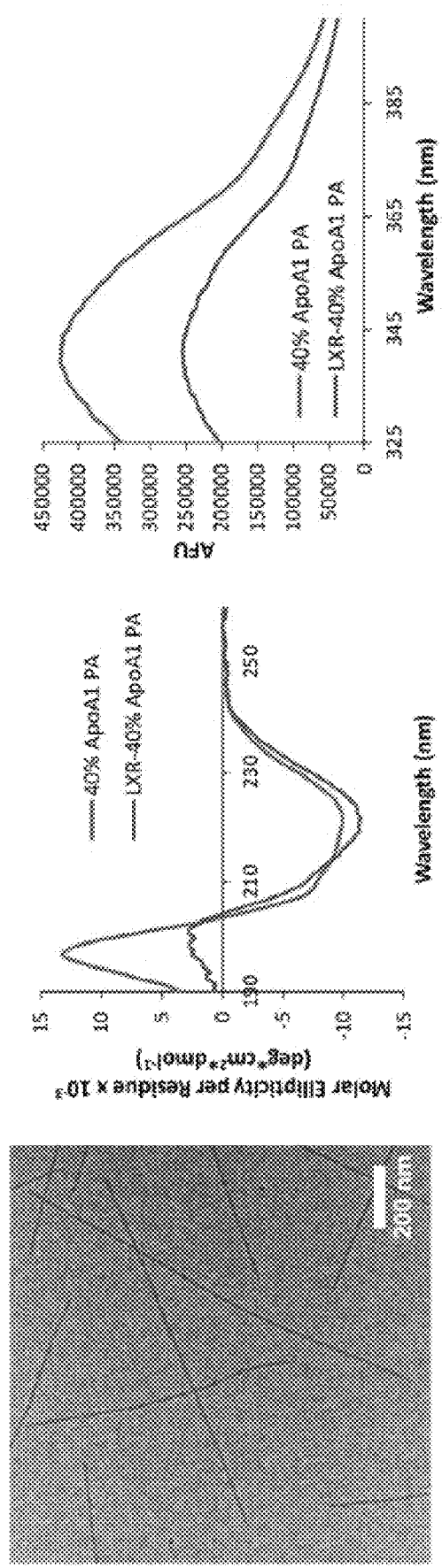

HFIP was also used to dissolve and encapsulate the LXR agonist GW3965. Since HFIP is highly volatile and each sample was placed under vacuum twice, any residual HFIP would have been negligible in the final PA or PA samples containing encapsulated drug. Addition of base was required for solubilizing the PA coassembly itself, and since the LXR agonist was supplied as a hydrochloride salt, excess sodium hydroxide was added to neutralize the acid. Upon addition of this excess base to pH 7.5, 40% ApoA1 PA encapsulated LXR agonist in a 1:1 weight ratio (the encapsulation will be referred to as LXR-40% ApoA1 PA). Encapsulation did not impact the ability of the PA to form nanofibers (FIG. 3A). CD measurements on the encapsulation showed that the presence of LXR agonist diminished the overall intensity of the CD signal compared with that of PA alone and somewhat reduced the α-helicity of the PA (FIG. 3B), suggesting a slight conformational change upon binding. As discussed below, the drug-free and drug-containing PA nanostructures showed similar plaque-binding efficacy in vivo. However, in this context one cannot discount the possibility that conformational changes occur upon lipid binding in vivo, something which is at this time very difficult to establish experimentally.

Figure 4:
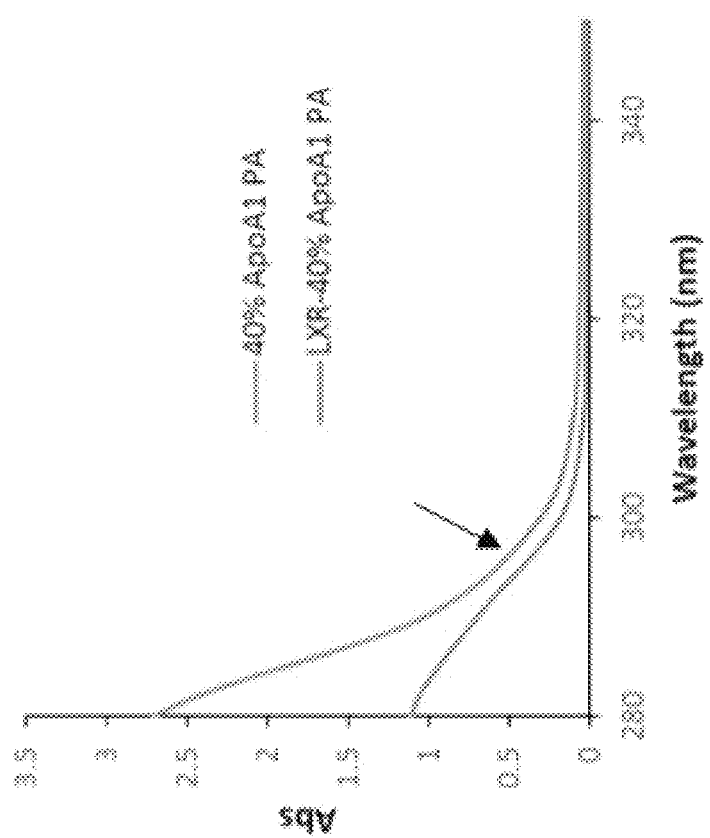
FIG. 4 shows absorbance was measured from 280 nm-350 nm for 40% ApoA1 PA and LXR-40% ApoA1 PA, with absorbance of PBS subtracted from the raw data. By 295 nm (arrow), differences in absorbance between the two are slight.

Since the ApoA1 mimetic peptide contains a tryptophan residue near its N-terminus, and tryptophan is a highly sensitive solvatochromic fluorophore, we compared the fluorescence emission spectra of 40% ApoA1 PA in the absence and presence of the LXR agonist to determine if its interaction with the PA would result in a change to the emission profile. LXR agonist encapsulation resulted in tryptophan fluorescence quenching (FIG. 3C), but did not shift the λ max of emission (338 nm) as typically occurs when tryptophan solvent exposure changes. Tryptophan quenching is commonly used to study ligand-protein interactions, with quenching occurring due to the inner filter effect (significant absorption at the excitation wavelength), collisional quenching, or ligand binding. Absorption values at the excitation wavelength used in this work (295 nm for exclusive excitation of tryptophan residues over tyrosine residues) were almost identical between 40% ApoA1 PA and LXR-40% ApoA1 PA (FIG. 4), which means inner filter effects were not contributing significantly to the observed quenching. Hence, collisional quenching or binding-associated interactions, or both, were likely occurring, indicating close interactions between the PA and LXR agonist. Together the CD and fluorescence results suggest that the LXR agonist interacts closely with the α-helices presented on the PA nanofibers. The peptide epitopes are amphiphilic and each has a nonpolar face consisting of most of the peptide's hydrophobic residues; it is therefore likely that the encapsulation of LXR agonist, a molecule with very low water-solubility, is stabilized by hydrophobic interactions between the agonist and peptide nonpolar residues. Another possible stabilizing interaction is that of pi-pi stacking between the agonist's aromatic rings and the aromatic side chains on the PA molecules.

Since cholesterol efflux is a key step in reverse cholesterol transport, the in vitro efflux activity of PA-encapsulated LXR agonist was examined. J774.2 mouse macrophages were loaded with the fluorescent cholesterol analogue 22-(N-(7-nitrobenz-2-oxa-1,3-diazol-4-yl)amino)-23,24-bisnor-5-cholen-3 β-ol (NBD)-cholesterol for 24 h, equilibrated for 18 h with 0.2% bovine serum albumin, and then treated with each condition in triplicate for t=1 or 4 h. This was performed in serum-free Dulbecco's modified eagle's medium (DMEM) culture medium to avoid confounding affects with the lipoproteins present in serum, which could also enhance efflux. After 1 h, none of the treatment conditions resulted in significantly different cholesterol efflux compared with the DMEM culture medium control (FIG. 3D). However, after 4 h cholesterol efflux was significantly higher in macrophages treated with LXR-40% ApoA1 PA in comparison to DMEM (p=0.0127), 4F (p=0.0142), 40% ApoA1 PA (p=0.0154), diluent PA (p=0.0007), and LXR at 20 µg mL-1 (p=0.0171). The effects of two- and threefold higher concentrations of LXR were also examined, but no significant increases in LXR effects upon macrophage efflux were seen (data not shown). These results may be due to limits in LXR solubility within the culture media as the LXR-40% ApoA1 PA at similar concentrations did not show solubility issues and demonstrated a therapeutic effect. In order to analyze the effect of each treatment on cell viability, a MUSE Count and Viability experiment was performed (FIG. 3E). Although treatment with the LXR-40% ApoA1 PA coassembly significantly decreased cell viability in comparison to DMEM (p=0.0010), 4F (p<0.0001), ApoA1 PA (p=0.0002), and diluent PA (p=0.0019), there was not a significant difference in comparison to treatment with LXR agonist alone (p=0.3785). It has been found that LXR agonists reduce cell viability in some cell lines, particularly at higher concentrations (e.g., 20×10-6 m; we used a concentration of 20 µg mL-1 or ~32×10-6 m), whereas when used at lower concentrations (e.g., 1×10-6 m) viability is not affected, suggesting that the observed toxicity may be due to the higher concentration of LXR agonist used in the treatments.

Figure 5:
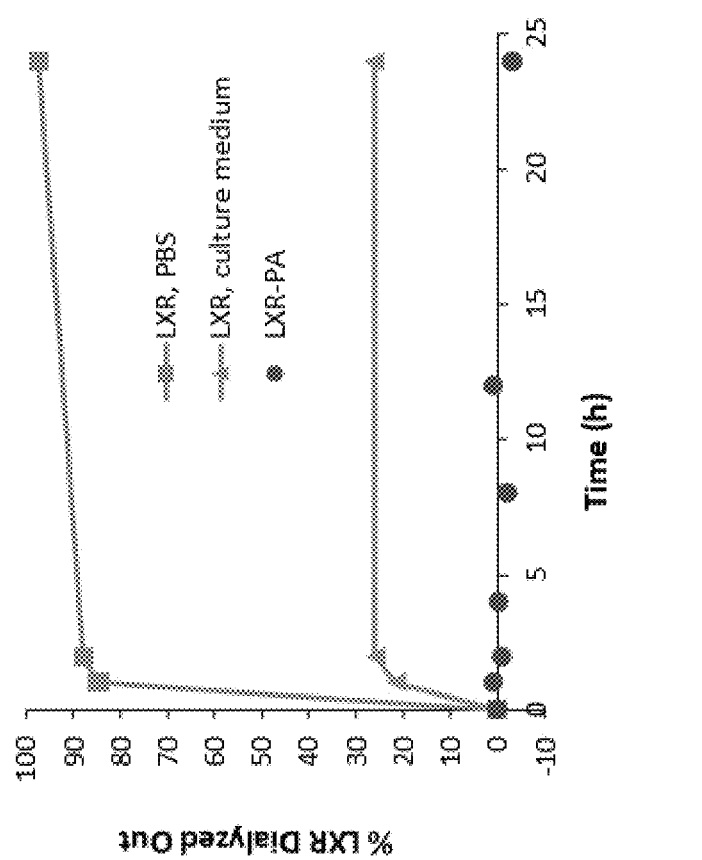
FIG. 5 shows dialysis with LXR agonist alone showed rapid release across the membrane up to 85% within the first hour in PBS. However, in culture medium with protein/lipoprotein-containing serum (DMEM+10% FBS), release was slower and did not exceed 26% after 24 h.

Dialysis experiments with LXR-40% ApoA1 in phosphate buffered saline (PBS) at 37° C. yielded no release of drug from the dialysis chamber over 24 h (FIG. 5). No release was observed for up to 1 week in PBS (pH 7.4) at room temperature either. However, dialysis with non-encapsulated LXR agonist in PBS with excess base (final pH 8-8.5; necessary for dissolution) showed rapid release over first hour, confirming that GW3965 alone was capable of crossing the dialysis membrane (FIG. 5). Cholesterol efflux suggested that macrophages were able to access LXR agonist. The drug molecule may be too hydrophobic to diffuse passively out of the PA nanofiber in PBS, but in the presence of lipid-binding proteins in the cell under physiologic conditions, it may be induced to leave the nanofiber. To investigate this possibility, dialysis with non-encapsulated LXR agonist was repeated in serum-containing culture medium, as serum contains lipoproteins, albumin, and other potential lipid-carriers, and binding between the drug molecule and proteins would prevent LXR agonist from crossing the dialysis membrane. Compared with dialysis in PBS, dialysis in culture medium resulted in both slower initial release and greatly reduced overall release over 24 h (FIG. 5), suggesting binding between LXR agonist and culture medium components. Since "release" of non-encapsulated LXR agonist across the membrane appears to plateau at around 25%, this reduced amount of drug may be enough to enhance efflux. It is also possible that other yet-to-be-discovered mechanisms are responsible for the efficacy of LXR-40% ApoA1 PA in macrophage cholesterol efflux. The dialysis set-up with PA-containing samples does not mimic the in vivo situation in which proteins and protein-lipid complexes are present. However, due to the nature of the measurements (i.e., analysis of remaining sample post-dialysis via liquid chromatography-mass spectrometry), including such complexes would confound the ability to measure the remaining quantity of PA or drug, as their associated m/z peaks could overlap. Regardless, the lack of LXR agonist crossing the dialysis membrane in the LXR-40% ApoA1 PA experiment also provides further confirmation of encapsulation of the drug molecule, since the experiments performed with LXR agonist alone show that any non-encapsulated drug crosses the dialysis membrane readily.

Figure 6D:
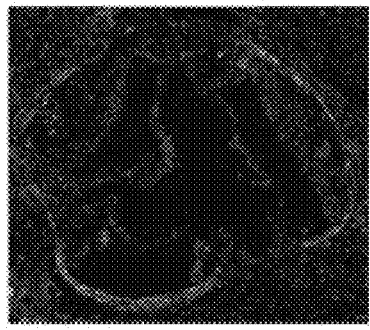
Figure 6E:
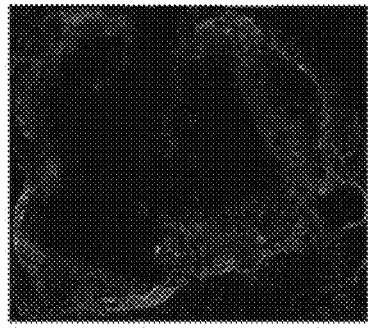
Figure 6F:
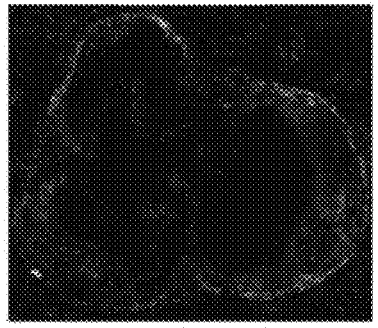
Figure 6G:
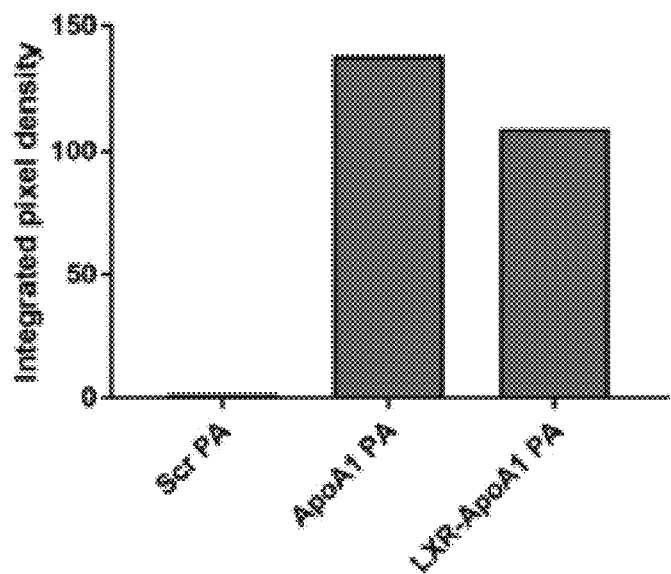

After in vitro characterization of the PA nanofiber, in vivo proof of concept studies in a murine model were performed. The LDLR KO mouse was used for experiments rather than the apolipoprotein E (ApoE) KO one because the former model more closely resembles a known human condition (familial hypercholesterolemia) compared to the latter which does not emulate a human disease. Wild type C57/B16 mice do not develop atherosclerosis on regular chow and LDLR KO mice fed a high fat diet develop atherosclerosis in the aortic root (FIG. 6A, 6B). Quantification of Oil Red O staining shows that $\sim_{45}$% of the aortic root area in the high fat diet-LDLR KO model contained lipid droplets, while less than 1% did in the C57/B16 fed regular chow (FIG. 6C). LDLR KO mice fed the high fat diet for 14 weeks were administered ApoA1 PA and LXR-40% ApoA1 PA intravenously. Nanofiber solutions were prepared under sterile conditions and injected using surgical techniques. Fluorescent microscopy revealed localization of the nanofibers to areas of atherosclerotic plaque in the aortic root 24 h after injection. Therefore, 40% ApoA1 PA may be a viable delivery vehicle for in vivo targeted therapy. Furthermore, addition of the LXR agonist GW3965 does not compromise the delivery vehicle's ability to target atherosclerosis (FIG. 6E, 6F). As a nontargeting control, scrambled ApoA1 PA was designed with identical composition to ApoA1 PA, but displaying a nonhelical scrambled 4F sequence. Intravenous injection of scrambled ApoA1 PA does not reveal evidence of nanofiber localization at areas of atherosclerosis 24 h after intravenous injection in atherosclerotic LDLR KO mice fed the high fat diet for 14 weeks (FIG. 6D; quantification of PA binding in FIG. 6D-6F shown in FIG. 6G). Due to the marginalization to the periphery of the vascular lumen conferred by the targeting peptide sequence and nanofiber shape, this serves as a promising platform for in vivo drug delivery and therapy for atherosclerosis in humans.

In conclusion, the present disclosure demonstrates the synthesis and characterization of a targeting PA nanofiber-based drug delivery vehicle that is injected intravenously and reaches atherosclerotic sites with high specificity. The nanofiber morphology and multivalent presentation of ApoA1-mimetic peptides combine to offer a robust plaque-targeting strategy. Hence, results from the in vitro structural characterization and study on cholesterol efflux from macrophages, together with in vivo targeting of atherosclerotic plaques, all support this PA nanofiber as a promising vehicle for drug delivery and targeted therapy for atherosclerosis.

Example 2

Ac2-26—Tethered PAs

Materials and Methods

PA Synthesis: All PAs were synthesized using standard 9-fluorenyl methoxycarbonyl chemistry with Rink Amide 4-methylbenzhydrylamine resin and contained a C-terminal amide to improve stability. E2 filler PA, or the PA backbone, consists of palmitoyl ($C_{16}$) attached to $V_2A_2$ (SEQ ID NO:

8)-$E_2$. ROS-Ac2-26 PAs incorporated Ac2-26 (AMVSE-FLKQAWFIENEEQEYVQTVK, SEQ ID NO: 7) to the PA backbone via five prolines, and additional lysine residues to enhance solubility ($C_{16}$-$V_2A_2$ (SEQ ID NO: 8)-$E_2$-$KP_5K$ (SEQ ID NO: 10)-AMVSEFLKQAWFIENEEQEYVQTVK SEQ ID NO: 7-$NH_2$). The structure of the $KP_5K$ (SEQ ID NO: 10) linker is shown below:

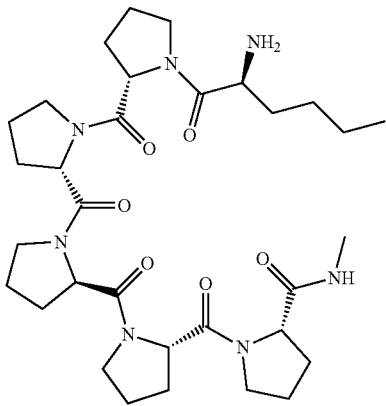 [SMILES: CCCC[C@H](N)C(=O)N1CCC[C@H]1C(=O)N1CCC[C@H]1C(=O)N1CCC[C@@H]1C(=O)N1CCC[C@H]1C(=O)N1CCC[C@H]1C(=O)NC]

The MMP-Ac2-26 PAs contained Ac2-26 attached to backbone PA via the MMP2/9-sensitive PQ peptide (GGGPQGIWGQGK, SEQ ID NO: 1) to generate $C_{16}$-$V_2A_2$ (SEQ ID NO: 8)-$E_2$-GGGPQGIWGQGK (SEQ ID NO: 1)-AMVSEFLKQAWFIENEEQEYVQTVK (SEQ ID NO: 7)-$NH_2$. ApoA1 PAs contained the 4F peptide attached to backbone PA through a glycine linkage ($C_{16}$-$V_2A_2$ (SEQ ID NO: 8)-$E_2$-G-DWFKAFYDKVAEKFKEAF (SEQ ID NO: 2)-$NH_2$). To visualize PA cellular uptake and localization, $E_2$ filler PAs were synthesized to contain a fluorescent molecule, Alexa Fluor 546-C5-maleimide, attached by reaction with a cysteine thiol residue ($C_{16}$-$V_2A_2$ (SEQ ID NO: 8)-$E_2$-C) and reacted with 2- to 3-fold molar excess PA. All PAs were purified by high performance liquid chromatography (HPLC), and characterized by LC-MS.

APoA1-Ac2-26 PA co-assembly: ApoA1-Ac2-26 PAs were co-assembled from ApoA1 PA, E2 filler PA, and ROS- or MMP-Ac2-26 PAs at varying molar ratios, and dissolved in 1,1,1,3,3,3-hexafluoro-2-propanol (HFIP, Sigma-Aldrich) at 2 mg/mL before probe sonication with a Q700 Sonicator (Qsonica, 10% amplitude, 110 V, 20 kHz) in a water bath for 15 minutes. ApoA1 PA controls were co-assembled using 40 mol % ApoA1 PA and 60 mol % E2 filler PA dissolved in HFIP and mixed with a probe sonicator for five minutes. The resulting PA co-assemblies were frozen in liquid nitrogen and evaporated under high vacuum for 2 hours or until dry. PAs were reconstituted in deionized water with pH adjusted to 7.5-8.0 using 200 mM NaOH, and probe sonicated for a total of 1-2 minutes with 10-second on/off pulse cycles before freezing in liquid nitrogen. All PAs were lyophilized (Labconco Freezone 1 L Freeze Dryer System) and stored at −20° C. until use.

ROS-Ac2-26 and MMP-Ac2-26 PA cleavage assays: To examine ROS-mediated cleavage, 3-morpholinosyd-nonimine hydrochloride (SIN-1, Sigma-Aldrich or Abcam) was used. ROS-Ac2-26 PAs were reconstituted to 0.5 mM in phosphate buffer and treated with 100 μM SIN-1 for 24 hours at 37° C. For MMP2/9-mediated cleavage, human recombinant MMP2 (R&D systems, carrier-free) was used, activated with freshly prepared 1 mM p-aminophenylmercuric acetate (APMA, Sigma-Aldrich) for one hour at 37° C. The APMA disrupts the cysteine-zinc bond in MMP2 responsible for enzyme latency by liberation of the sulfhydryl group. 10% MMP-Ac2-26 PA co-assemblies were prepared at 0.5 mM in a cleavage buffer containing 50 mM tricine, 50 mM NaCl, 50 μM $ZnCl_2$, and 10 mM $CaCl_2$) at pH 7.4, and treated with 40 nM human recombinant MMP2 for 24 hours at 37° C. At the end of each time point, the samples were stored at −20° C., effectively stopping the cleavage reactions. Samples were analyzed at room temperature, 0.04-0.3 mg/mL with 0.1% $NH_4OH$ using a ThermoFisher Q Exactive HIF-X (ThermoFisher, Bremen, Germany) mass spectrometer coupled with a Waters Acquity H-class liquid chromatograph system. Samples were introduced via a heated electrospray source at a flow rate of 0.6 mL/minute. Electrospray source conditions were set as: spray voltage 4.7 kV, sheath gas (nitrogen) 45 arb, auxiliary gas (nitrogen) 30 arb, sweep gas (nitrogen) 0 arb, capillary temperature 350° C., capillary voltage 40 V, and tube lens voltage 100 V. The mass range was set to 150-2000 m/z. All measurements were recorded at a resolution setting of 120,000. Separations were conducted on a Waters Acquity UPLC BEH C18 column (2.1×50 mm, 1.7 m particle size). LC conditions were set at 100% water with 0.1% formic acid (A) ramped linearly over 9.8 minutes to 95% acetonitrile with 0.1% formic acid (B) and held until 10.2 minutes. At 10.21 minutes the gradient was switched back to 100% A and allowed to re-equilibrate until 11.25 minutes. Injection volume for all samples was 3 L. Data was analyzed on Xcalibur (ThermoFisher, Breman, Germany).

TEM: Conventional TEM images were taken on a FEI Tecnai T-12 TEM at 80 kV with a Gatan Orius® 2 k×2 k CCD camera. PAs at 1 mM in phosphate buffered saline (PBS) were prepared for TEM by pipetting 8 μL atop copper supports that were covered with thin carbon foil 400-mesh and treated with glow discharge. After two minutes, samples were rinsed with deionized water and stained with 2% uranyl acetate for two minutes before imaging. PA nanofiber length was quantified manually using Fiji open source image processing software. Cryogenic TEM was performed on a JEOL 1230 using 100 kV accelerating voltage and Gatan 831 CCD camera. 10% ROS- or MMP-Ac2-26 PAs were aged for four days at 1 mM, 4° C. in PBS containing 10% v/v fetal bovine serum (FBS, heat inactivated, Gibco). PAs were pipetted at 7.0 L volumes onto 300-mesh copper grids with lacey carbon support (Electron Microscopy Sciences) that were treated with glow discharge for one minute. Samples were blotted twice at one second per blot before plunging plunged into liquid ethane using a Vitrobot Mark IV (FEI) vitrification robot operating at 95% humidity. After vitrification, the samples were transferred under liquid nitrogen to a Gatan 626 cryo-holder.

Small angle x-ray scattering (SAXS): SAXS characterization of the PA nanofibers was performed at the Advanced Photon Source in the Argonne National Laboratory on beamline 5-ID-D, DuPont-Northwestern-Dow Collaborative Access Team Synchrotron Research Center. Samples were prepared at 5 mM in PBS solution, aged at least 24 hours at 4° C., and analyzed in 1.5 mm quartz capillaries (Charles Supper) at 17 keV with a charged couple device photon detector located 245 cm behind the sample. Scattering intensities were collected using wave vector q range of 0.0024 to 0.40 $Å^{-1}$. q represents the scattering vector and is calculated as $q=4\pi \sin(\theta)/\lambda$, with $\theta$ as the scattering angle between the incident beam and detector and $\lambda$ the X-ray wavelength. The plots of scattering intensity versus q were obtained using NIST software Igor Pro v8. The scattering intensities of PBS were subtracted from the PA samples using the Irena SAS macro, and the resulting plots were fitted using NCNR Analysis macro to a polydisperse core shell cylinder model.

Circular dichroism spectroscopy: PA samples were analyzed at 0.5 mM in 0.1 µM phosphate buffer at pH 7.4 with a 0.1 mm pathlength Suprasil® quartz cuvette (Sigma-Aldrich) using a Chirascan™-plus Circular Dichroism Spectrometer (Applied Photophysics). Samples were analyzed at 25° C. or 37° C. from 185 to 260 nm with 0.3 nm step size and analysis time of 1.25 seconds per data point. Spectrum data was averaged from two scans with the phosphate buffer values subtracted.

Zeta potential: The PA charge was characterized using a Zetasizer Nano ZS (Malvern). Samples were prepared at 0.5 mM and passed through a 0.2 µm filter (Acrodisc® Syringe Filters with Supor® Membrane, Pall). At least 10 scans were taken per measurement, three measurements per sample at 25° C. and 37° C.

Nile Red assay: The critical aggregation concentration (CAC) for PA nanofibers was determined by diluting the PAs in Nile Red solution. Nile Red undergoes a blue shift in fluorescence as the hydrophobic character of PAs in the solvent increases, with a corresponding increase in fluorescence intensity due to reduced twisted intramolecular charge transfer. 10% MMP- and ROS-Ac2-26 PAs were diluted from 1 mM to 100 nM in PBS containing of 2.5 µM Nile Red and aged for 24 hours at 4° C. The PAs were aliquoted in triplicate onto a 96-well plate, excited at 550 nm, and the fluorescence read from 580-450 nm. The CAC was determined by plotting the log of the concentration with the corresponding maximum fluorescence intensity, and calculating the concentration at the intersection of the baseline and tangent line to the rising curve.

Macrophage culture and characterization: J774.2 murine macrophages (Sigma-Aldrich) were expanded at $4-9 \times 10^5$ cells/mL in growth media consisting of Dulbecco's Modified Eagle's Medium (Sigma-Aldrich) containing 4.5 g/L glucose, 2 mM L-glutamine, 10% v/v FBS, 100 U/m penicillin, and 100 µg/mL streptomycin. Cells were passaged using Accutase™ (StemCell Technologies) and used at passage 6-9 for all experiments. The cells were detached with Accutase™ and gentle scraping, counted, and re-suspended in flow cytometry buffer containing 2% w/v bovine serum albumin (BSA, heat shock fraction free of proteases, globulin, and fatty acids, Sigma-Aldrich) and 0.1% w/v sodium azide (Sigma-Aldrich). To minimize non-specific binding of immunoglobin to Fc receptors, macrophages were incubated with anti-mouse CD16/32 antibody (TrueStain FcX™, Biolegend) at $1$ µg/$1 \times 10^5$ cells for 10 minutes at 4° C. APC anti-mouse CD11b antibody or APC Armenian hamster IgG isotype control antibody (Biolegend) were added at 0.4 µg/$1 \times 10^5$ cells, FPR2 antibody (Novus Biologics) was added at 2 g/x $10^5$ cells, and all samples were incubated for 30 minutes at 4° C. The cells were washed once with flow cytometry buffer by centrifugation at 300×g. FPR2 samples were further treated with goat anti-rabbit Alexa Fluor 488 secondary antibody (Invitrogen) at 2 µg/$1 \times 10^5$ cells for 20 minutes at 4° C., followed by a wash step. Unstained macrophages served as controls and contained 7AAD viability staining solution (Biolegend) at 0.1 µg/$1 \times 10^5$. All samples were suspended in 4% paraformaldehyde (Electron Microscopy Sciences) in PBS until analysis. Macrophage activation towards a pro-inflammatory phenotype was confirmed by increased levels of inducible nitric oxide synthase (iNOS) using flow cytometry. Macrophages were activated to simulate a pro-inflammatory, M1 phenotype using 100 ng/mL of interferon gamma (IFN-7, mouse carrier-free protein, Biolegend), added to $4 \times 10^5$ cells for 12-16 hours, rinsed once, and treated with 10 µg/mL lipopolysaccharide (LPS, derived from *Escherichia coli* 0111:B4, Sigma-Aldrich) for 24 hours. Flow cytometry was performed by permeabilizing detached cells with 0.0625% Triton-X for 10 minutes at 4° C. Macrophages were rinsed with flow cytometry buffer by centrifugation before adding APC-iNOS monoclonal antibody (eBioscience™) at 0.12 µg/$1 \times 10^5$ cells for 30 minutes at 4° C. The cells were rinsed once more before re-suspension in 4% paraformaldehyde. All samples were analyzed using Attune NxT Acoustic Focusing Cytometer (Thermo Fisher) with at least 2000 events counted per condition.

To examine MMP2/9 production from macrophages, conditioned media was collected from tissue culture plates. Protein concentration was measured using a bicinchoninic acid assay (BCA assay, Pierce™). After measuring protein concentration, a 4-16% gradient sodium dodecyl sulfate polyacrylamide gel (SDS-PAGE, Sigma-Aldrich and ThermoFisher Scientific) containing 1 mg/mL gelatin (Sigma-Aldrich) was cast. 20 g of total protein from each media sample was mixed with 2× non-reducing sample buffer (1.6% SDS, 8% glycerol, 0.01% bromophenol blue, 217 mM Tris-HCl) and loaded into the gelatin SDS-PAGE. Samples were passed through the gel using a constant voltage (150 V) until the bromophenol blue in the loading buffer ran out of the gel. Gels containing protein samples were then washed twice for 30 minutes with washing buffer (2.5% Triton X-100, and 50 mM Tris-HCl) to renature loaded proteins, and rinsed with incubation buffer (1% Triton X-100, 50 mM Tris-HCl, 5 mM $CaCl_2$), and 1 µM $ZnCl_2$). Following washes, the gelatin SDS-PAGE was incubated for 24 hours at 37° C. with incubation buffer to activate gelatinases present in the samples. Gels were then stained with Coomassie Brilliant Blue (Sigma-Aldrich) for one hour and developed with de-staining solution until bands were observed. Images of the gels were taken using a desktop scanner.

Cytocompatibility: Macrophages were seeded at $2.1 \times 10^5$ cells/$cm^2$ on 24 well plates and treated with 32 µM of Ac2-26 or 320 µM PA co-assemblies (final Ac2-26 concentration of 32 µM) for 24 hours. Prior to addition, all PAs were mixed by vortex or water bath sonication until dissolved and passed through a 0.2-µm filter. Cells were detached by Accutase treatment for 20 minutes and counted using a MUSE® Count and Viability Assay Kit and cytometer (Emd millipore).

Cellular uptake and localization of ApoA1-Ac2-26 PA: PAs containing 40 mol % ApoA1 PA, 10 mol % MMP-Ac2-26 or ROS-Ac2-26 PA, 45.5 mol % E2 filler PA, and 4.5 mol % E2 filler PA with AF546 were co-assembled as described above and aged at least 1 week in PBS at 4° C. to promote nanofiber formation. Macrophages were seeded onto 6-channel µ-Slide VI 0.4 (ibidi) at $2.1 \times 10^5$ cells/$cm^2$ and allowed to adhere for 24 hours before adding 0.33 µM 10% MMP- or ROS-Ac2-26 PA and incubated at 37° C. for 1 or 24 hours. At each time point, the samples were fixed with 4% paraformaldehyde for 10 minutes, followed by permeabilization with 0.125% Triton-X for 10 minutes. The samples were rinsed twice with PBS and incubated with blocking buffer consisting of 2% w/v BSA for one hour at room temperature before incubating with 20 µg/mL LAMP1 antibody (rabbit polyclonal, abcam) for 12-18 hours at 4° C. The samples were rinsed twice with PBS containing 0.01% Tween-20 at one hour per rinse followed by an hour rinse with PBS before adding 2 µg/mL donkey anti-rabbit Alexa Fluor Plus 647 (Highly cross-adsorbed secondary antibody, Invitrogen) for 12-18 hours at 4° C. The samples were rinsed twice with PBS before adding 5 μg/mL 4',6-Diamidino-2-Phenylindole (DAPI, ThermoFisher Scientific) and phalloidin (1:1000 dilution, CruzFluor™ 488 conjugate, Santa Cruz Biotechnology) for one hour at room temperature. Samples were rinsed and stored in PBS until image analysis. Microscopy was performed using Zeiss 880 confocal microscopy at 63× magnification with numerical aperture of 1.4. Lasers at 405, 488, 561, and 633 nm were used to collect images through Multi Channel acquisition, which uses a separate scan for each channel to avoid spectral overlap. 3D images were created using z-stacks with 9-14 μm thick sections compiled from 0.22 μm slices using a line step of 1, speed of 8, and image size of 1024×1024 pixels at 16 bit depth. To examine colocalization of PAs to endosomes/lysosomes, Manders coefficient calculations using the Coloc 2 plugin from Fiji were used.

Therapeutic effects of ApoA1-Ac2-26 PAs: 10% ROS- and MMP-Ac2-26 PAs, as well as Ac2-26 peptide were added together with 10 μg/mL LPS at 32 μM Ac2-26 to macrophages. 40% ApoA1 PA and E2 filler PA were added with LPS at epitope equivalent masses to the ApoA1-Ac2-26 PA co-assemblies. 10% ROS- and MMP-Ac2-26 PA co-assemblies were aged at least 24 hours at 4° C. prior to use. All PAs and peptides were sonicated in a water bath sonicator for 15 minutes and passed through a 0.22-μm filter prior to use. The supernatant from each treatment was collected, centrifuged at 300×g to avoid cell contamination, and diluted 1:10 with PBS prior to analysis with a Sievers Nitric Oxide Analyzer (NOA 280i, GE Water & Process Technologies). In the absence of hemoglobin, the nitric oxide produced in the cell cultures is assumed to react with dissolved oxygen to form nitrite. To convert the nitrite to nitric oxide (NO), a 1% w/v solution of potassium iodide (KI) was used as a reducing agent. Concerning the quantification of NO, the reducing solution made of KI in acetic acid and water provides an excess of I– that reacts with nitrite yielding ·NO. The ·NO is carried by N2 flow to the reaction chamber inside the NOA where it reacts with O3, yielding NO2 in a higher energy state that will emit a photon to return to its basal state:

Reduction of $NO_2^-$ to ·NO

$I_3^- \rightleftharpoons I_2 + I^-$

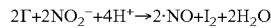
$2I^- + 2NO_2^- + 4H^+ \rightarrow 2 \cdot NO + I_2 + 2H_2O$ $O_3$ Based Chemiluminescent Detection of ·NO

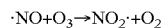
$\cdot NO + O_3 \rightarrow NO_2 \cdot + O_2$

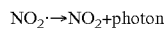
$NO_2 \cdot \rightarrow NO_2 + photon$

Figure 19:
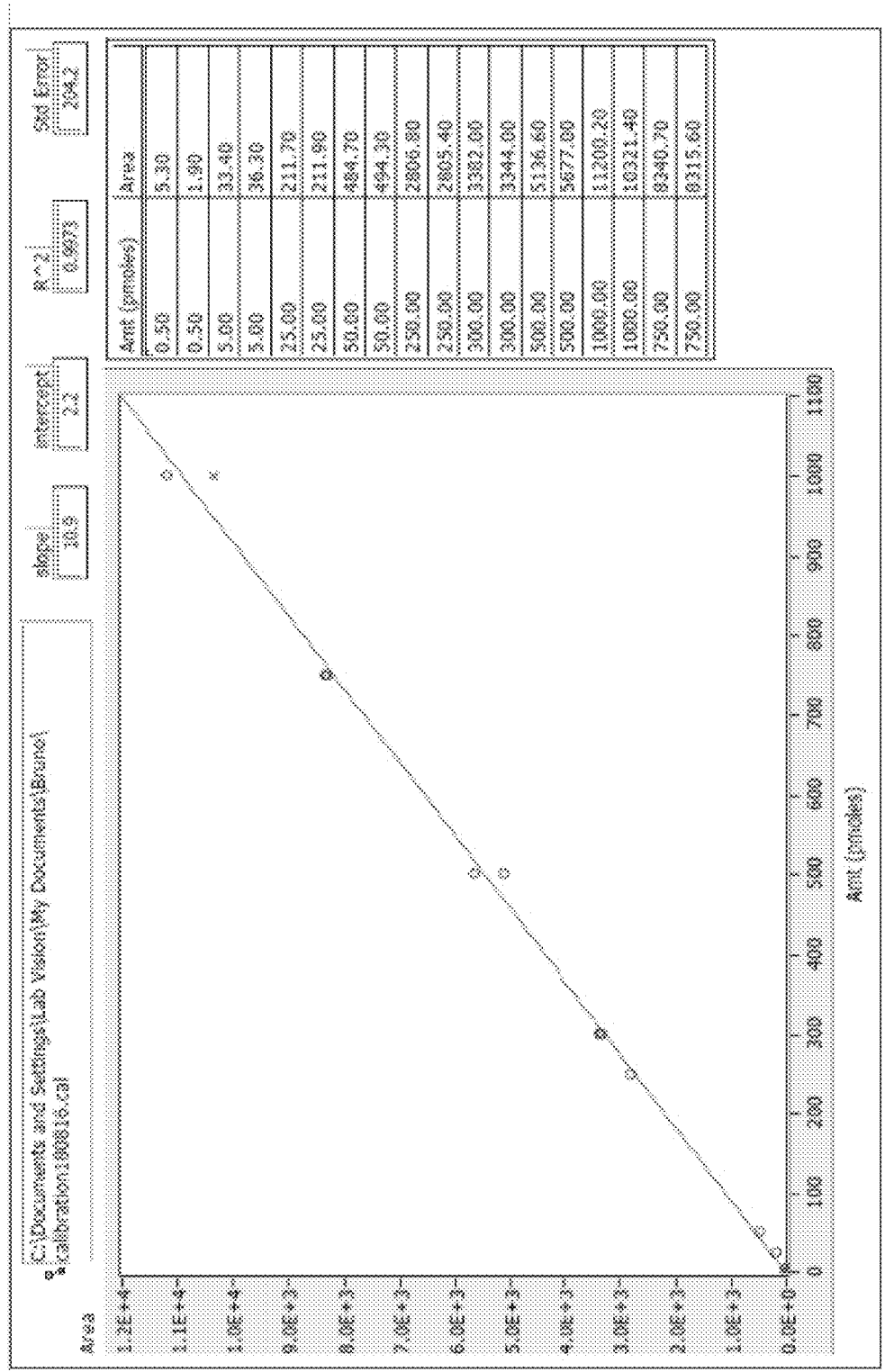
FIG. 19. NaNO2 calibration curve. Integrated area of the peaks registered after the different amounts of NaNO2 injected.

The calibration curve of NaNO2 was prepared using volumetric glass materials in water at concentrations of 10 nM, 100 nM, 500 nM, 1 μM, 5 μM, 10 μM, 50 μM, and 100 μM. The curve is shown in FIG. 19.

To measure cell metabolic activity, thiazolyl blue tetrazolium bromide (MTT, Sigma-Aldrich) was added to cells at 0.4 mg/mL in complete medium for 4 hours at 37° C. The plates were then aspirated and 100 L of DMSO added for 10-15 minutes at room temperature on a plate shaker at low speed setting. The plates were run on an Epoch plate reader using absorbance at 560 nm corrected for background at 670 nm. Flow cytometry analysis for iNOS expression followed the methods described above.

Statistical analysis: Data are presented as mean±SEM. Sample sizes are included in figure legends or methods for each experiment. Data were analyzed for statistical significance using one- or two-factor analysis of variance (ANOVA) followed by a post-hoc Student's t-test. JMP® software was used for all analysis.

Results:

Design and characterization of atheroma niche-responsive PAs: Atheroma niche-responsive linkages were developed using ROS- or MMP2/9-sensitive peptides due to their ease of PA incorporation during peptide synthesis, and their bioresorbable properties. Arginine, histidine, lysine, and proline are readily oxidized by metal-catalyzed oxidative systems. Of these residues, only proline is capable of forming tertiary amide bonds, which are more susceptible to oxidation than secondary amide bonds. In addition, the mechanism of proline oxidation to glutamic semialdehyde does not involve the formation of reactive carbonyl groups that may aggravate existing inflammation within the atherosclerotic lesion. Supporting their potential for cleavage by pro-inflammatory cells within the atherosclerotic niche, prolines incorporated into poly(ethylene glycol) (PEG) and poly(F-caprolactone) scaffolds are degradable by M1 polarized murine macrophages within nine days in vitro. Hence, for this study, ROS-responsive Ac2-26 PAs (ROS-Ac2-26 PA) were designed by incorporating five prolines, flanked by lysine residues to enhance solubility. The chemical structures of Chemical structures of ROS-Ac2-26 PA, MMP-Ac2-26 PA, and ApoA1 PA can be found in Peters, Erica B et al., Advanced healthcare materials vol. 8,3 (2019), the entire contents of which are incorporated herein by reference.

Figure 7A:
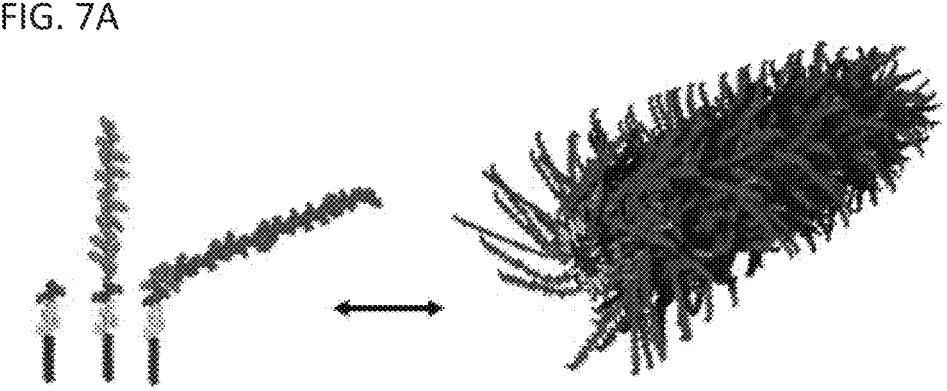
FIG. 7A-7B show molecular graphics of (FIG. 7A) ROS-Ac2-26-ApoA1 PA and (FIG. 7B) MMP-Ac2-26-ApoA1 PA nanofibers formed by self-assembly of three PAs: the PA backbone (E2 filler PA) containing an alkyl tail (gray), β-sheet forming peptide sequence (yellow), and charged region to enhance solubility (green); ApoA1 PA with 4F peptide (orange), and PAs with pro-resolving Ac2-26 (blue) attached with a ROS- or MMP2/9-cleavable linkage (pink).
Figure 7B:
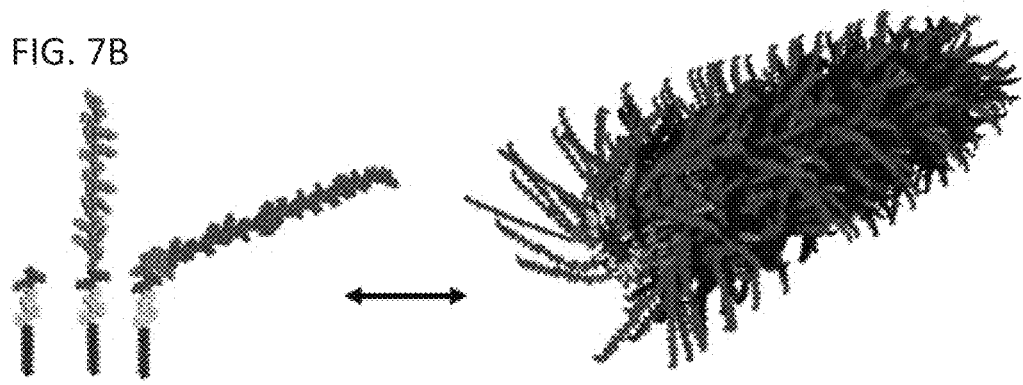

The MMP2/9-sensitive peptide sequence GGGPQG↓IWGQGK (abbreviated as PQ, with ↓ denoting cleavage site) is cleavable by human aortic smooth muscle and blood-derived endothelial cell co-culture within a PEG hydrogel system, enabling three-dimensional microvessel formation in vitro. Given the increased production of MMP2/9 by vascular and immune cells in the atherosclerotic niche, an MMP2/9-sensitive PA was designed containing the PQ sequence to link Ac2-26 (MMP-Ac2-26 PA) into the PA backbone. An atheroma-targeting, therapeutic nanocarrier may be created through co-assembly with ApoA1 PA and either ROS- or MMP-Ac2-26 PAs to generate supramolecular nanofibers. FIG. 7A-7B show molecular graphics of (7A) ROS-Ac2-26-ApoA1 PA and (7B) MMP-Ac2-26-ApoA1 PA nanofibers formed by self-assembly of three PAs: the PA backbone (E2 filler PA) containing an alkyl tail (gray), β-sheet forming peptide sequence (yellow), and charged region to enhance solubility (green); ApoA1 PA with 4F peptide (orange), and PAs with pro-resolving Ac2-26 (blue) attached with a ROS- or MMP2/9-cleavable linkage (pink). All PAs were synthesized using solid phase peptide synthesis and validated for expected molecular weight through liquid chromatography coupled with mass spectrometry.

Figure 8:
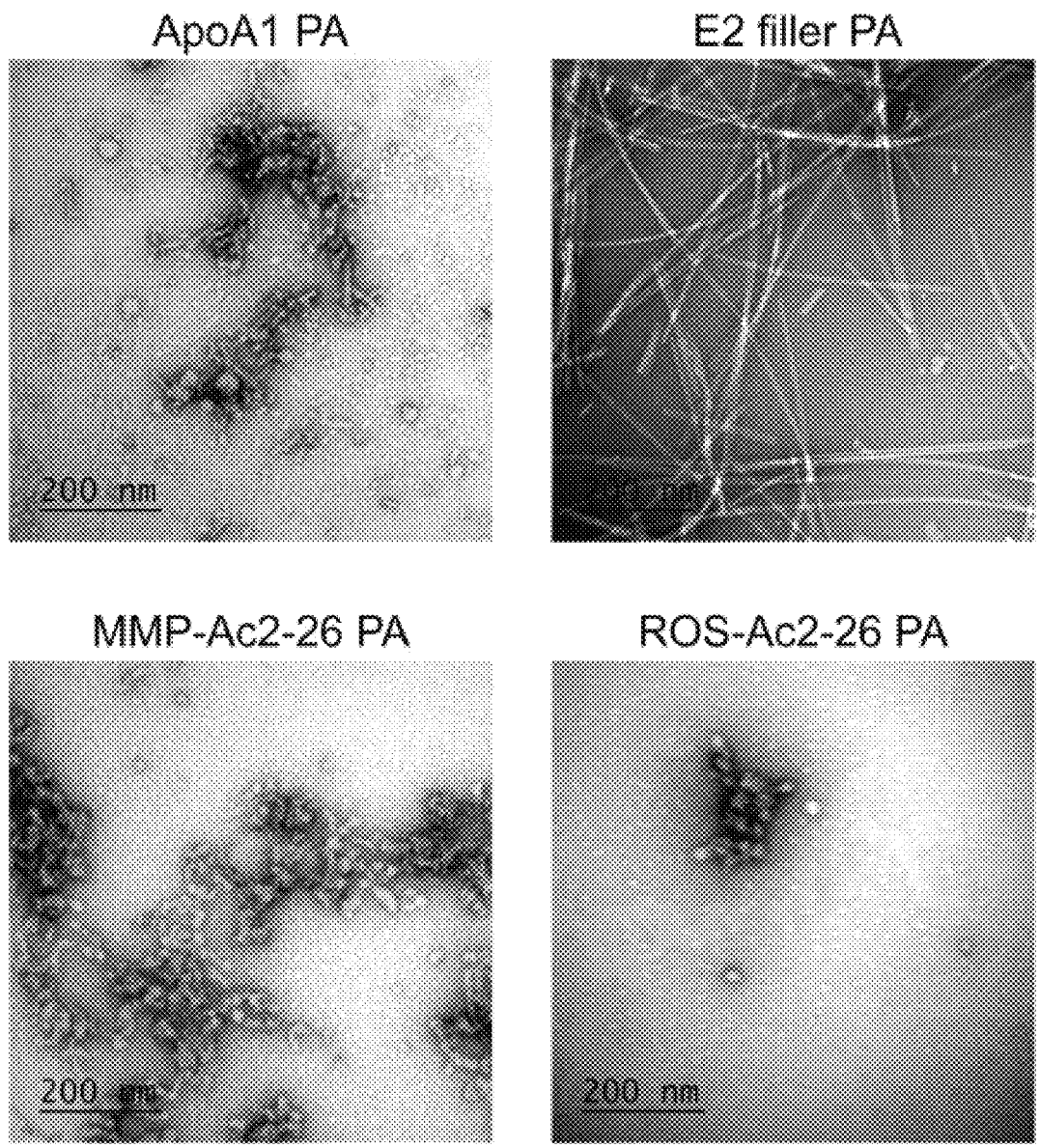
FIG. 8 shows TEM images of 100% PA structures.
Figure 9A:
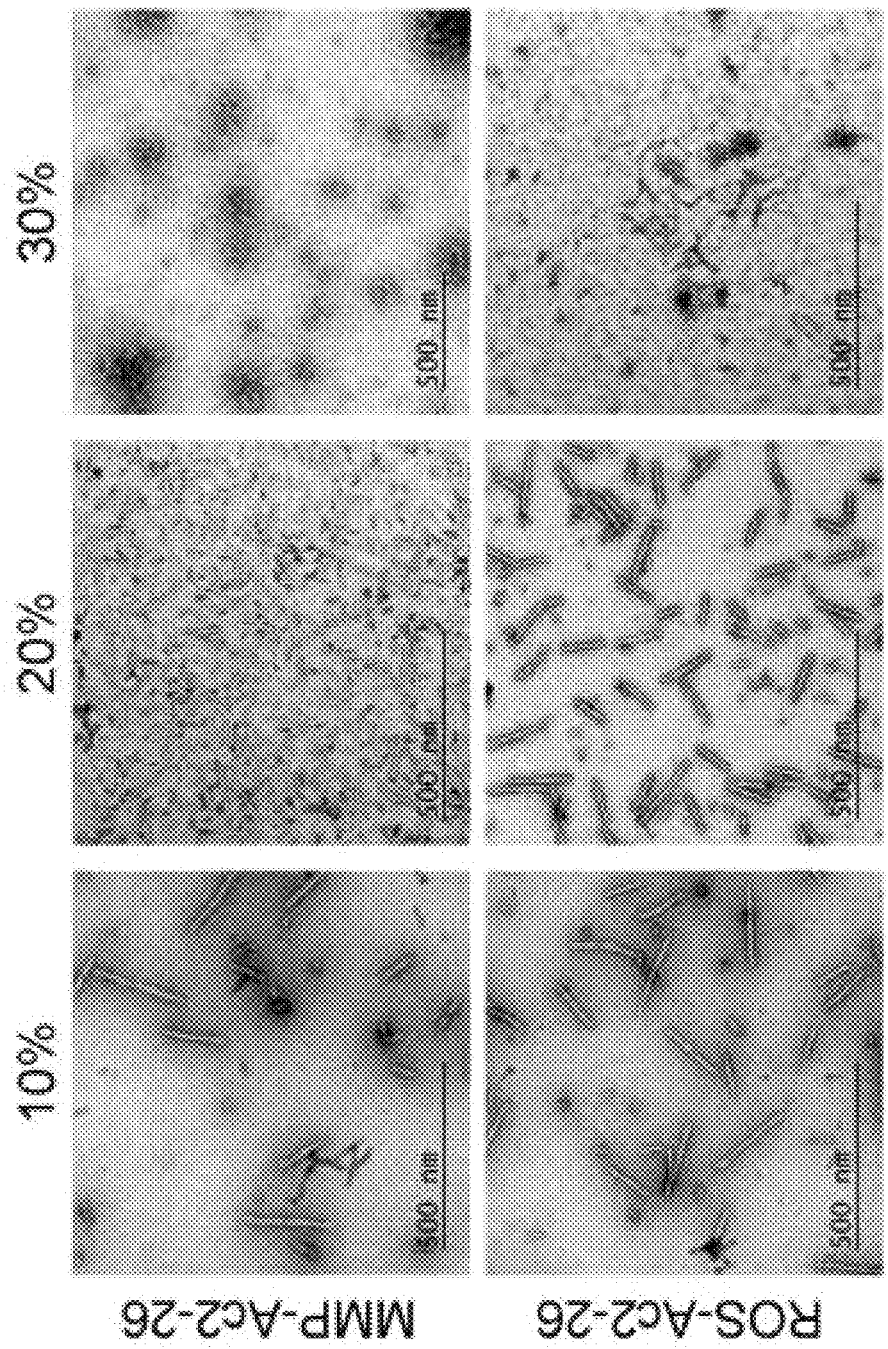
FIG. 9A-D. Determining parameters for ApoA1-Ac2-26 PA nanofiber formation. PAs were co-assembled based upon molar ratio of the MMP- or ROS-Ac2-26 PA therapeutic with 40 mol % ApoA1 PA and the remainder as E2 filler PA. The PAs were imaged using TEM after being (FIG. 9A) freshly dissolved, (FIG. 9B) aged for 24 hours, or (FIG. 9C) annealed for 30 minutes at 80° C.
Figure 9B:
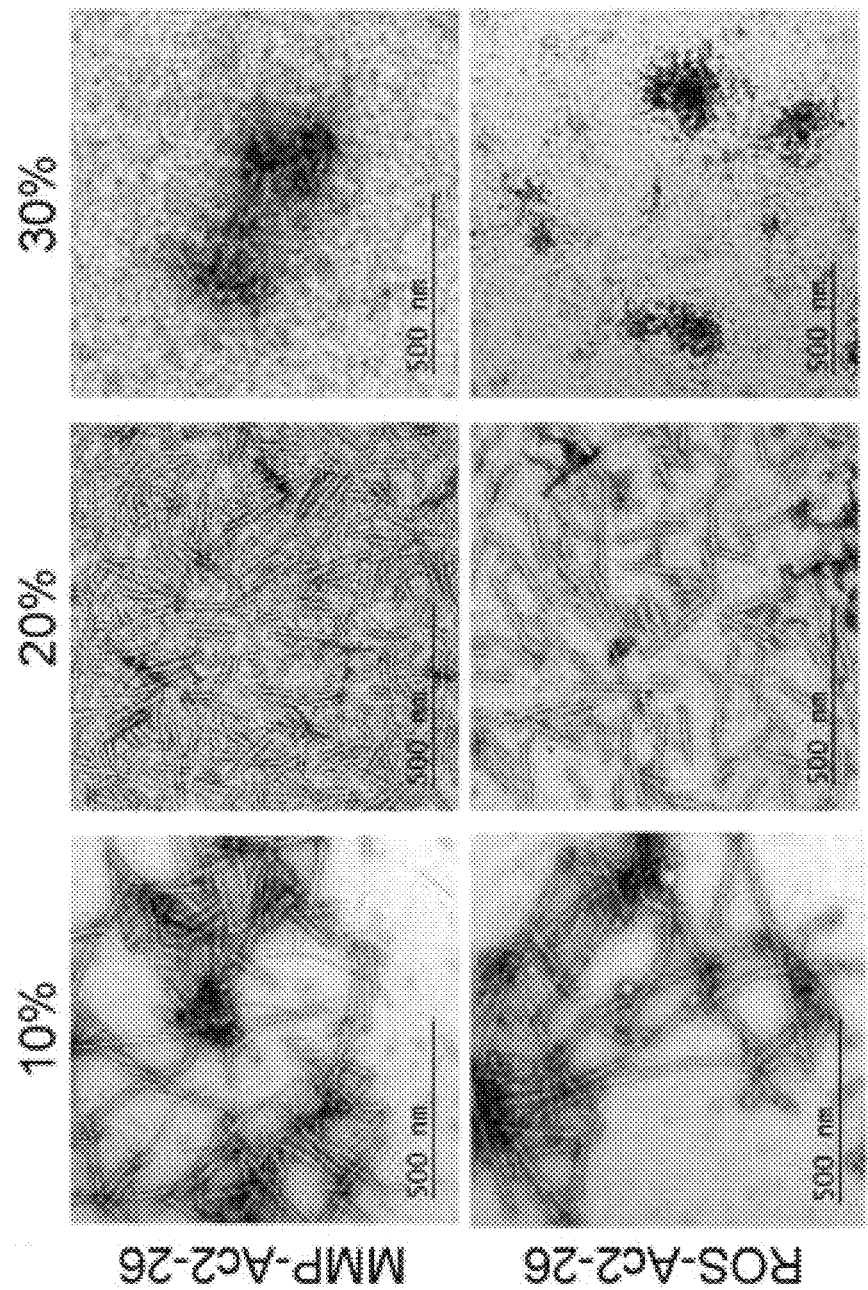
Figure 9C:
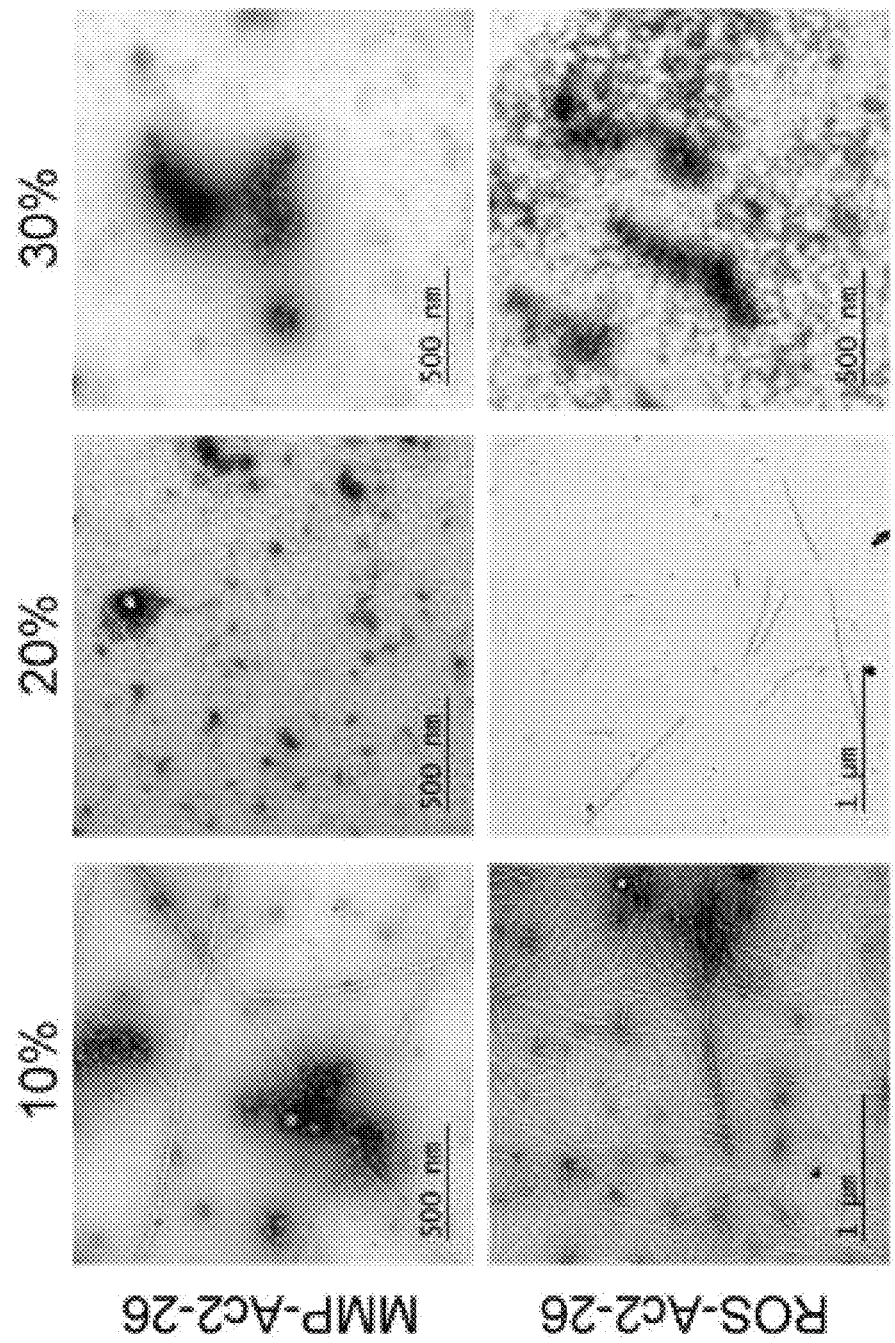
Figure 9D:
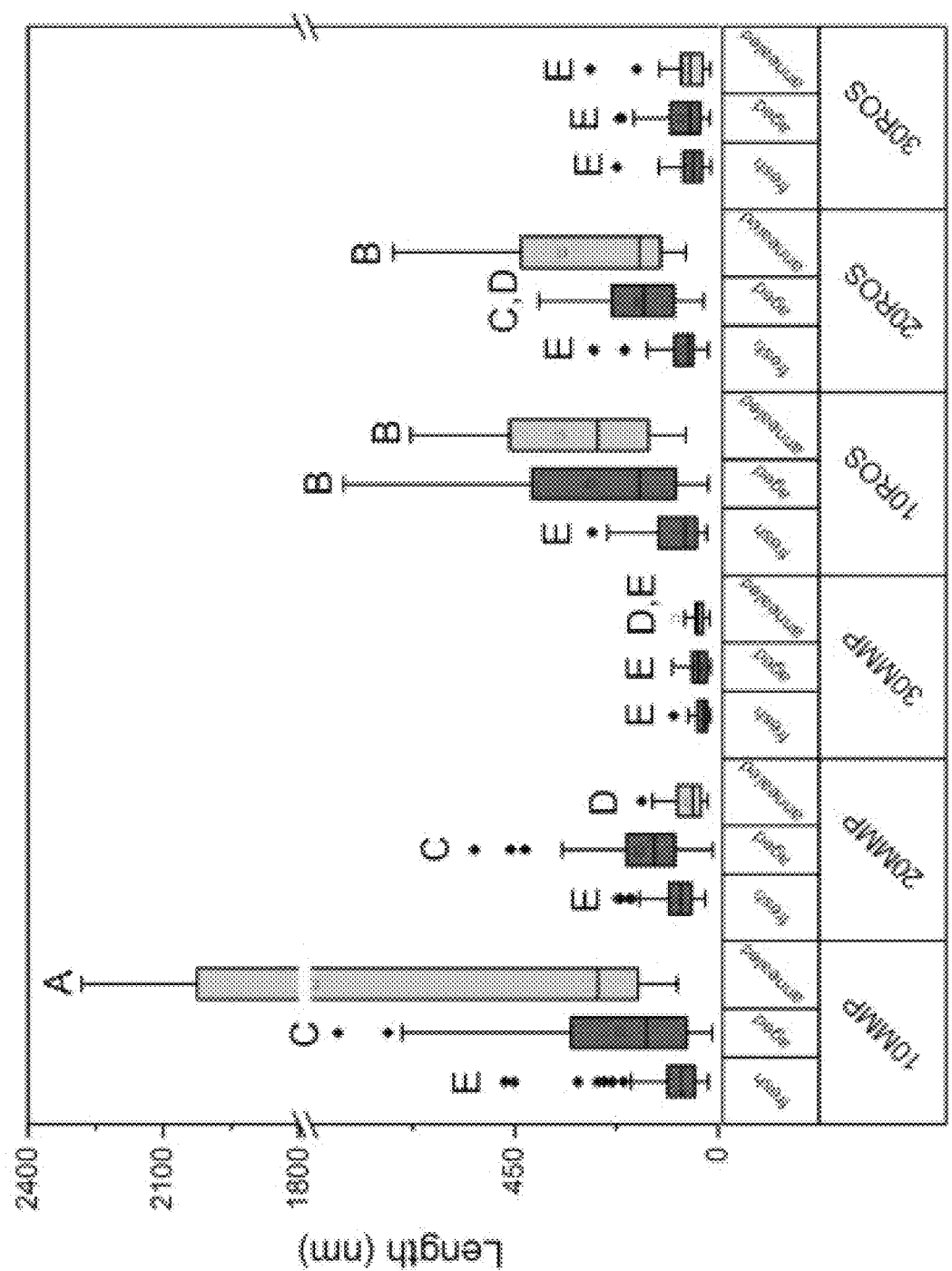

ApoA1-Ac2-26 PA co-assembly and characterization: ROS- or MMP-cleavable Ac2-26 PAs were co-assembled with ApoA1 PA to generate an atheroma-targeted immunotherapeutic. However, direct co-assembly of ROS- or MMP-Ac2-26 PAs with ApoA1 PAs did not result in nanofiber formation as each PA formed aggregates in aqueous solution, shown through transmission electron microscopy (TEM, FIG. 8). Co-assembly with a diluent PA can enhance nanofiber formation. For example, as shown in Example 1 co-assembly of the ApoA1 PA with E2 filler PA enabled nanofiber formation without compromising PA bioactivity. Accordingly, it was next determined the PA co-assembly parameters that would support nanofiber formation between the E2 filler PA, ROS- or MMP-Ac2-26 PA, and ApoA1 PA.

The co-assembled ApoA1-Ac2-26 PA contains a minimum of 40 mol % ApoA1 PA to target atheroma. The processing conditions for PA co-assembly can significantly affect nanofiber structure as self-assemblies exist at distinct energy landscapes, ranging from a metastable thermodynamic state with short fibers to the thermodynamically favored state of long nanofibers. Annealing PAs by temporarily increasing the temperature to 80° C. provides thermal energy to assist nanofiber elongation. Aging the PAs also enhanced nanofiber formation by allowing the fibers more time to self-assemble towards a more energetically favorable state. For these reasons, the effect of aging and annealing PAs, as well as varying molar ratios of ROS- or MMP-Ac2-26 PA and E2 filler PA, on ApoA1-Ac2-26 PA nanofiber formation were studied. Based on the average fiber length and lack of aggregates, it was found that PAs co-assembled from 10 mol % MMP- or ROS-Ac2-26 PA, 50 mol % E2 filler PA, and 40% ApoA1 PA (hereafter referred to as 10% MMP- or ROS-Ac2-26 PAs), aged at least 24 hours at 4° C. were the most conducive for nanofiber formation (FIG. 9A-9D). The median lengths of 10% MMP-Ac2-26 and 10% ROS-Ac2-26 PA nanofibers were 159 nm and 174 nm, respectively.

Figure 10A:
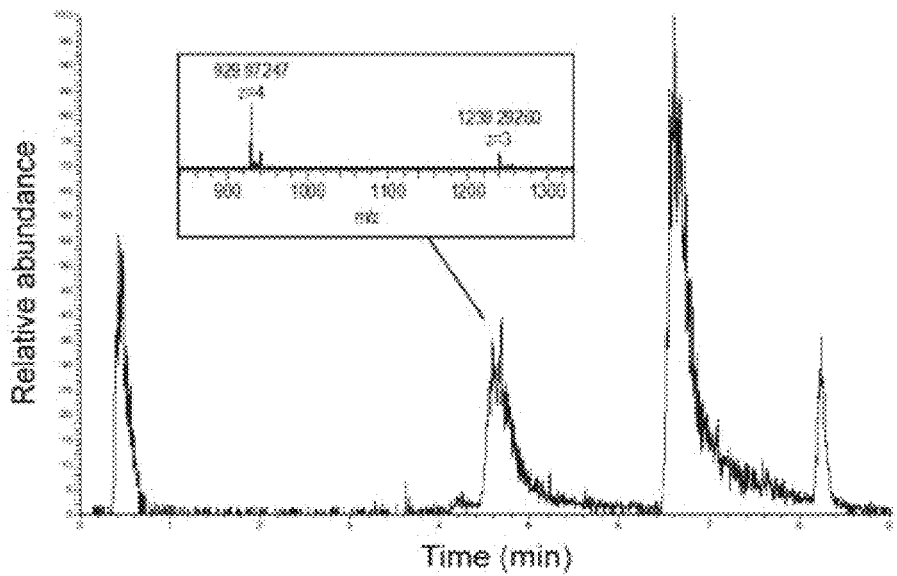
FIG. 10A-D. Representative chromatographs and mass spectra indicating Ac2-26 release from PA nanofibers.
Figure 10B:
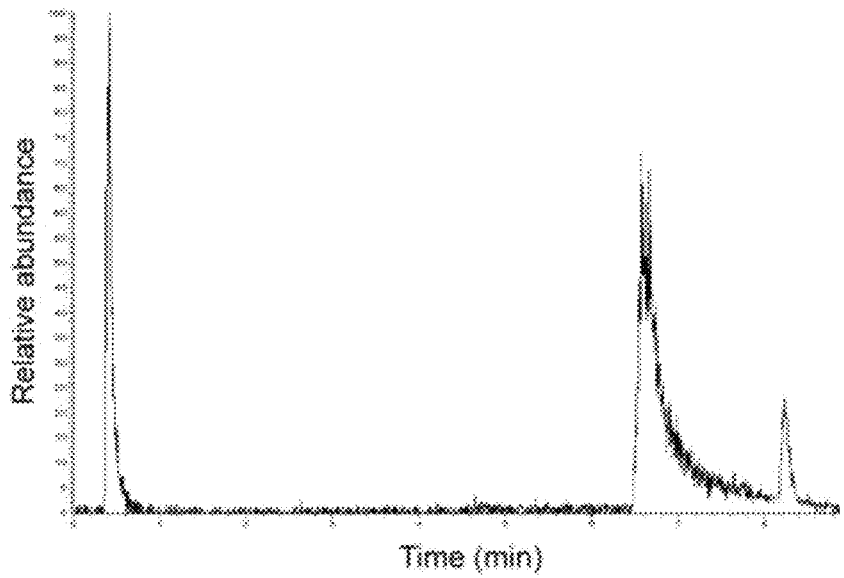
Figure 10C:
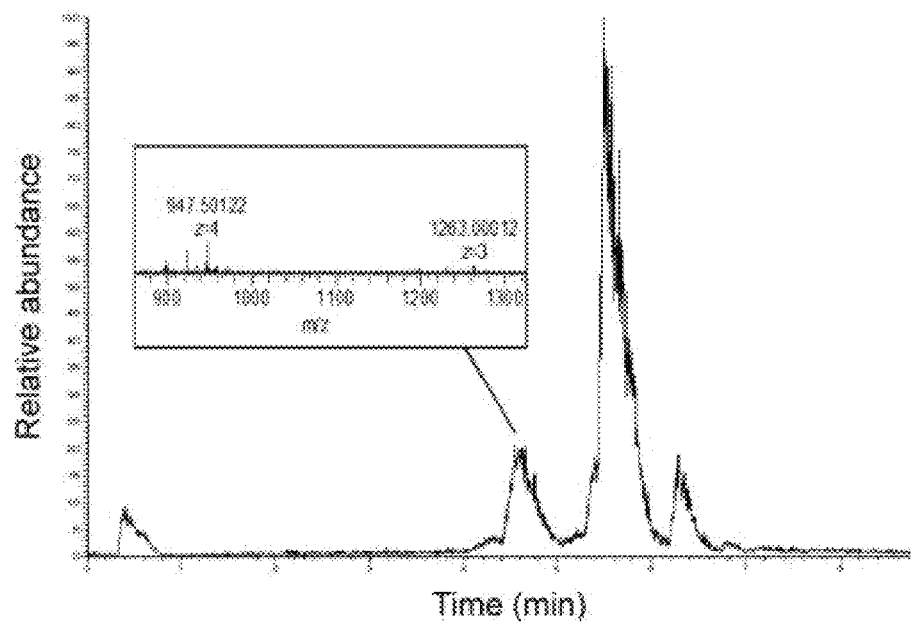
Figure 10D:
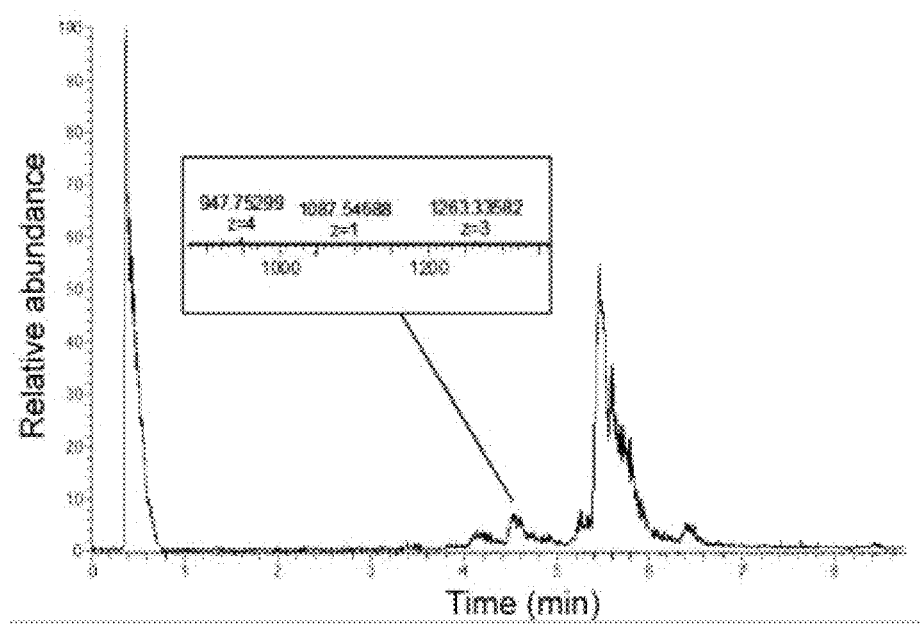

To confirm that Ac2-26 is released from the PA nanofibers upon exposure to biochemical cues overexpressed in atheroma microenvironment, the PAs were treated with MMP2 or SIN-1. SIN-1 spontaneously decomposes to yield superoxide and nitric oxide in aqueous solutions. The MMP-Ac2-26 PA nanofibers released Ac2-26 after 24 hours of treatment with 40 nM MMP2, evidenced by product elution times and molecular weights matching that of the Ac2-26 peptide and the cleaved MMP2-responsive peptide sequence (4.4-4.8 minutes, 3716 µg/mol, FIG. 10A-10B). Similarly, the ROS-Ac2-26 PAs released Ac2-26 after 24 hours of treatment with 100 µM SIN-1 as shown by the presence of products near the expected elution time and molecular weight of Ac2-26 (4.4-4.8 minutes, 3295-3791 µg/mol, FIG. 10C-10D). The range of molecular weights correspond to the Ac2-26 peptide attached to residual oligoprolines. Surprisingly, the untreated ROS-Ac2-26 PA also showed the presence of cleaved Ac2-26 peptide. One possible explanation for this result is that ambient atmospheric oxygen caused some cleavage to occur during the assay period.

Figure 11A:
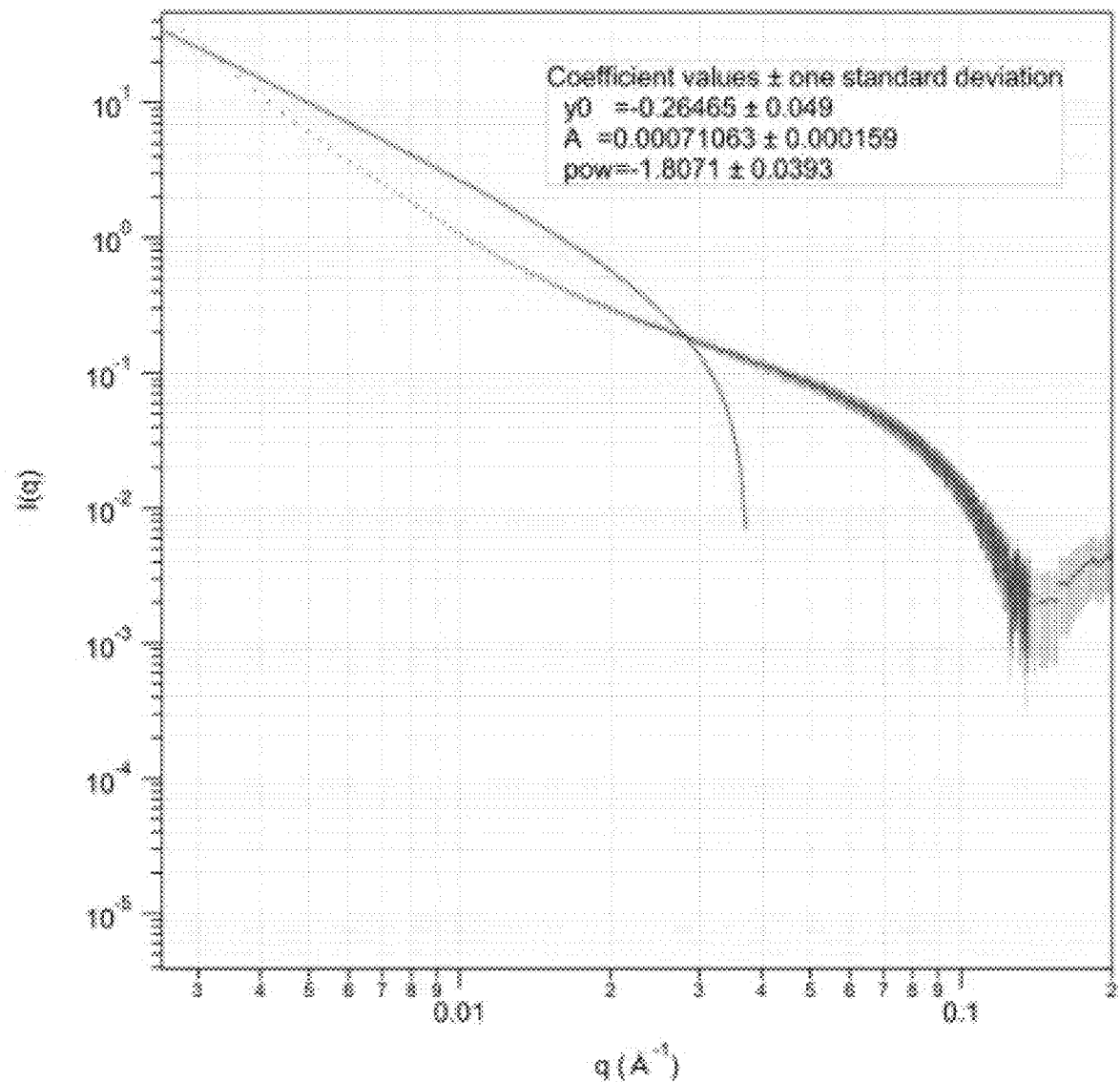
FIG. 11A-11B. Power law fit analysis, indicated by the red line, to the low q regime for Guinier approximation of nanofiber shape. The slopes are given as the power value (pow) for (FIG. 11A) 10% MMP-Ac2-26 PA and (FIG. 111B) 10% ROS-Ac2-26 PA.
Figure 11B:
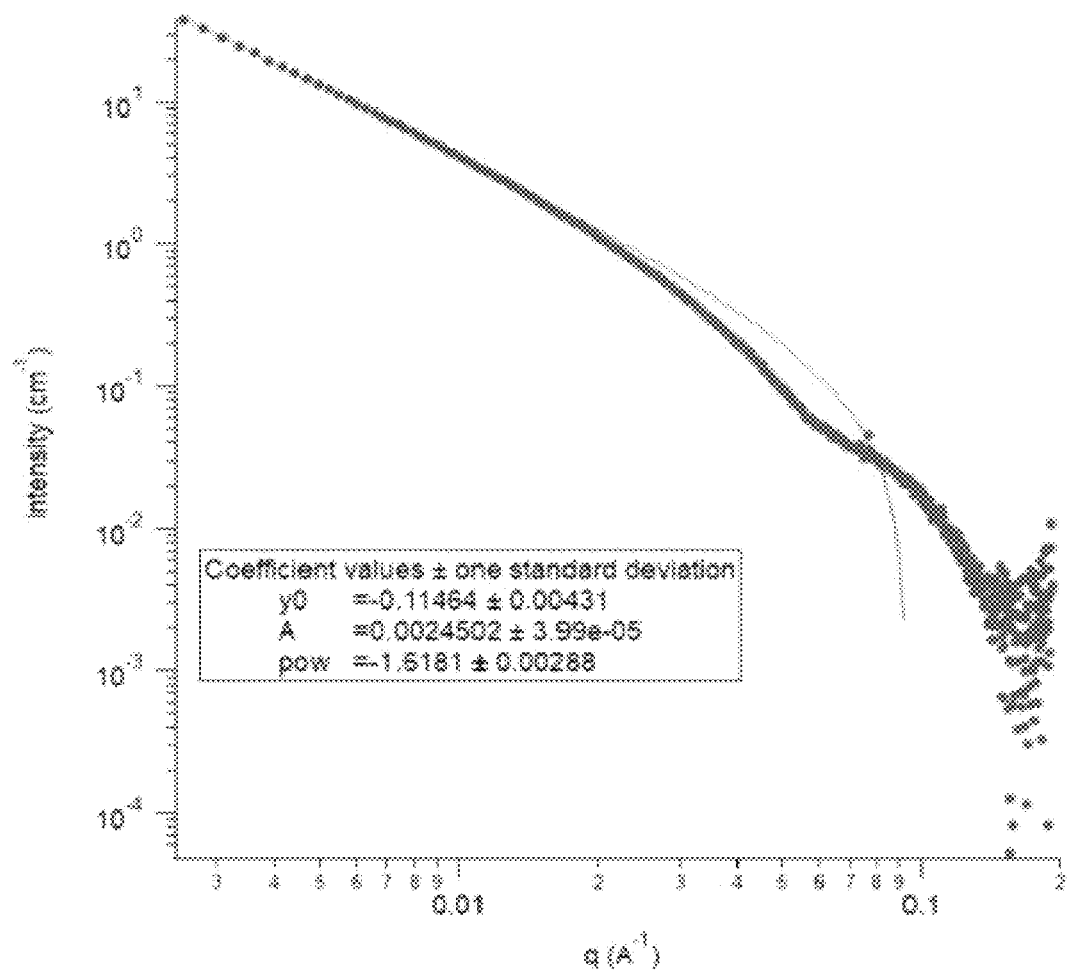
Figure 12A:
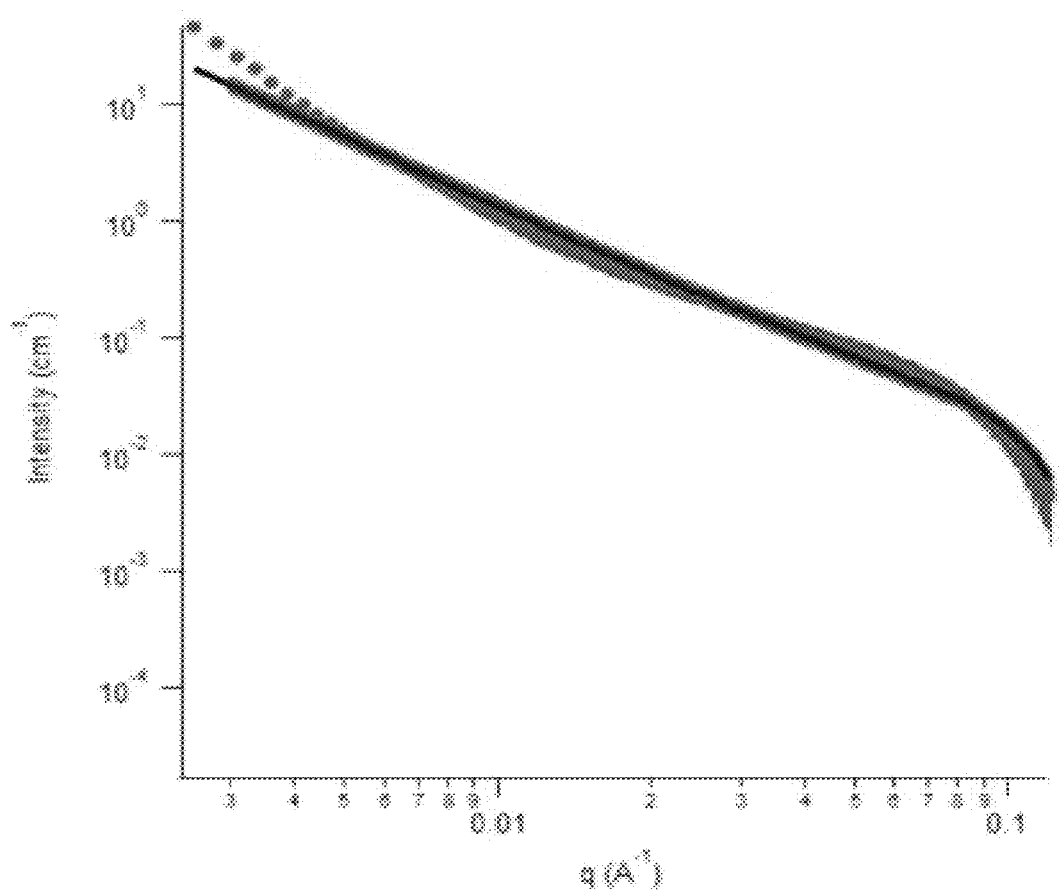
FIG. 12A-12D. Characterization of PA structure using SAXS for (FIG. 12A) 10% MMP-Ac2-26 and (FIG. 12B) 10% ROS-Ac2-26 PAs. Plot indicates scattering intensity vs. wave vector. The solid red line represents the best fit of polydisperse core shell cylinder model form factor. The black line indicates the region where the data was fit to the model. PA stability in serum-containing solution as assessed through cryoEM for (FIG. 12C) 10% MMP-Ac2-26 and (FIG. 12D) 10% ROS-Ac2-26 PAs. Scale bar equals 200 nm, images in panel C and D are taken at the same magnification FIG. 13A-13D. Characterization of ApoA1-Ac2-26 PA nanofibers for secondary structure through (FIG. 13A) circular dichroism spectroscopy and (FIG. 13B) zeta potential. Nile Red was used to determine the critical aggregation concentration (CAC) for (FIG. 13C) 10% MMP-Ac2-26 and (FIG. 13D) 10% ROS-Ac2-26 PAs based upon the blue shift at decreasing PA concentrations (inset).
Figure 12B:
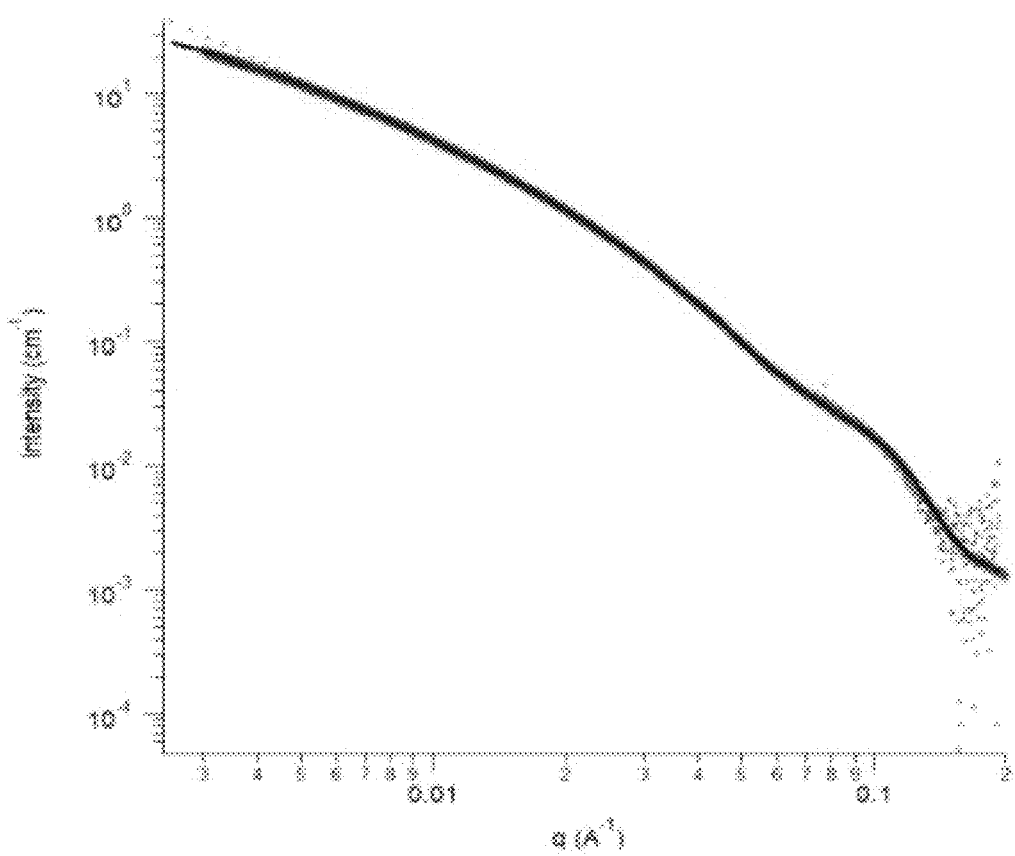
Figure 12C:
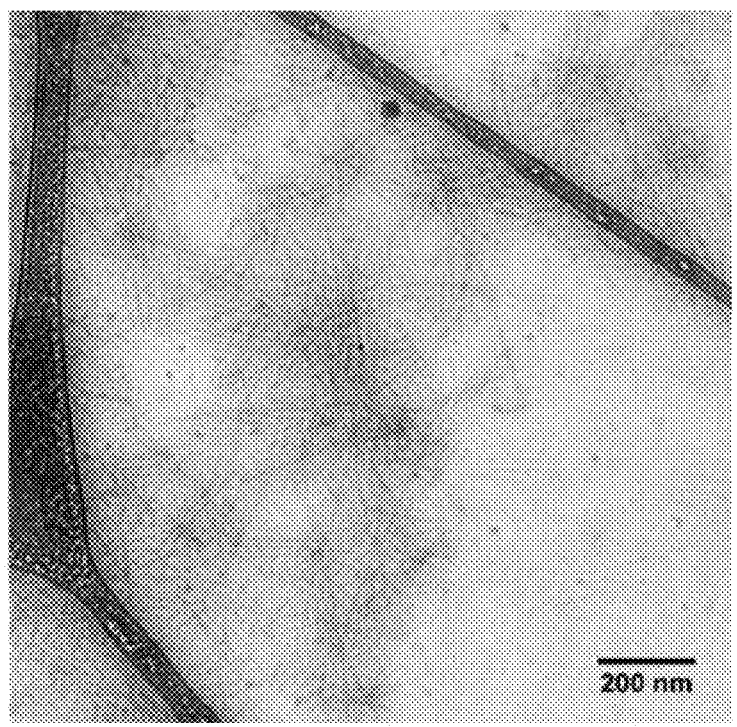
Figure 12D:
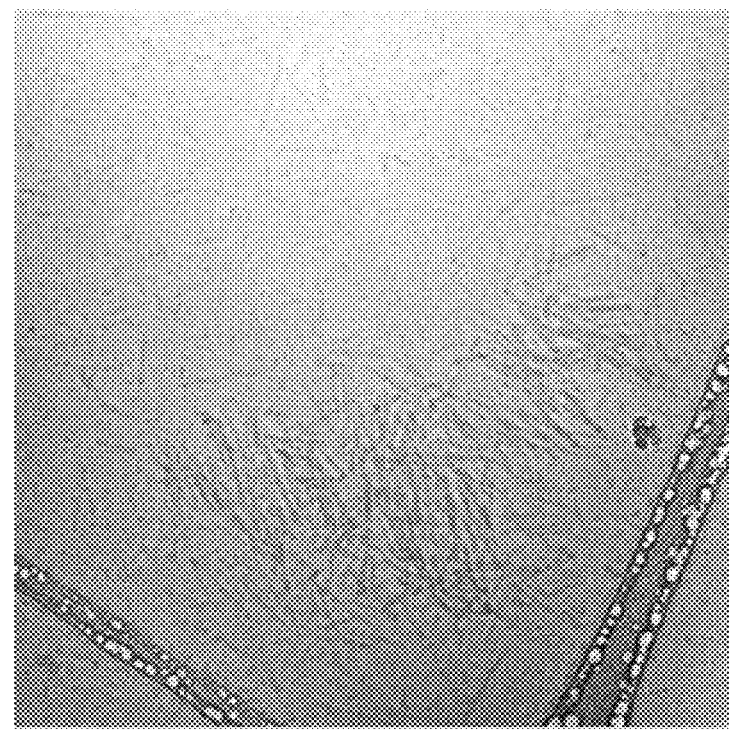

The 10% MMP- and ROS-Ac2-26 PAs were further characterized for their physical structure, charge, and stability. Using small angle x-ray scattering (SAXS), the intensity versus the scattering vector of the Guinier regime in the low q region was examined. The slope was −1.6 for 10% ROS-Ac2-26 PAs and −1.8 for 10% MMP-Ac2-26 PAs (FIG. 11A, 11B). A slope of −1 is observed for E2 filler PA and indicates a cylindrical shape while a slope of −2 is associated with lamellar structures. As a result, the ApoA1-Ac2-26 PAs could be interpreted as flattened, elongated structures; a mixture of flattened and cylindrical structures, or two cylindrical shapes stacked atop each other. Fitting the SAXS data to a polydisperse core-shell cylinder model, a similar core radius (1.8 vs. 2.1 nm) and radial shell thickness (2.2 vs. 2.0 nm) was found for the 10% ROS-Ac2-26 PA and 10% MMP-Ac2-26 PAs, respectively (FIG. 12A-12B). In addition, both the 10% MMP-Ac2-26 and 10% ROS-Ac2-26 PA nanofiber structures were not disrupted by serum proteins, as shown by cryogenic TEM images after reconstitution in solution containing 10% fetal bovine serum, providing support for their stability upon intravenous injection (FIG. 12C-12D).

Figure 13A:
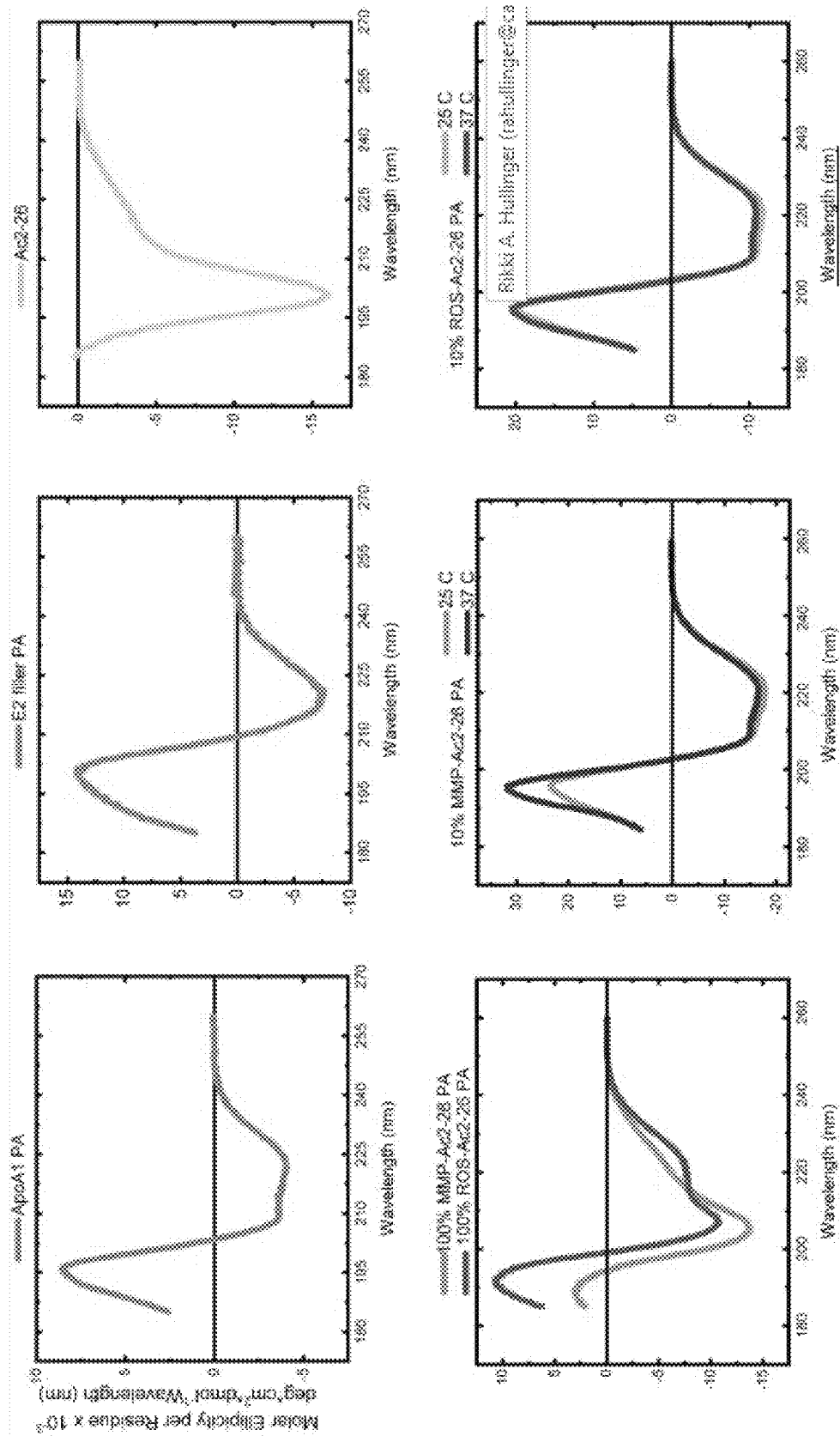
Figure 13B:
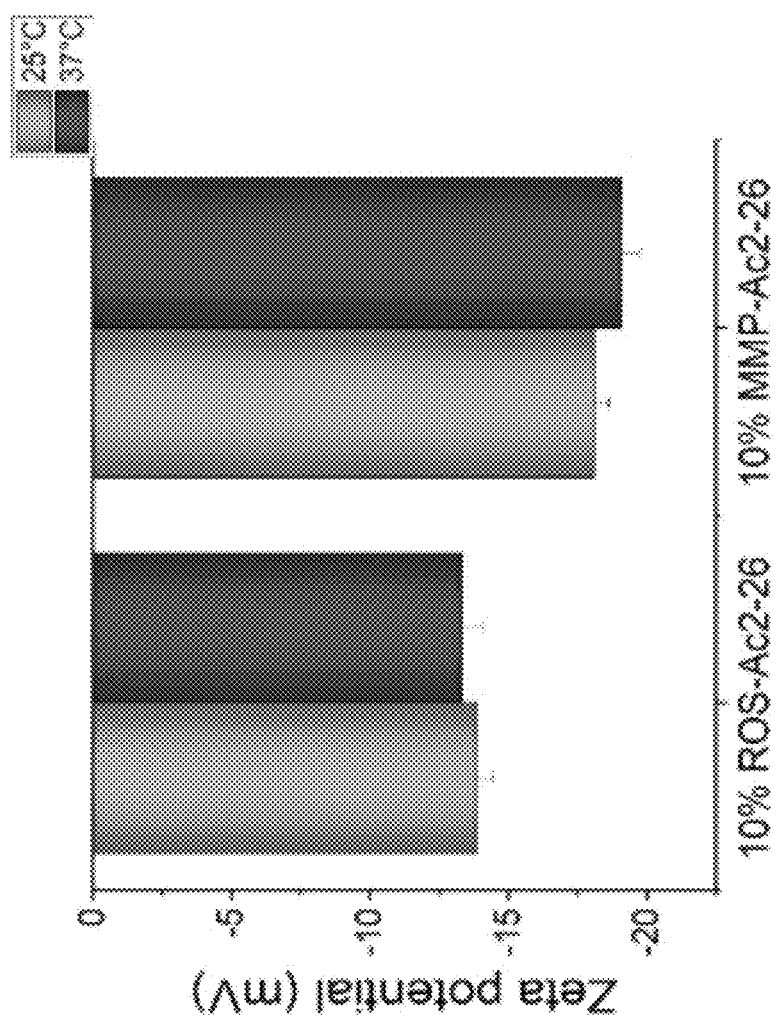
Figure 13C:
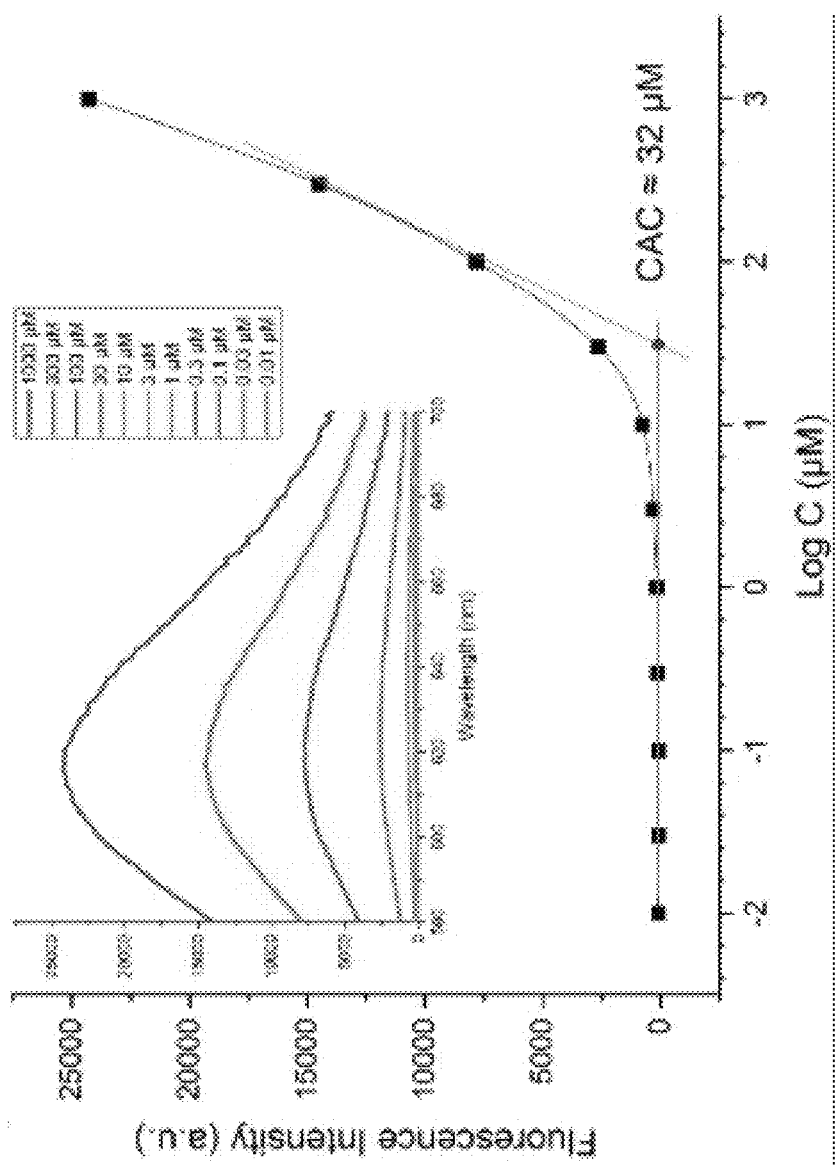
Figure 13D:
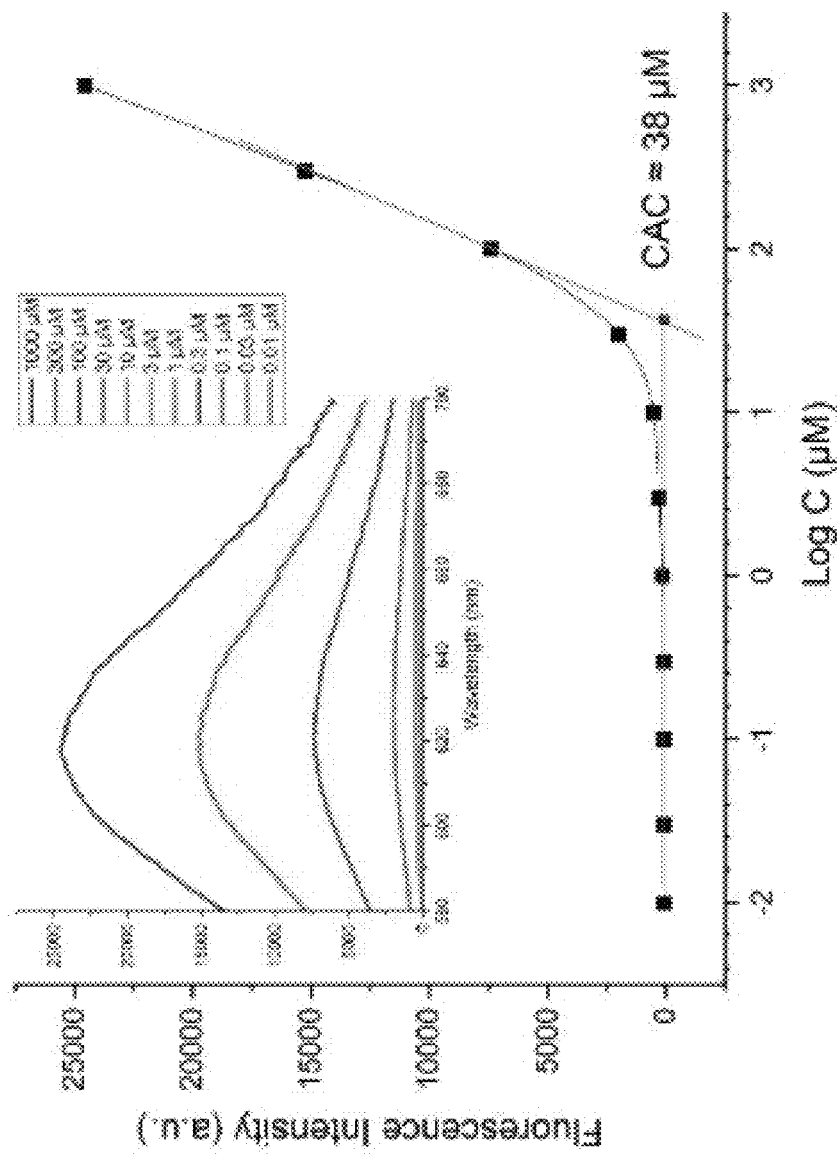

Given the importance of the α-helical character of ApoA1 for lipid binding, the secondary structure of MMP- and ROS-ApoA1-Ac2-26 PA nanofibers was examined using circular dichroism spectroscopy. The MMP- and ROS-ApoA1-Ac2-26 PAs retained the α-helical character of the ApoA1 PA at both room temperature (25° C.) and physiological temperature (37° C., FIG. 13A). In contrast, the E2 filler PA had dominant β-sheet character, as expected, while the Ac2-26 peptide and MMP- or ROS-Ac2-26 PAs exhibited random coil secondary structure. The 10% ROS-Ac2-26 PAs had a negative overall charge of −13.9±0.6 mV at 25° C. that was maintained at 37° C., and the 10% MMP-Ac2-26 PAs also had a negative overall charge of −18.1±0.5 mV at 25° C. that was maintained at 37° C. (FIG. 13B). The 10% MMP-Ac2-26 PAs are expected to be more negatively charged than the 10% ROS-Ac2-26 PAs due to the greater number of negatively charged residues in the MMP2/9-cleavable linkage than the oligoproline linkage. To predict whether the PAs would maintain nanofiber structure upon dilution in the bloodstream, a Nile Red Assay was performed to determine the critical aggregation concentration (CAC). The CAC was near 32 µM and 38 µM for the 10% MMP-Ac2-26 and 10% ROS-ApoA1-Ac2-26 PAs, respectively (FIG. 13C). This concentration is 25-fold lower than the injection concentration of PAs, and beyond the 20-fold dilution expected for PA dilution in the bloodstream.

Figure 14A:
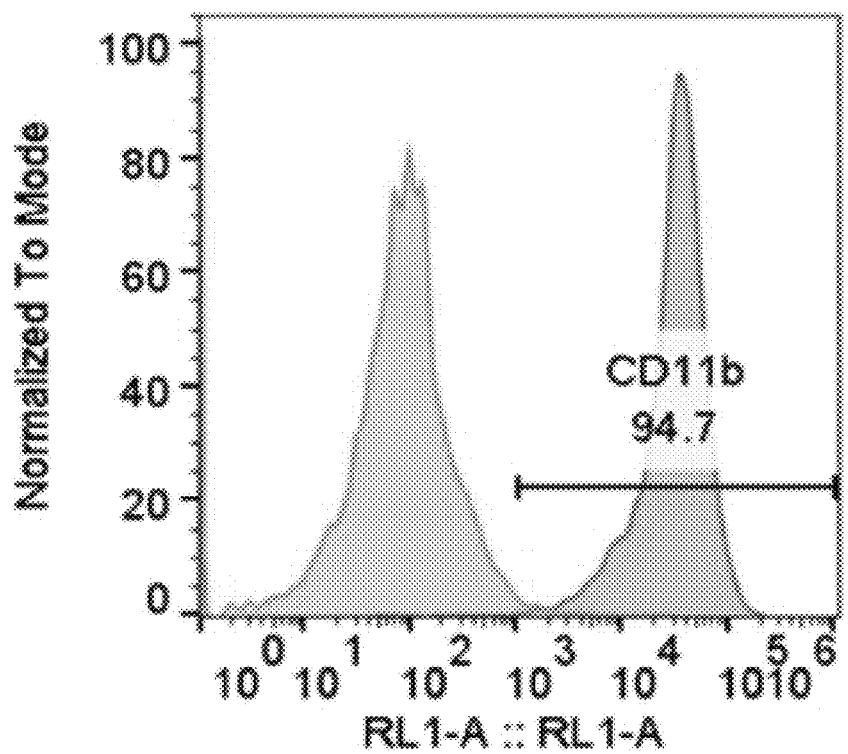
FIG. 14A-14D. Representative histograms from flow cytometry characterization of J774.2 macrophages for expression of (FIG. 14A) CD11b, (FIG. 14B) formyl peptide receptor 2 (FPR2), and inducible nitric oxide synthase (iNOS) before (FIG. 14C) and after (FIG. 14D) stimulation with 100 ng/mL IFN-7 and 10 µg/mL LPS. The blue histograms represent the fluorophore control, hamster IgG conjugated to APC.
Figure 14B:
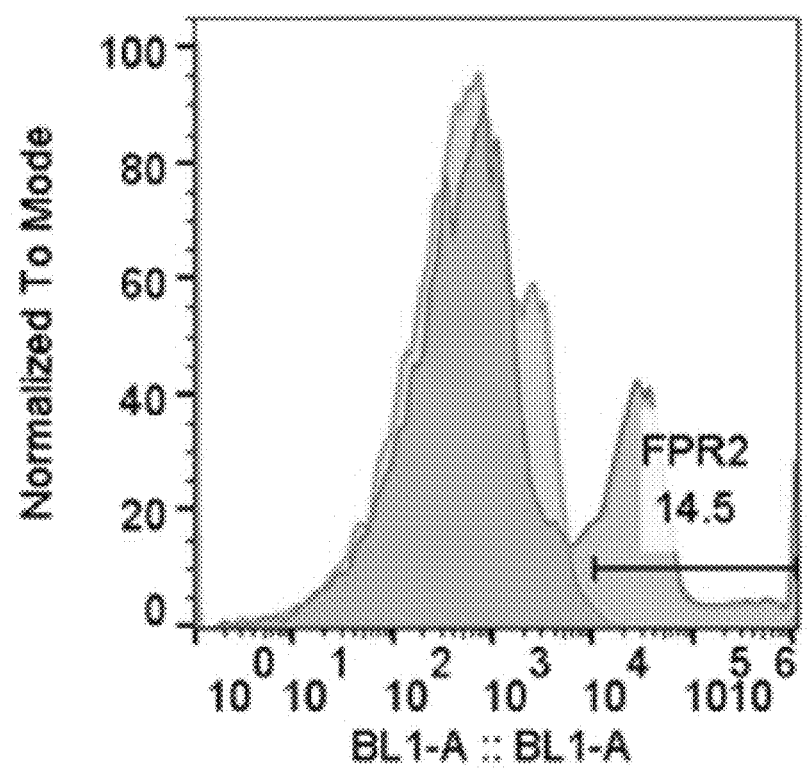
Figure 14C:
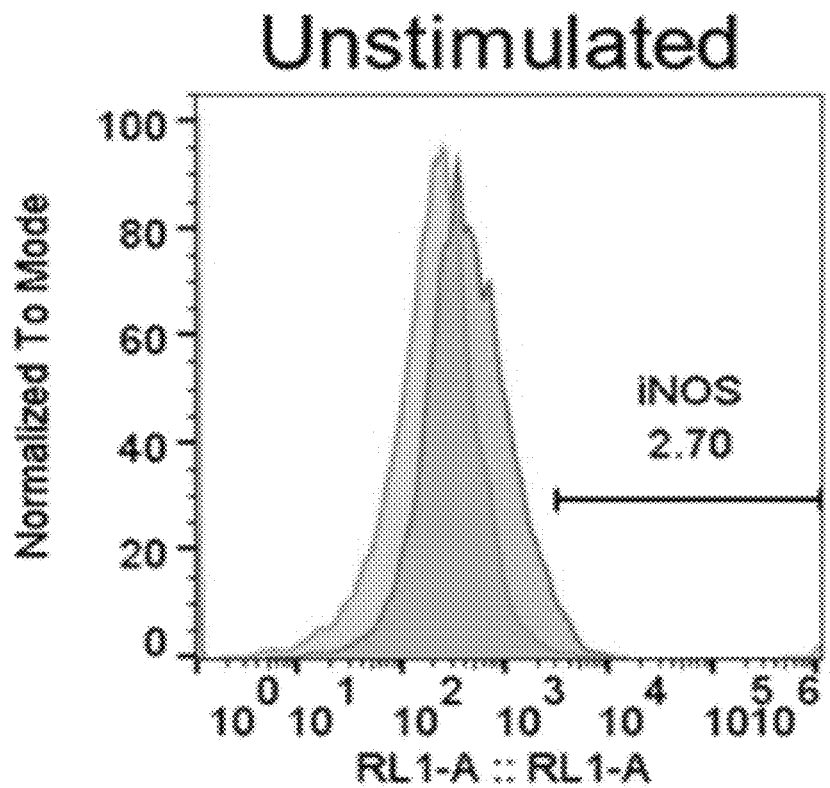
Figure 14D:
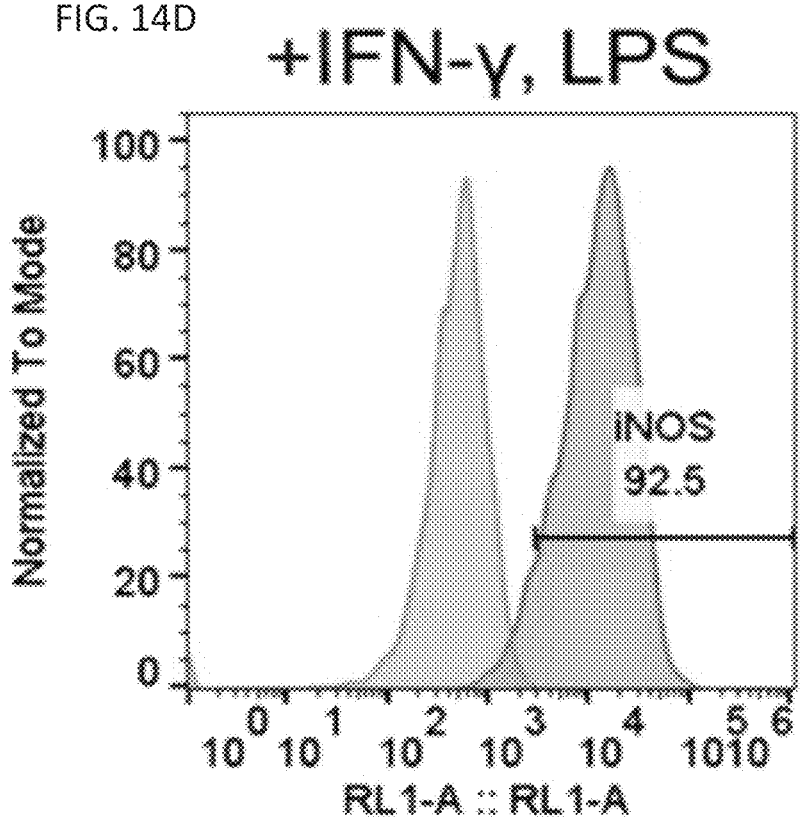
Figure 15:
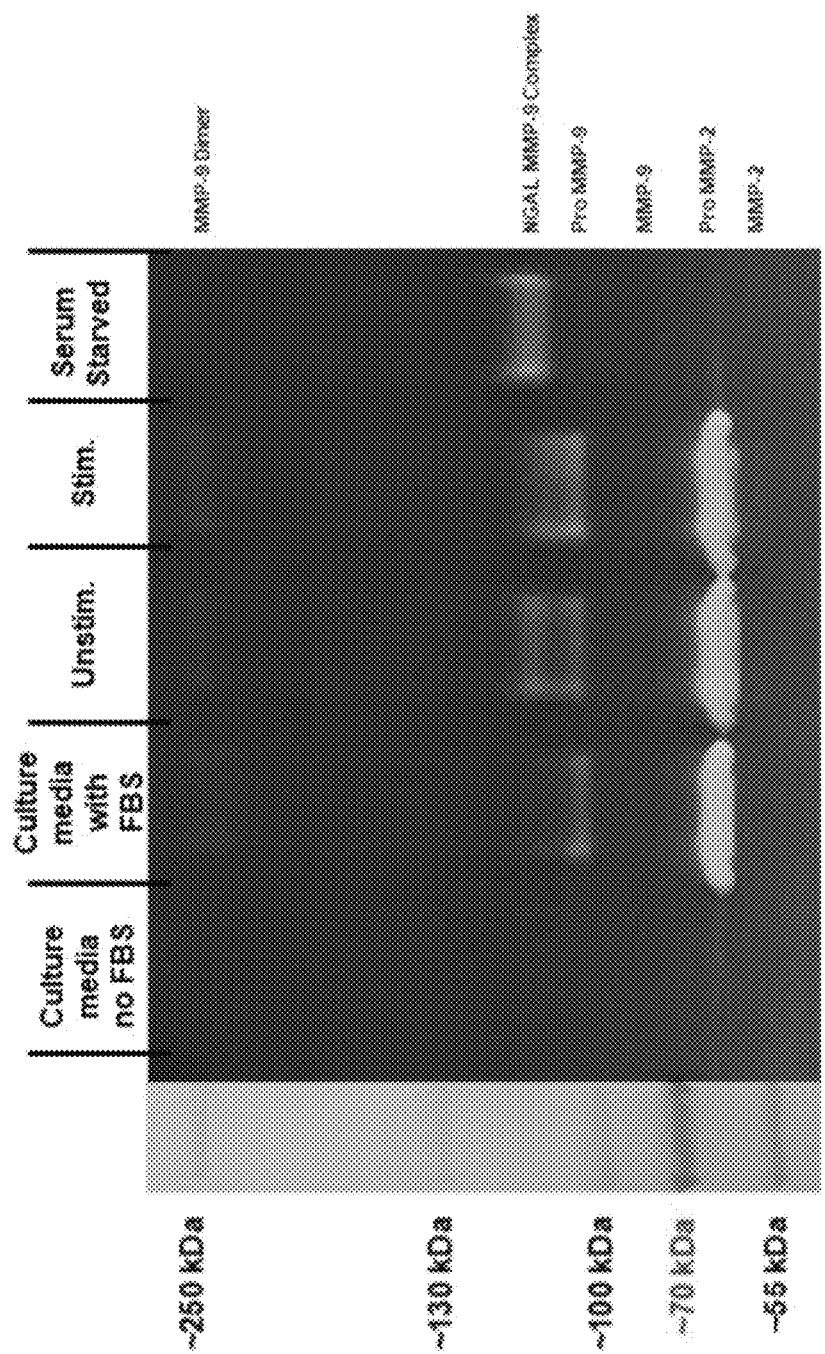
FIG. 15. Zymography gel characterization of J774.2 macrophages. Left to right: culture media without cells or FBS, culture media with FBS and without cells, unstimulated macrophages in culture media with FBS, macrophages stimulated by 100 ng/mL IFN-7 and 10 µg/mL LPS in culture media with FBS, unstimulated macrophages in media without FBS.

ApoA1-Ac2-26 PA cytocompatibility and therapeutic potential: Based on the critical role of macrophages in driving inflammation-mediated progression of atherosclerosis, a murine macrophage cell line, J774.2, was used to assess the cytocompatibility and therapeutic effects of ApoA1-Ac2-26 PAs. The macrophages expressed >90% of CD11b, a pan-macrophage marker, and 14.5% of FPR2, the target ligand for Ac2-26 (FIG. 14A-14B). The potential for the macrophages to produce ROS was confirmed by >90% iNOS expression after overnight treatment with 100 ng/mL IFN-7 followed by 24 hours of treatment with 10 µg/mL lipopolysaccharide (LPS, FIG. 14C-14D). MMP2/9 production from J774.2 macrophages was confirmed using zymography (FIG. 15).

Figure 16A:
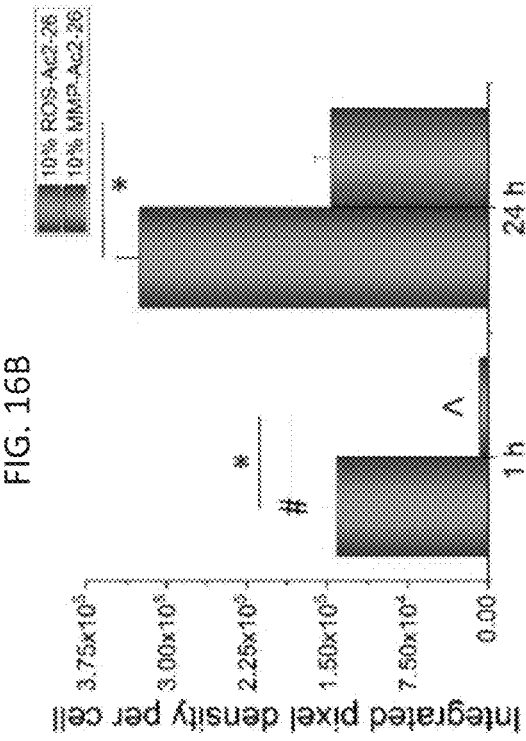
FIG. 16A-D. Cytocompatibility and cellular uptake characterization of ApoA1-Ac2-26 PAs.
Figure 16B:
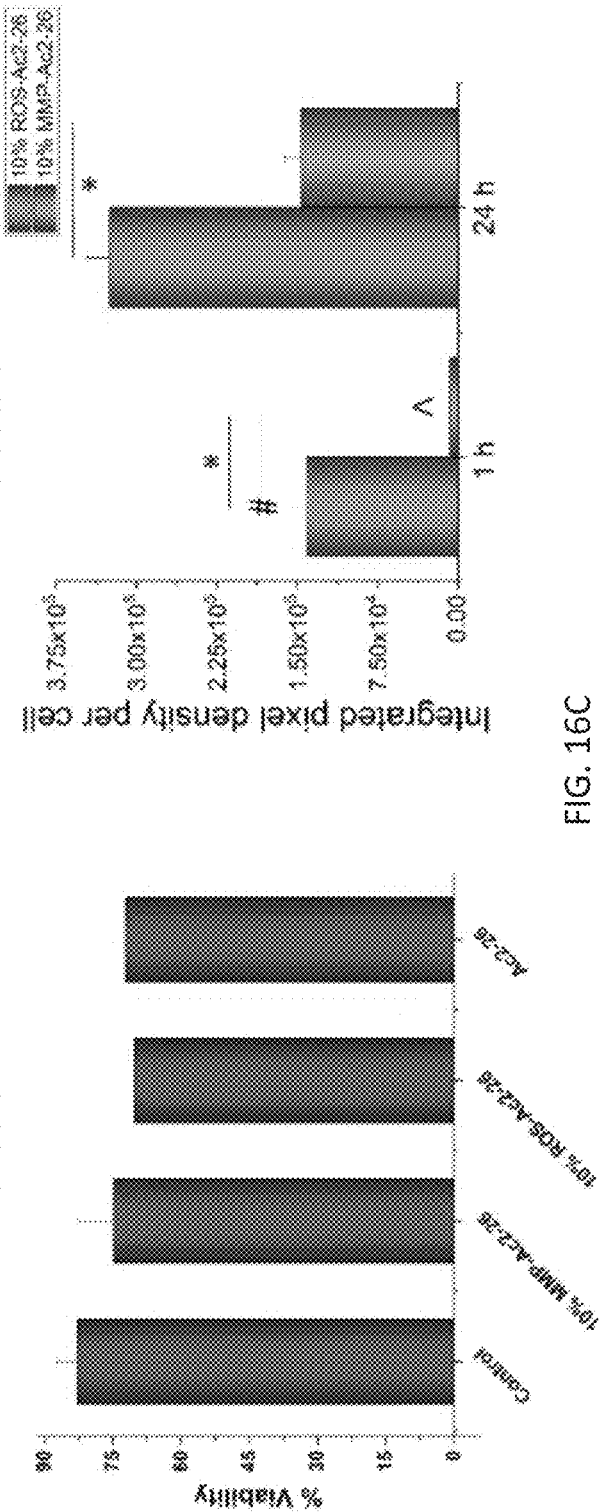
Figure 16C:
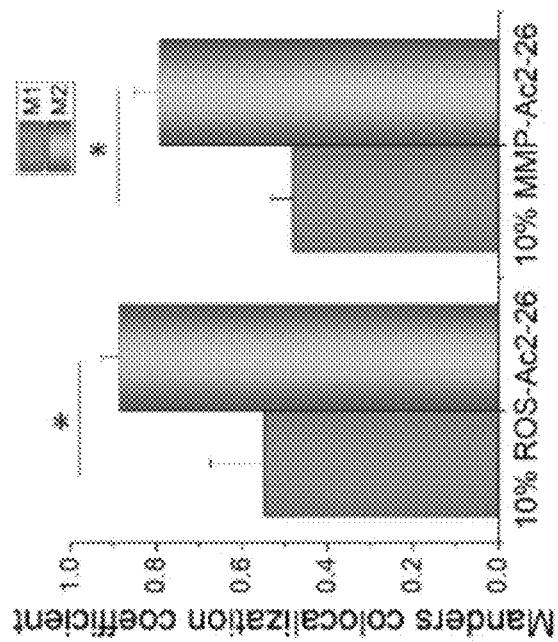
Figure 16D:
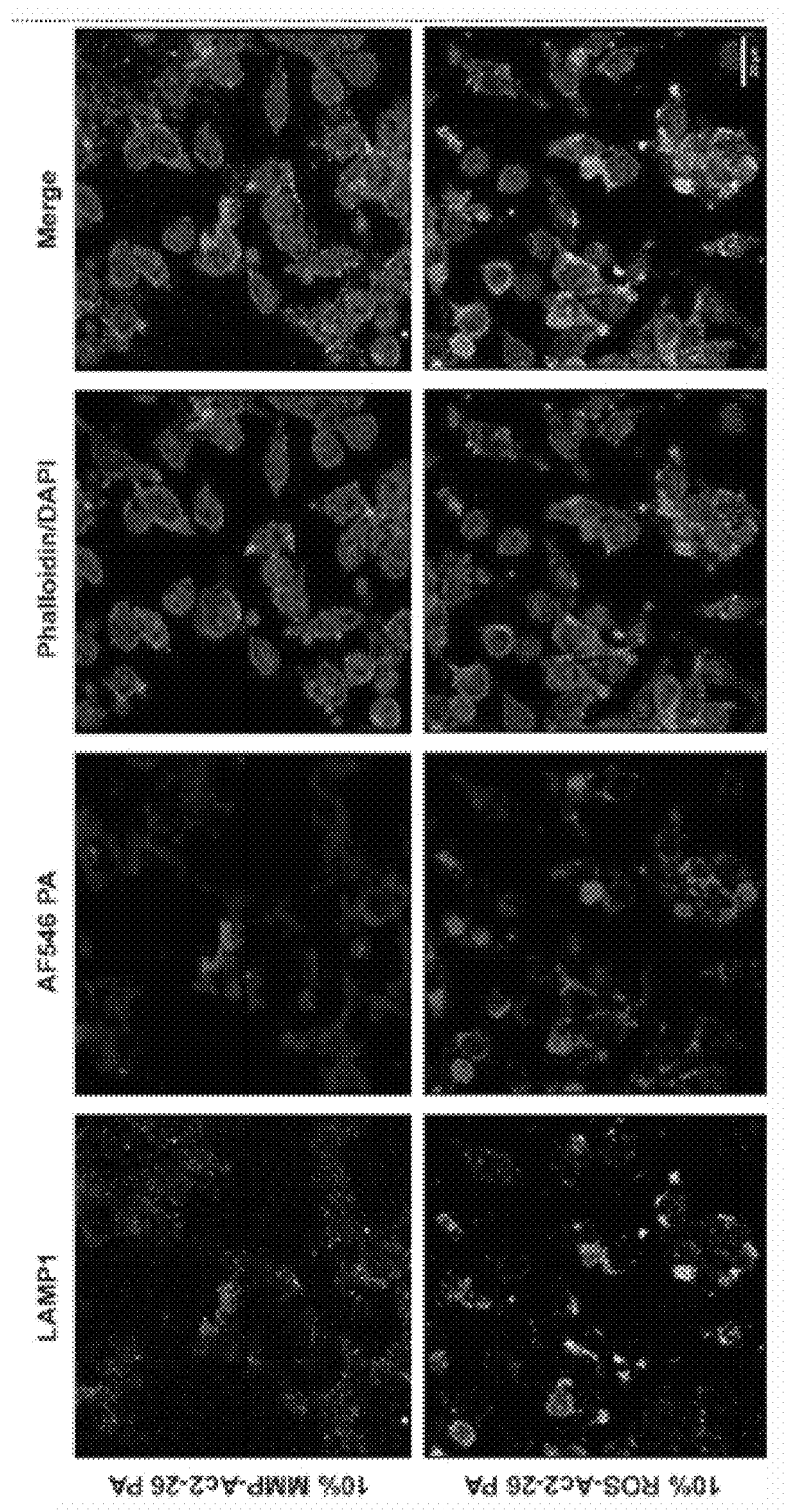
Figure 17:
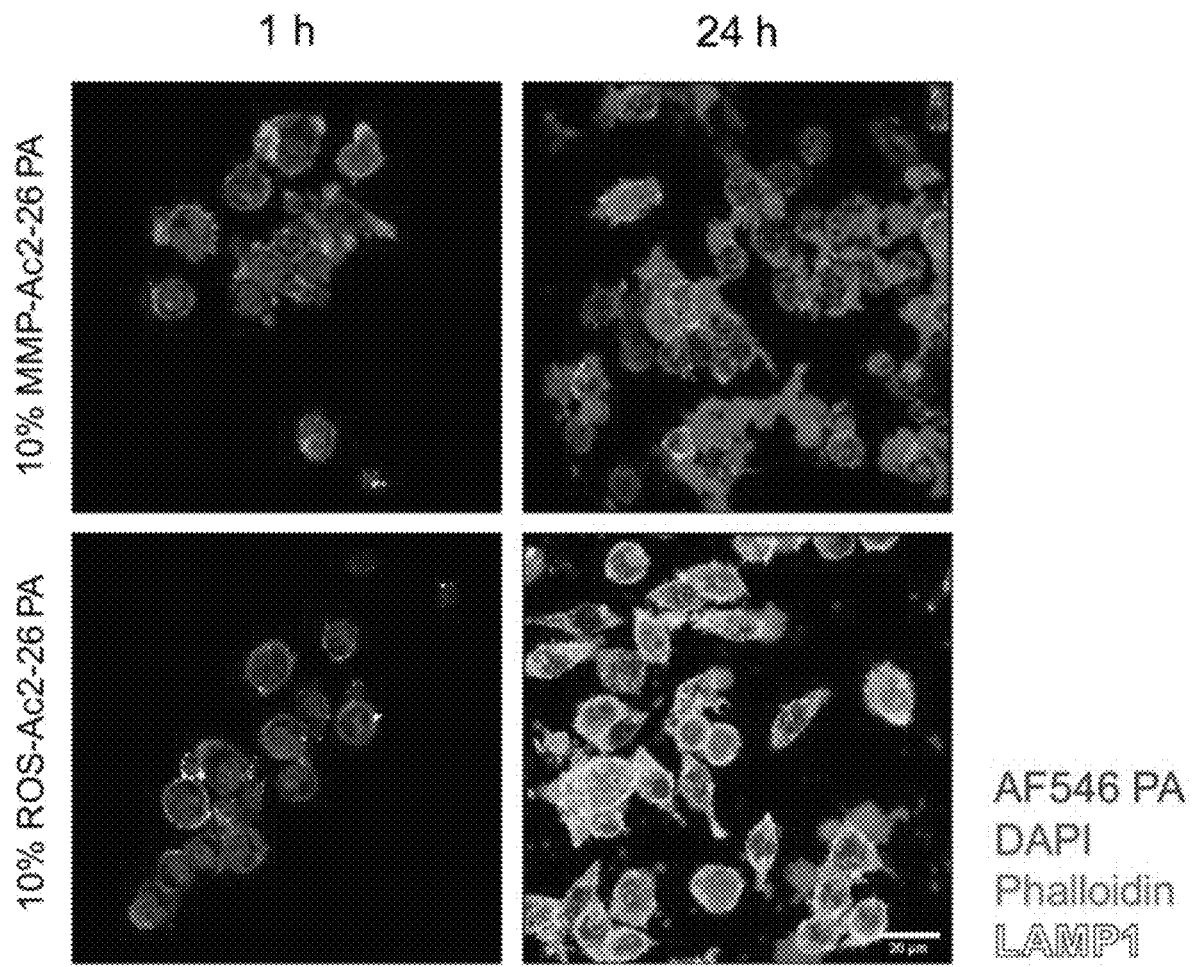
FIG. 17. 3D projection of confocal images analyzing cellular uptake of ApoA1-Ac2-26 PAs after 1 and 24 hours of treatment. Scale bar equals 20 µm.

ApoA1-Ac2-26 PAs effects upon cell viability were assessed through a MUSE® Count and Viability Assay Kit, which utilizes fluorescence to indicate cell membrane barrier function. Neither the 10% MMP-Ac2-26 PAs nor 10% ROS-Ac2-26 PAs showed significant cytotoxicity (p>0.6) in comparison to the untreated or Ac2-26 peptide controls after 24 hours of treatment (FIG. 16A). Interestingly, the rate and extent of PA uptake varied with linker sequence, with the ROS-cleavable PAs demonstrating a near 18-fold increase in cellular uptake in comparison to MMP-cleavable PAs after one hour of treatment (FIG. 16B, FIG. 17) (While PA uptake was significantly increased for both 10% MMP- and ROS-Ac2-26 PAs after 24 hours, the ROS-cleavable PAs maintained a significant 2-fold increase in comparison to the MMP-cleavable PAs. Further, the ROS-cleavable PAs were retained within the cell whereas the majority of the MMP-cleavable PAs were found in the extracellular space. Both MMP- and ROS-cleavable ApoA1-Ac2-26 PAs were processed in the endosomal or lysosomal compartments based on colocalization to lysosomal-associated membrane protein 1 (LAMP1, FIG. 16C-16D). The average Manders coefficient values for PA to LAMP1 vs. LAMP1 to PA colocalization were 0.55 and 0.89 for 10% ROS-Ac2-26 PAs and 0.48 and 0.79 for 10% MMP-Ac2-26 PAs. These results indicate that while half of the PAs are being processed within lysosomal or endosomal compartments, the other half may be localizing to other intracellular compartments or were recycled from the endosome/lysosome to the cellular membrane or extracellular space. Taken together, these results indicate that the ROS- and MMP2/9-cleavable linker chemistry affects macrophage uptake and retention of ApoA1-Ac2-26 PAs and may also cause differences in lysosomal or endosomal processing.

Figure 18B:
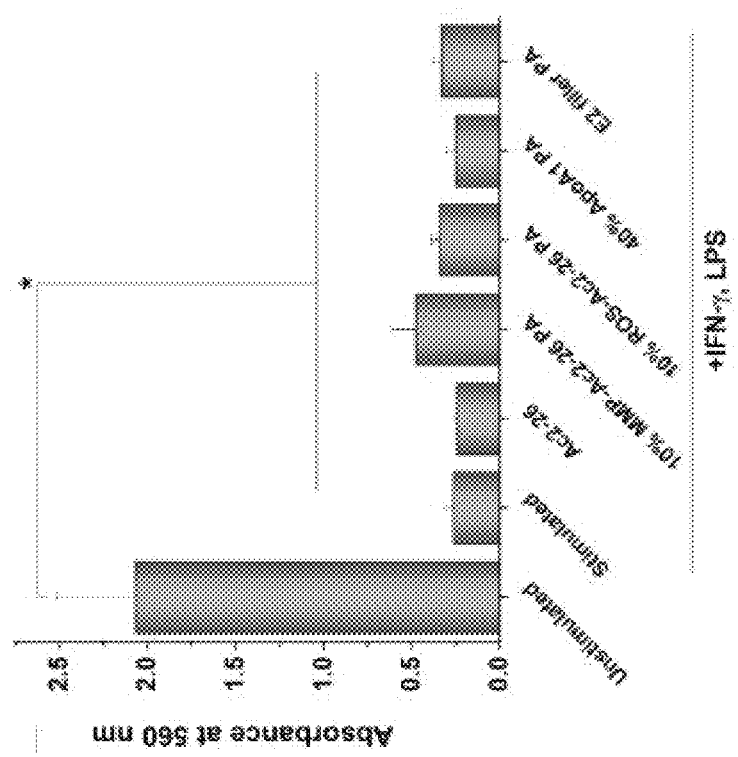
FIG. 18A-18D. Analysis of ApoA1-Ac2-26 PA effects upon macrophage activation and metabolic activity.
Figure 18A:
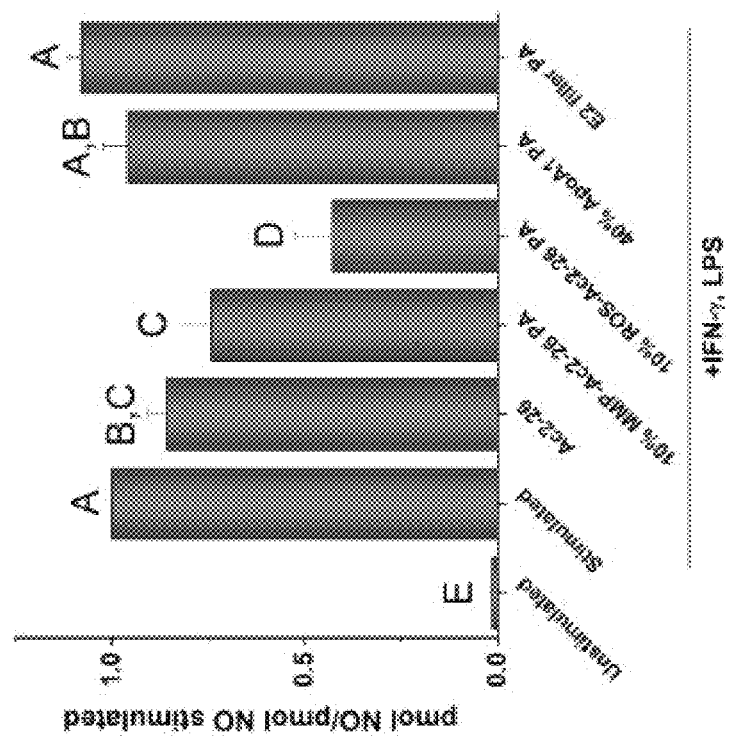

To determine whether the Ac2-26 peptide maintained its pro-resolving potential upon cleavage from PAs, an in vitro assay was used to simulate the pro-inflammatory macrophages characteristic of the atherosclerotic niche. After 24 hours of treatment with Ac2-26, 10% MMP-Ac2-26, or 10% ROS-Ac2-26, macrophage activation by LPS and IFN-7 was significantly reduced (p=0.0207, p=0.0005, p<0.0001, respectively) based upon decreased nitric oxide production relative to the stimulated control (FIG. 18A). Further, the 10% ROS-Ac2-26 PA caused significantly greater effects on decreased nitric oxide production in comparison to 10% MMP-Ac2-26 PA (p=0.0002) and Ac2-26 (p<0.0001) treatments. The additional PAs in the 10% MMP- and ROS-Ac2-26 PA co-assemblies-ApoA1 PA and E2 filler PA did not cause significant decreases in nitric oxide production in comparison to the stimulated control (p=0.5534, p=0.2606, respectively), indicating that the MMP- or ROS-cleavable Ac2-26 PAs were responsible for the therapeutic effects. While stimulating the macrophages with LPS and IFN-7 significantly reduced cell metabolic activity (p<0.0001), as measured by NAD(P)H-dependent oxidoreductase enzyme activity through an MTT assay, the Ac2-26 peptide and PA treatments did not significantly affect cellular metabolism in comparison to the stimulated control (p>0.37, FIG. 18B).

Figure 18D:
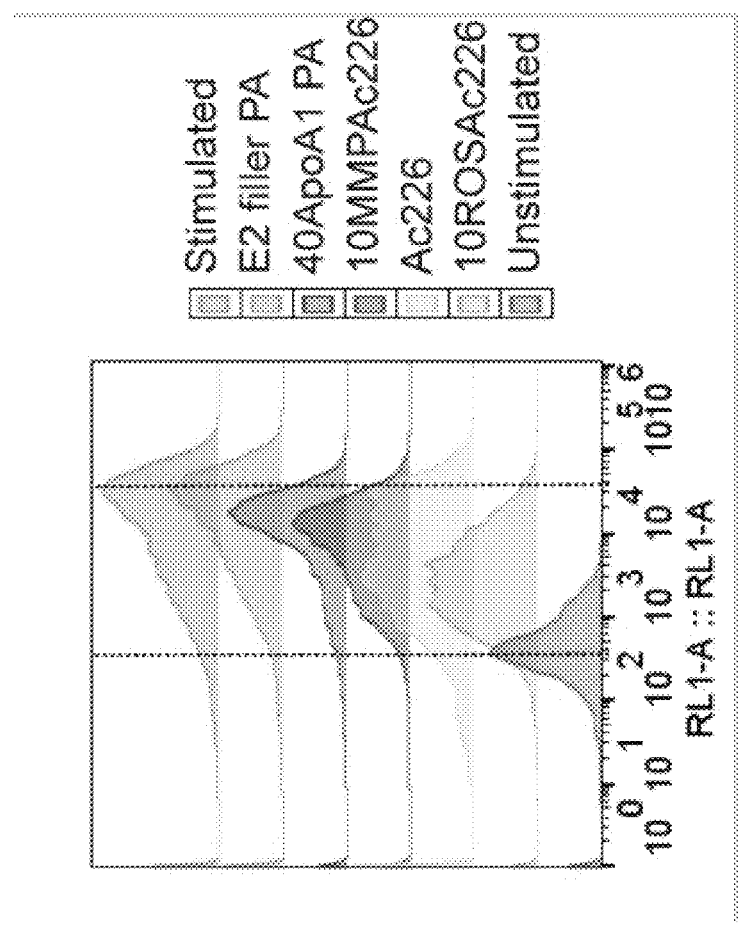
Figure 18C:
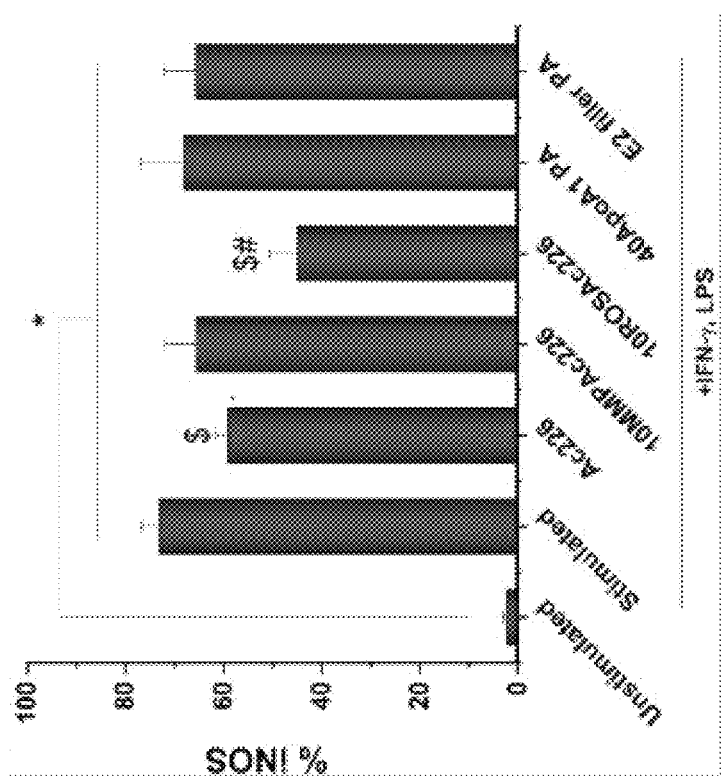

In addition, treatment with 10% ROS-Ac2-26 PAs decreased intracellular iNOS expression of stimulated macrophages (p=0.0022) to a similar extent as the Ac2-26 peptide (p=0.3075, FIG. 18C-18D). In contrast, the 10% MMP-Ac2-26 PA had no effect upon iNOS expression in comparison to the stimulated control (p=0.2970). A potential explanation for the enhanced therapeutic effect of the 10% ROS-Ac2-26 PAs in comparison to the 10% MMP-Ac2-26 PAs is faster cleavage and corresponding release of Ac2-26 due to the increased production of ROS from macrophages under stimulating conditions. In addition, the enhanced cellular uptake and retention of the 10% ROS-Ac2-26 PAs versus the 10% MMP-Ac2-26 PAs may provide additional pathways for Ac2-26 to decrease pro-inflammatory macrophage activation. For example, Liu et al. recently Ac2-26 may induce anti-inflammatory effects within the cytosol of microglia cells by affecting the small molecular chaperone heat shock factor-binding protein 1 (HSPB1) binding to IKKO, ultimately causing its degradation to reduce TNF-α expression, which positively regulates iNOS expression.

In conclusion, disclosed herein is a bioresorbable nanocarrier with the potential to target atheroma and provide controlled immunotherapeutic delivery to the atherosclerotic niche. The pro-resolving peptide Ac2-26 can be conjugated to a PA and multiplexed with additional PAs to create a nanocarrier with the potential to target atherosclerotic plaque. The release of Ac2-26 is controlled by peptide linkages that cleave in response to endogenous signals overexpressed in the plaque microenvironment—MMP2 and ROS. The released Ac2-26 maintained its bioactivity to reduce macrophage activation towards a pro-inflammatory phenotype within 24 hours of treatment.

Example 3

Peptide Amphiphile Supramolecular Nanostructures as a Targeted Therapy for Atherosclerosis Apolipoprotein A1 (ApoA1) is the main protein component of high density lipoprotein (HDL) cholesterol and is capable of promoting cholesterol efflux from atherosclerotic plaques in animals. However, since ApoA1 is a large and hydrophobic protein (21-31 kDa), synthesis and incorporation into a therapeutic agent is impractical. Instead, the approach described herein was to target atherosclerotic plaque by covalently bonding to PAs an 18 amino acid ApoA1 mimetic peptide, known as "4F". This peptide is approximately ¹/₁₀th the size of endogenous ApoA1, making it easier to synthesize and incorporate into nanomaterials, while also retaining the cholesterol efflux and binding actions of ApoA1 in animals. The ability of 4F to bind to oxidized lipids is particularly useful since the increased presence of oxidized lipids correlates with atherosclerotic severity. The dissociation constant of 4F for the oxidized phospholipid PEIPC (1-palmitoyl-2-(5,6-epoxyisoprostane E2)-snglycero-3-phosphorylcholine) was discovered to be over six orders of magnitude lower than that of native ApoA1-PEIPC binding (0.01 nM vs. 50 µM), indicating much higher affinity between the oxidized lipid and 4F than between the lipid and ApoA1 protein. Furthermore, D-4F (4F synthesized with all D-amino acids) increases HDL-mediated cholesterol efflux from human macrophages in vitro and enhances reverse cholesterol transport from cholesterol-rich macrophages injected intraperitoneally into ApoE knockout mice. Thus, the 4F peptide was incorporated into PAs to generate a plaque-targeting nanocarrier platform, ApoA1 PA.

Synthesis and characterization of targeted peptides, targeted nanofibers and therapeutic nanofibers: PA molecules were synthesized using 9-fluorenyl methoxycarbonyl (Fmoc) solid-phase peptide chemistry with low-loading Rink amide 4-methylbenzhydrylamine resin. Synthesis was performed on a CEM Liberty or CEM Liberty Blue automated microwave peptide synthesizer. Coupling reactions on the Liberty were performed using 4 molar equivalents (eq.) of Fmoc-protected amino acid or palmitic acid; 4 eq. of O-benzotriazole-N, N, N', N'-tetramethyluronium hexafluorophosphate (HBTU); and 8 eq. of N,N-diisopropylethylamine (DIEA); and removal of Fmoc groups on resin-attached amino acids was achieved with 30% 4-methylpiperidine and 0.1 µM hydroxybenzotriazole (HOBt) in N,N-dimethylformamide (DMF). Coupling reactions on the Liberty Blue were performed using 4 eq. of Fmoc-protected amino acid or palmitic acid; 4 eq. of N,N-diisopropylcarbodiimide (DIC); and 8 eq. of ethyl(hydroxyimino)cyanoacetate (Oxyma pure); and removal of Fmoc groups on resin-attached amino acids was achieved with 20% 4methylpiperidine in DMF.

Covalent attachment of GW3965 to peptides was achieved by direct conjugation of the carboxylic acid of GW3965 to the N-terminal amine of the peptide on resin using 1.2 eq. GW3965-HCl, 1.1 eq. HBTU, and 8 eq. DIEA. PAs and peptides were cleaved off resin in a 95:2.5:2.5 trifluoroacetic acid (TFA)/triisopropylsilane (TIPS)/$H_2O$ mixture (cysteinecontaining peptides included 3% 2,2'-(Ethylenedioxy)diethanethiol (DODT) and 92% TFA with the same TIPS/$H_2O$ mixture). Purification was accomplished using HPLC on a C18 Phenomenex Gemini column in a water-acetonitrile gradient containing 0.1% v/v $NH_4OH$. Fractions with the desired product were identified using electrospray ionization mass spectrometry and combined. Rotary evaporation followed, and after removal of volatile solvents, the resulting product was lyophilized to dryness. Fluorophore labelling was achieved by reacting PA/peptide in 2-3× molar excess with Alexa Fluor® 546-C5maleimide and Tris(2-carboxyethyl)phosphine (TCEP) hydrochloride (5 eq. with respect to PA/peptide) in pH 8 Tris buffer or potassium phosphate buffer pH 7.8. Pure product was isolated following HPLC purification as described above.

Alexa-tagged PA/peptide was present at 10 wt % concentration in the final co-assembly as described below. PA/peptide co-assemblies and LXR agonist-encapsulations were prepared using a solvent evaporation method. Briefly, each component of the co-assembly or encapsulation was dissolved in 1,1,1,3,3,3-hexafluoro-2-propanol (HFIP). For 40% ApoA1 PA co-assembly, solutions of the ApoA1 PA (sequence: C16-$V_2A_2$ (SEQ ID NO: 8)-$E_2$-G-DWFKAFYDKVAEKFKEAF (SEQ ID NO: 2)-$NH_2$) and diluent PA (sequence: $C_{16}$-$V_2A_2$ (SEQ ID NO: 8)-$E_2$-$NH_2$) were mixed at a 40 mol % ApoA1 PA/60 mol % diluent PA ratio. Similarly, the 40% scrambled ApoA1 sequence PA co-assembly (Scr PA) was made with a 40 mol % Scr PA (sequence: $C_{16}$-$V_2A_2$ (SEQ ID NO: 8)-$E_2$-C-DW-FAKDYFKKAFVEEFAK (SEQ ID NO: 9)-$NH_2$)/60 mol % diluent PA ratio. Coassemblies with Alexa fluorophore had 10 wt % Alexa-tagged ApoA1 or Scr PA, with the 40 mol % concentration of respective PA maintained. LXR agonist-encapsulations were made by adding HFIP-dissolved GW3965 to the appropriate PA mixture in a 1:1 wt. LXR/PA ratio. After component solutions were combined, the mixtures were sonicated in a water bath for 15 minutes, frozen in liquid nitrogen, and kept under vacuum until dry. The resulting materials were then reconstituted in ultrapure water, pH-adjusted with 200 mM NaOH to dissolution, probe-sonicated for 30 seconds, and lyophilized to dry powder. Peptide sequences are shown in Mansukhani et al., Macromolecular Bioscience (2019) 19: 6, the entire contents of which are incorporated herein by reference.

PA characterization: PA and peptide secondary structure was investigated using a Chirascan™-plus Circular Dichroism Spectrometer (Applied Photophysics). Samples were analyzed at 0.5 mM, with respect to ApoA1 or Scr PA in co-assemblies, in 0.1 µM phosphate buffer at pH 7.4 with a 0.1 mm pathlength Suprasil® quartz cuvette (Sigma-Aldrich). Each sample was analyzed at 25° C. and 37° C. using a wavelength spectrum of 185 to 260 nm with a step of 0.3 nm and analysis time of 1.25 seconds per data point. Spectrum data was averaged from two scans and the phosphate buffer values were subtracted from each sample. Predictions of secondary structure fractions in ApoA1 PA before and after LXR addition were performed using CD spectral data at 37 C using CDPro software package. The predicted results from CONTIN, SELCON3, and CDSSTR methods were averaged for each PA.

Dynamic light scattering measurements were performed on a Zetasizer Nano ZS instrument (Malvern). Samples were prepared at 0.1 to 1 mM in PBS and passed through a 0.1-0.2 µm pore size Whatman™ syringe filter using a 1 mL Monoject™ insulin syringe. The mean count rate was averaged from three runs per experiment, with 12-32 scans per run.

Samples at 1 mM in PBS were prepared for TEM by plating on copper supports covered with thin carbon foil 400-mesh that were treated with glow discharge. Samples were adsorbed on the grid for approximately two minutes, rinsed with water, and stained with 2% uranyl acetate before imaging on a FEI Tecnai T-12 TEM at 80 kV with a Gatan Orius® 2 k×2 k CCD camera. Due to the overlapping fibers, automated tools including FiberApp could not be used to analyze the nanofibers. Instead, the TEM images were analyzed manually for nanofiber diameter and length using ImageJ software. Cryogenic TEM of samples was also performed using a JEOL 1230 at 100 kV accelerating voltage and Gatan 831 CCD camera. PAs were pipetted at 5.0 L volumes onto 300-mesh copper grids with lacey carbon support (Electron Microscopy Sciences) that were pretreated with glow discharge for 20 seconds. Samples were prepared at 1 mM in PBS blotted once for 3 seconds before plunging into liquid ethane using a Vitrobot Mark III (FEI) vitrification robot. After vitrification, the samples were transferred under liquid nitrogen to a Gatan 626 cryo-holder for imaging.

Mouse model of atherosclerosis: To study atherosclerosis, the LDLR KO mouse was used. LDLR KO mice are fed a high fat "western" diet (Teklad TD.88137) starting at 4 weeks of age. This diet consists of 20% fat, 0.2% cholesterol, and 34% high sucrose. LDLR KO mice fed this diet typically develop severe hypercholesterolemia (>800 mg/dL) and hypertriglyceridemia (>300 mg/dL) after only 2 weeks. By 12 weeks on the high fat diet, atherosclerotic lesions are detected in the aortic root and aortic arch on cryosections stained with Oil Red O (Sigma). Atherosclerosis was quantified in the aortic root as a percentage of the aortic root by taking the atherosclerotic area divided by the total aortic root area. Measurements were made with ImageJ software. All protocols for the animal model and procedures in this manuscript were approved by Northwestern University's Institutional Animal Care and Use Committee.

Injection of PA nanofibers: PA nanofibers were dissolved at 2-4 mg/mL concentration in room temperature phosphate buffered saline (PBS). After 14 weeks on the high fat diet, mice received intravenous injections of PA nanofiber dissolved in PBS (dorsal penile vein in males, retro-orbital injection in females) using a 31 G hypodermic insulin needle on a 0.3 mL syringe under sterile conditions and magnification (NIKON SMZ 645 Zoom Stereomicroscope). Mice were briefly anesthetized for injection with inhaled isoflurane. Mice were monitored and allowed to recover from anesthesia in a heated oxygen chamber.

Dose and concentration study: To determine the optimum concentration for targeting efficacy and safety, LDLR KO mice fed the high fat diet for 14 weeks were injected with PA nanofiber at concentrations of 1 mg/mL, 2 mg/mL, and 4 mg/mL at 8 mg/kg in PBS. Similarly, to determine the optimum dose for targeting efficacy and safety, LDLR KO mice fed the high fat diet for 14 weeks were injected at PA nanofiber doses of 8 mg/kg, 6 mg/kg, 4 mg/kg, 3.3 mg/kg, and 1.7 mg/kg at 2 mg/mL in PBS. Safety, optimum dose, and concentration for targeting was assessed by survival of the animal and fluorescent pixel quantification in the aortic root, liver, lungs, kidneys, and spleen.

Treatment study: LDLR KO mice fed the high fat diet for 14 weeks were briefly anesthetized with inhaled isoflurane and injected twice per week for 8 weeks with either PBS alone, the LXR agonist GW3965, ApoA1 PA, Scr PA, or ApoA1-PA with GW3965 (ApoA1-LXR PA). Injections were given at a dose of 6 mg/kg PA or 6 mg/kg PA+6 mg/kg LXR for ApoA1-LXR PA. Blood samples were collected at the end of the treatment study for toxicology analysis. Mice were euthanized three days after their 16th treatment.

Tissue processing and imaging: Mice were sacrificed and euthanized under inhaled isoflurane anesthesia by diaphragm disruption and exsanguination. Phlebotomy was performed through direct right ventricular cardiac puncture using a 1 mL syringe and 25 G needle. Perfusion was performed through left ventricular cardiac puncture with 10 mL PBS and 10 mL 10% sucrose solution. The lungs, liver, spleen, kidney, aortic root, aortic arch, and descending aorta were harvested and stored in 10% sucrose for 20 minutes. Organs and vessels were then flash-frozen in Optimal Cutting Temperature embedding medium 4583 (Tissue-Tek®)

with liquid nitrogen. Frozen specimens were stored at −80° C. and cryosectioned at 8 m. Confocal microscopy was performed on a Nikon AIR microscope. Two sets of images were acquired with a 10× Plan Fluor NA 0.3 objective. PAs were identified through quantification of the Alexa Fluor® 546 conjugated dye with 561 nm excitation and a 600/50 nm emission filter.

Images were acquired with spectral detection and spectrally unmixed to accurately separate green autofluorescence from the red Alexa Fluor® 546 signal. Brightfield and fluorescent microscopy were performed using a Zeiss Axio Imager.A2 microscope with AxioVision software (release 4.8.2, 06-2010). All confocal and fluorescent sections were mounted with ProGold Diamond mounting media (Sigma).

indicated by significantly higher molar light scattering values than peptide controls at both 25° C. ($p<0.034$) and at 37° C. ($p<0.004$), as shown in FIG. 20C. No significant differences were observed in molar light scattering between PAs or peptides at either temperature.

Figure 20D:
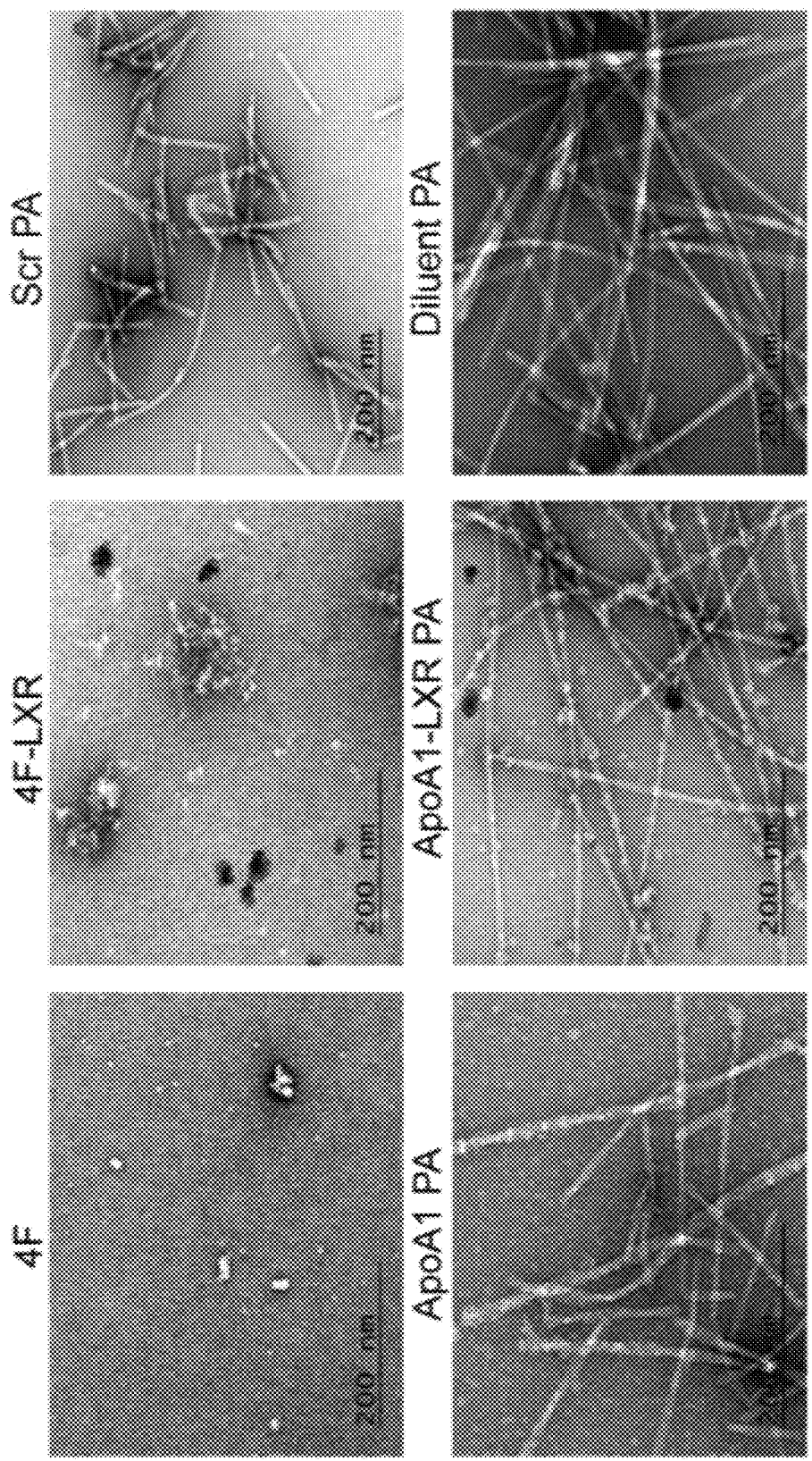
Figure 22:
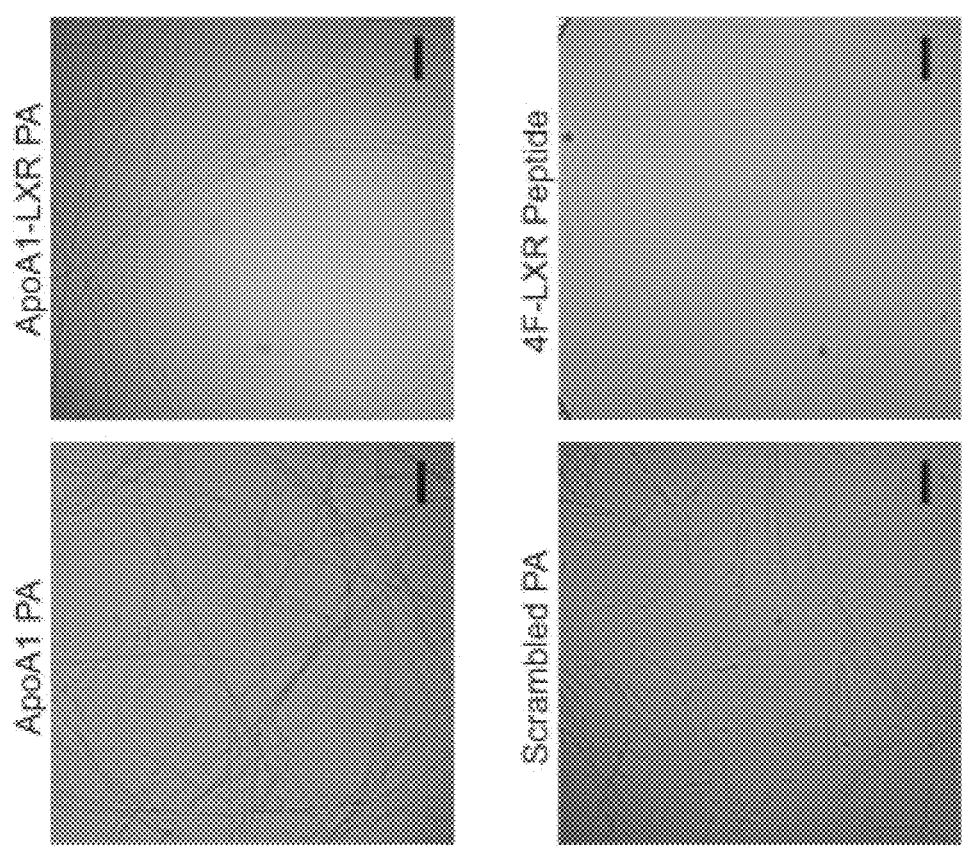
FIG. 22. Cryogenic TEM images of PAs. Scale bar equals 100 nm.

Nanofiber structure was visualized using conventional and cryogenic transmission electron microscopy (TEM, FIG. 20D FIG. 22). No nanofiber formation was seen with the 4F and 4F-LXR peptides, as expected. The average diameter for ApoA1, ApoA1-LXR, scrambled, and diluent PAs was 9.6±1.7 nm, 10.3±2.2 nm, 13.8±2.4 nm, and 12.3±3.1 nm, respectively. The median nanofiber length for ApoA1, ApoA1-LXR, scrambled, and diluent PAs was 616, 712, 258, and 2541 nm, respectively (Table 1).

TABLE 1

Characterization of PA nanofibers for diameter and length. Values represent 30 measurements taken from three separate images

| | Diameter (nm) | | | | | Length (nm) | | | | |
|---|---|---|---|---|---|---|---|---|---|---|
| | Median | Average | Std. Dev. | Min. | Max. | Median | Average | Std. Dev. | Min. | Max. |
| ApoA1 PA | 9.5 | 9.6 | 1.7 | 6.2 | 14.4 | 615.9 | 626.9 | 415.6 | 39.4 | 2183.3 |
| ApoA1-LXR PA | 10.5 | 10.3 | 2.2 | 6.4 | 16.5 | 712.1 | 832.8 | 565.5 | 148.7 | 1922.6 |
| Ser PA | 14.2 | 13.8 | 2.4 | 8.8 | 18.3 | 257.6 | 403.8 | 350.8 | 30.0 | 1472.9 |
| Diluent PA | 12.4 | 12.3 | 3.1 | 4.6 | 18.6 | 2541.4 | 3024.4 | 2554.8 | 163.3 | 9308.7 |

Slides were stained with Oil Red O to image and quantify atherosclerosis under brightfield microscopy. The elastic laminae were identified using the green fluorescent protein (GFP) filter with an exposure time of 3500 ms under 5× magnification. Nanofibers were identified in the aortic root by presence of Alexa Fluor® 546 on the Cy3 filter under 5-10× magnification, and in the internal organs under 20× magnification. Fluorescent pixel quantification in the aortic root and within organs was performed with ImageJ software.

Figure 21:
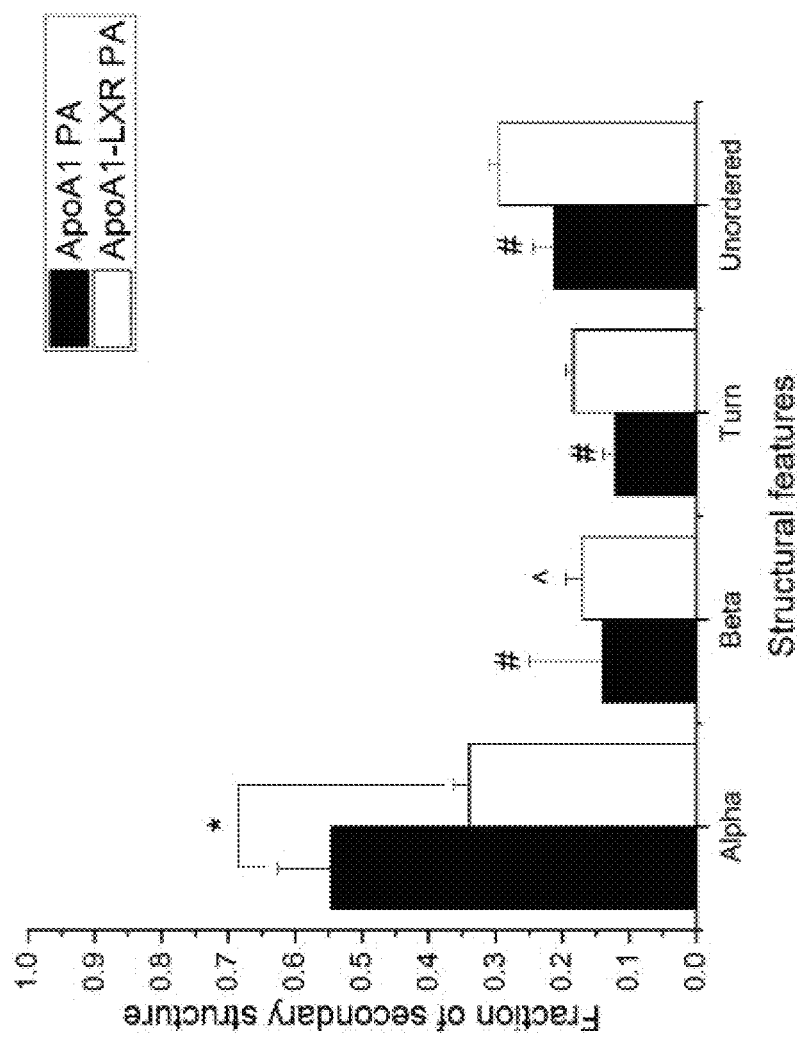
FIG. 21. Quantified predictions of secondary structure fractions for ApoA1 PA and ApoA1-LXR PA. *indicates p=0.0063, # indicates p<0.0001 vs. Alpha ApoA1 PA, ˆ indicates p=0.0432 vs. Beta ApoA1 LXR PA. Statistical analysis was performed using a two factor ANOVA followed by a post-hoc Tukey Honest Significant Difference test.

Statistics: The effect of treatments and sex on atherosclerosis progression in mice was analyzed using one- or two-factor analysis of variance (ANOVA) followed by a post-hoc student's t-test. The toxicological effects of treatments were also analyzed using two-factor ANOVA and a post-hoc student's t-test. Toxicological effects of treatments on liver proteins AST, ALT, and ALP were further analyzed using ordinal logistic regression models of likelihood ratio tests, followed by a post-hoc Wald test Results Design and characterization of PA supramolecular nanostructures: The ApoA1 PA co-assembly retained the alpha-helical secondary structure of the targeting sequence alone (4F peptide), evidenced by the negative ellipticity peaks near 208 and 222 nm (FIG. 20A). The ApoA1 PA also showed β-sheet character with a shifted positive ellipticity peak, an effect likely caused by co-assembly with the diluent PA, which showed strong β-sheet character, demonstrated by the presence of a broad negative peak near 218 nm. In contrast, the secondary structure of PA nanofibers co-assembled with a scrambled targeting sequence (Scr PA) closely resembled the β-sheet structure of the diluent PA. Incorporating LXR into either the ApoA1 PA co-assembly (ApoA1-LXR PA) or the 4F peptide (4F-LXR) dampened the alpha-helical structure, as shown in FIG. 20B and FIG. 21. Similar patterns of secondary structure were observed at physiological temperature (37° C.).

Figure 23A:
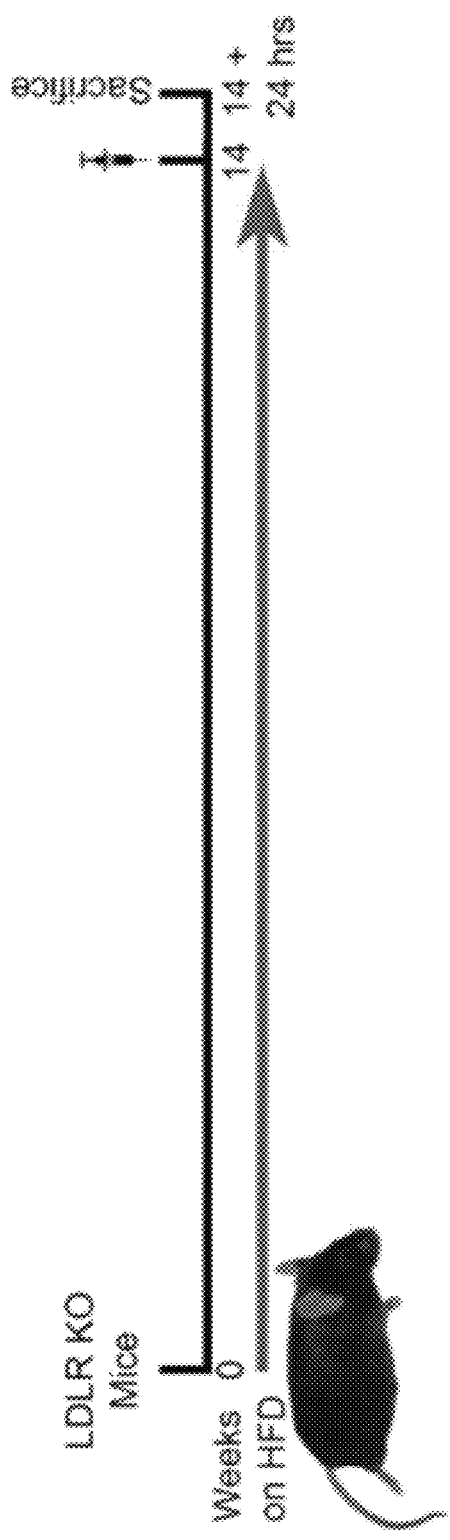
FIG. 23A-B. Nanofiber-mounted ApoA1 peptide is superior to naked 4F peptide for targeting atherosclerosis and drug delivery.
Figure 23B:
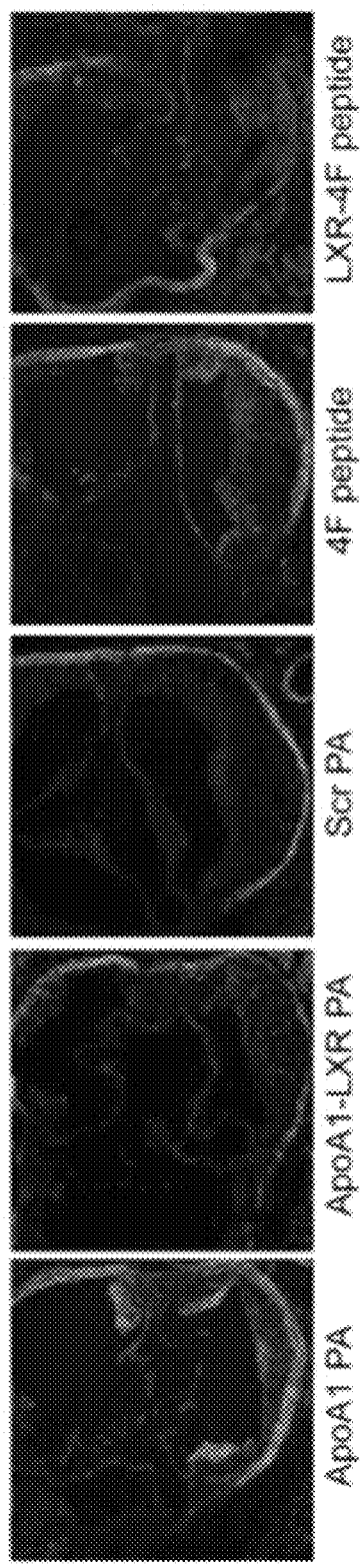
Figure 24A:
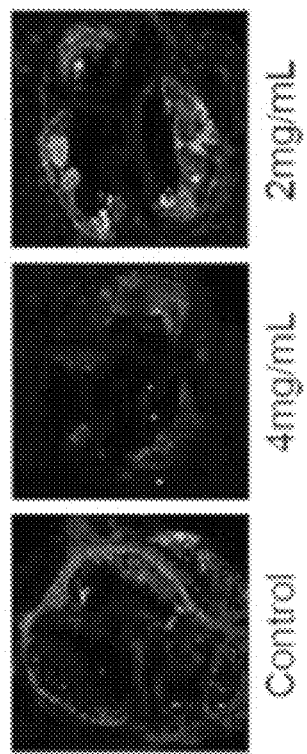
FIG. 24A-24F. Determination of optimum dose and concentration of ApoA1 PA for targeting atherosclerosis through IV injection. Groups labeled as control are age matched and high-fat diet non-injected mice.
Figure 24B:
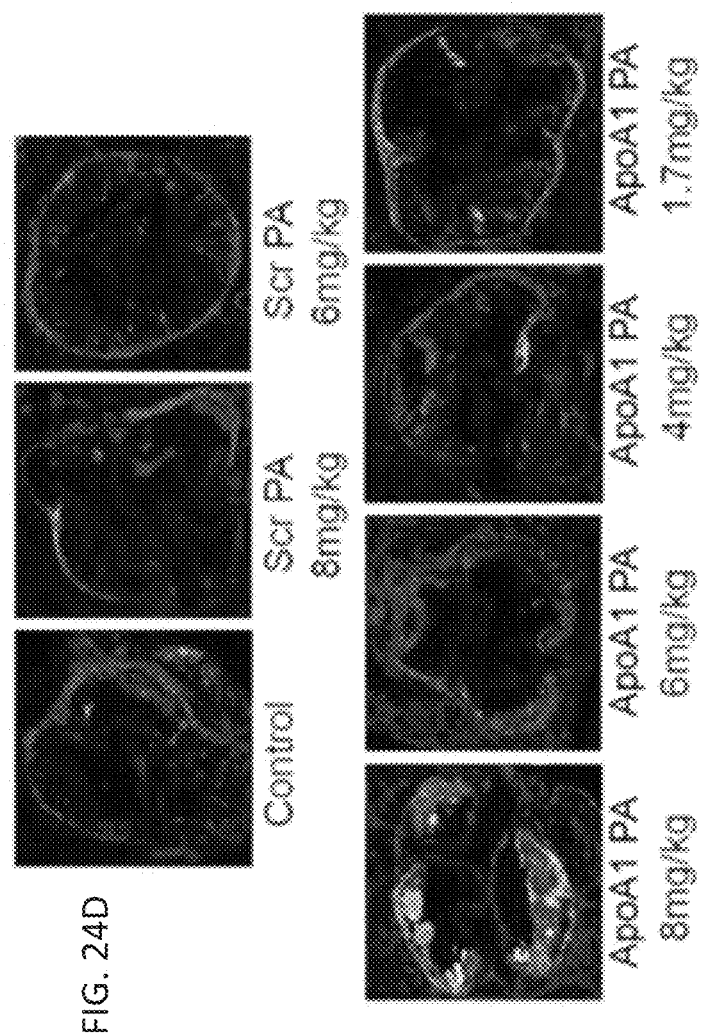

Dynamic light scattering was used as an indicator of nanofiber formation, as higher β-sheet content is correlated with increased light scattering. PA nanofiber formation was Targeting and drug delivery efficacy of ApoA1 PA nanofibers: Targeted ApoA1 PA, ApoA1-LXR PA, and the targeting sequence alone (4F peptide) localized to areas of atherosclerosis within 24 hours after injection as indicated by red fluorescence from the conjugated Alexa Fluor® 546 dye (FIG. 23B). Scrambled PA and the targeting peptide sequence covalently bonded to the LXR agonist without the PA platform (4F-LXR) did not localize to areas of atherosclerosis. The optimum concentration of targeted ApoA1 PA nanofiber was determined at a constant dose of 8 mg/kg. When fluorescent pixels were quantified in the aortic roots of mice given concentrations of 4 mg/mL vs. 2 mg/mL at 24 hours after injection, there was no significant difference (FIG. 24A-24B). These concentrations were chosen because a concentration of 1 mg/mL required a prohibitively high volume of injection, and greater than 4 mg/mL yielded volumes too low for accurate injection with a 0.3 mL syringe. There was no significant difference between concentrations; thus, a 2 mg/mL concentration was used for all subsequent studies.

Figure 24C:
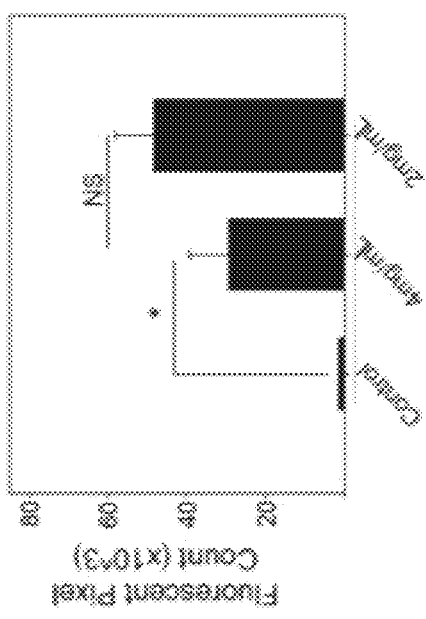
Figure 24D:
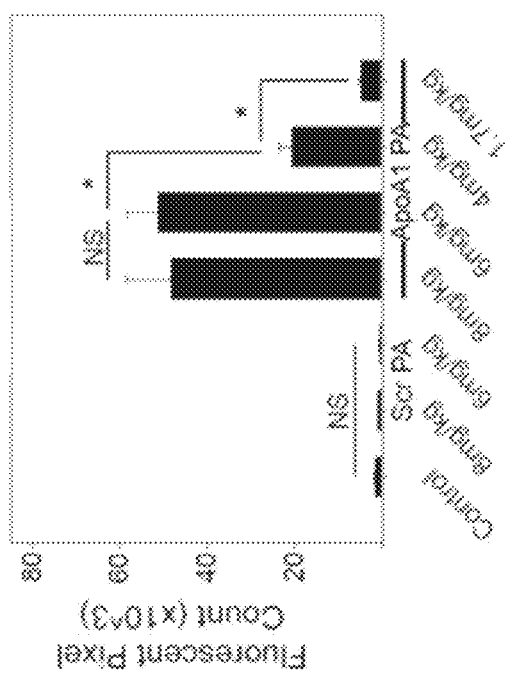
Figure 24F:
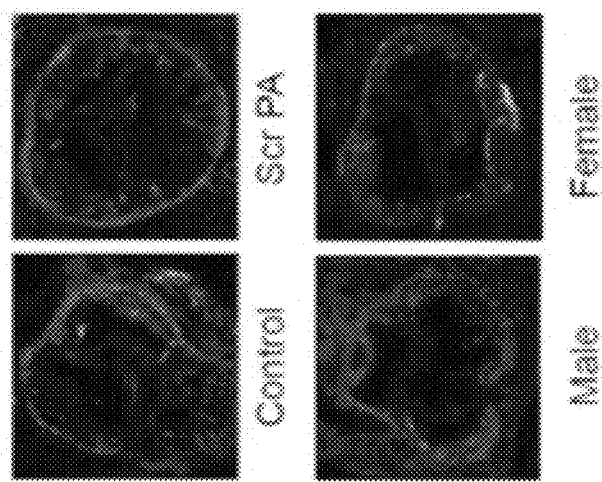
Figure 24E:
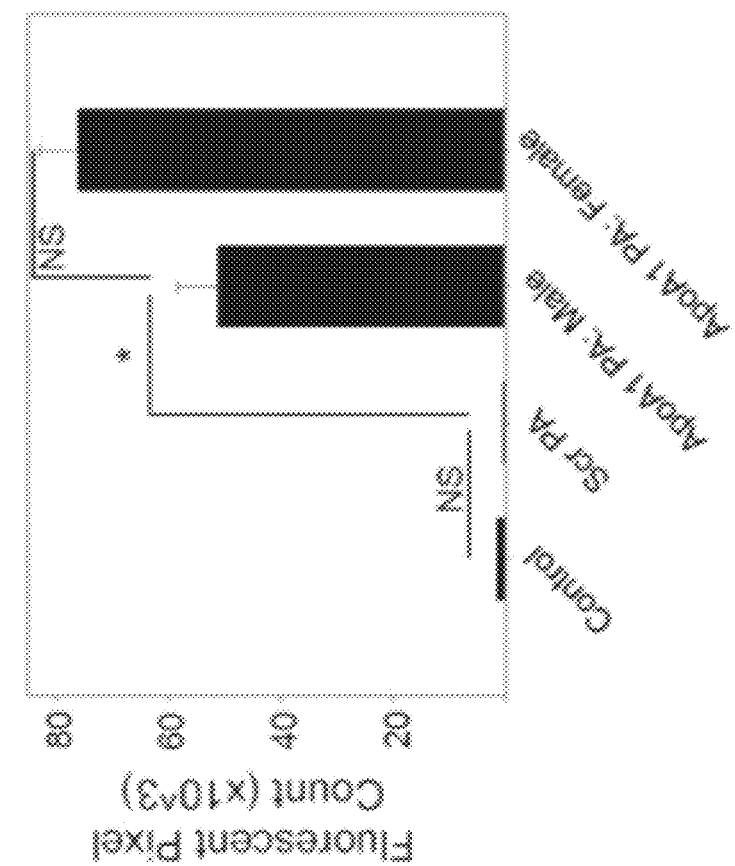

The optimal dose of ApoA1 PA was determined at a constant concentration of 2 mg/mL. Doses of 8 mg/kg and 6 mg/kg were superior to 4 mg/kg, which was superior to 1.7 mg/kg (FIG. 24C-24D). Compared to non-injected and scrambled PA controls, a dose of 8 mg/kg and 6 mg/kg yielded nearly identical localization at areas of atherosclerosis as measured by fluorescent pixel quantification at the aortic root. Therefore, 6 mg/kg dosing was used for all subsequent studies. Finally, localization of the targeted ApoA1 PA in male versus female LDLR KO mice was evaluated, and no statistically significant difference in localization between the sexes was found (FIG. 24E-24F).

Regarding binding duration, targeted ApoA1 PA localized to areas of atherosclerosis within the first 24 hours after injection. ApoA1 PA nanofibers remained localized to areas of atherosclerosis at high concentrations for two days. By 3-7 days after injection, ApoA1 PA nanofibers diminished in concentration within areas of atherosclerosis. After 10-14 days post injection with ApoA1 PA, fluorescent pixel analysis was not different from control non-injected mice (FIG. 25A-25B).

Figure 26E:
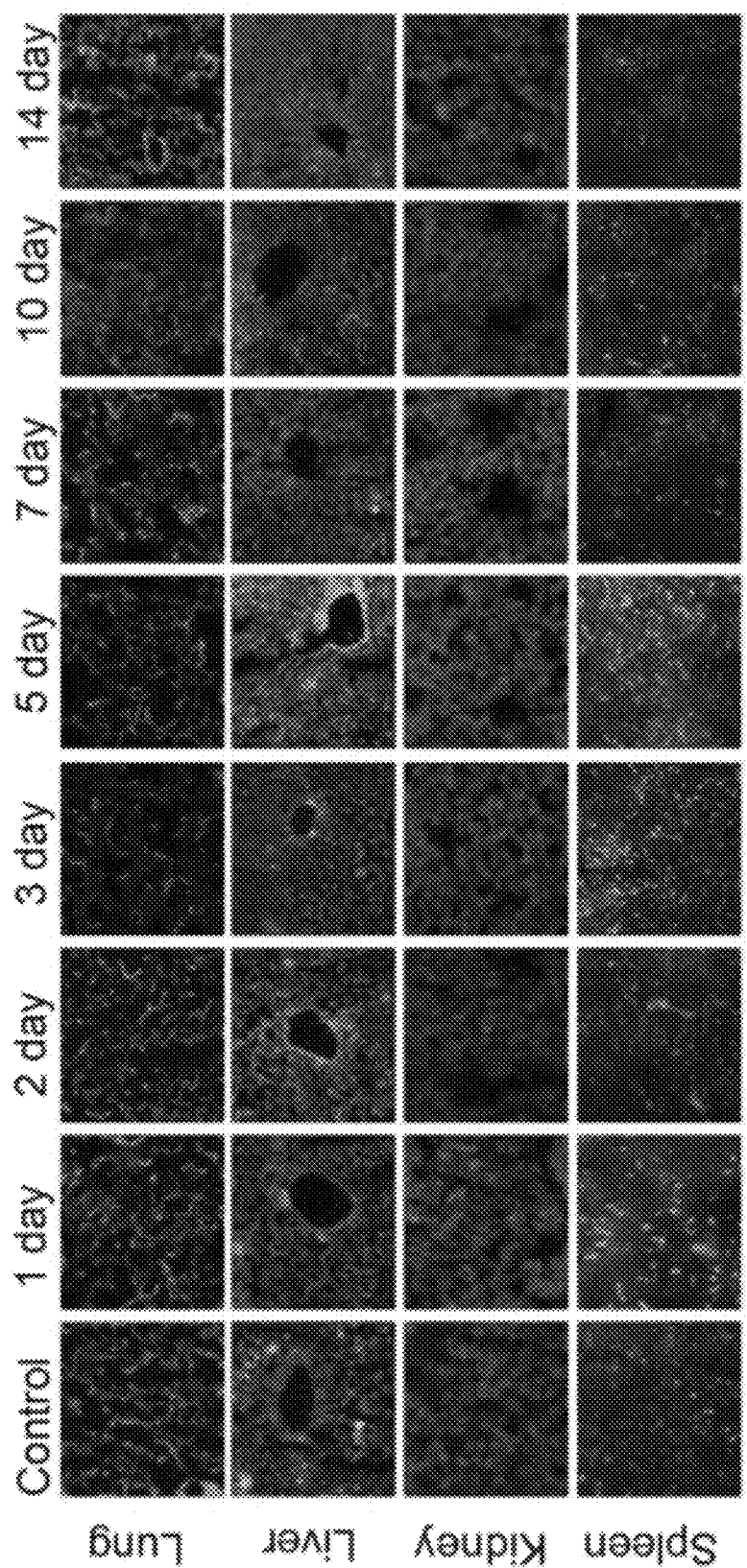

In order to identify off-target localization of ApoA1 PA nanofibers, fluorescent pixel analysis was performed in internal organs (lung, liver, kidney, spleen) from 1-14 days post injection. There was minimal detection of ApoA1 PA in the lung, liver, and kidney. ApoA1 PA was detected in the spleen between 1-10 days post injection, with maximum concentrations between 3-7 days (FIG. 26A-D). Representative images of internal organs, especially splenic sections with high concentrations of red pixels, appear yellow due to high background levels of green autofluorescence (FIG. 26E). However, in all internal organs, red fluorescent pixels returned to non-injected control levels by 10-14 days post injection.

Figure 27D:
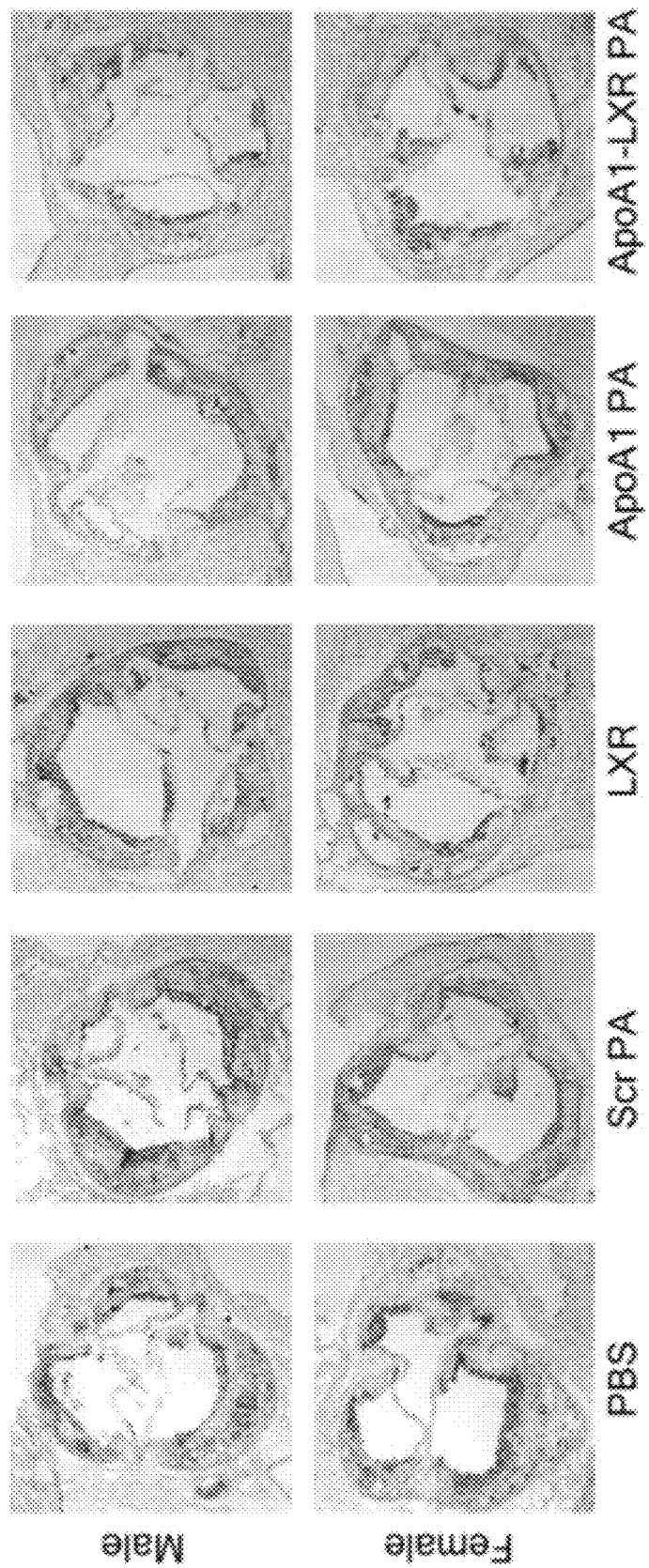

Treatment of atherosclerosis: To investigate the therapeutic potential of PAs in reducing plaque burden, intravenous injection of PAs in male and female LDLR KO mice that had developed atherosclerosis after 14 weeks on a high fat diet was examined. The mice were treated with ApoA1-LXR PA, ApoA1 PA, LXR, scrambled PA, or saline twice per week over eight weeks with the effects of each condition evaluated by the percent of atherosclerosis in the aortic root (FIG. 27A). For both sexes, atherosclerosis progression was significantly decreased in comparison to the PBS control after treatment with LXR (p<0.0001), ApoA1 PA (p=0.012), scrambled PA (p=0.034), or ApoA1-LXR PA (p=0.0001) (FIG. 27B). The ability of each treatment to reduce atherosclerotic plaque size was variable based on sex (FIG. 27C-27D). For example, ApoA1-LXR PAs significantly enhanced plaque reduction in comparison to scrambled PA treatments in males (p=0.0165), an observation not seen in females. Additionally, scrambled PAs showed greater effects upon reducing atherosclerosis in females in comparison to males (p=0.0487). Treatments with LXR showed similar therapeutic effects as ApoA1-LXR PA treatments in both males (p=0.3978) and females (p=0.2258). Surprisingly, treatment with ApoA1-LXR PA showed no significant improvement on plaque reduction in females versus ApoA1 PAs (p=0.6928). In contrast, while not significant, a trend was observed in males for ApoA1-LXR PA treatment having greater effects on plaque reduction in comparison to ApoA1 PA treatments (p=0.0687). LXR and ApoA1-LXR treatments reversed atherosclerosis from baseline levels in both sexes by approximately 5%. No additional reduction in plaque content within the aortic root was observed in ApoA1-LXR treatments in comparison to LXR alone. This finding is in contrast to the in vitro cholesterol efflux results, where significantly higher macrophage cholesterol efflux in ApoA1-LXR treatments in comparison to LXR, ApoA1 PA, and scrambled PAs was observed. Possible reasons for the therapeutic effect with ApoA1 PAs could be from the cholesterol efflux potential of the 4F peptide. The PAs may also reduce availability of macrophages to migrate to the plaque due to uptake and clearance of the PA nanofibers, which is consistent with the scrambled PAs that are able to reduce plaque progression without directly targeting the plaque site.

While LXR and scrambled PA treatments reduce plaque burden, they also increased liver toxicity in male mice based on significantly elevated levels of aspartate aminotransferase (AST) in the blood in comparison to the PBS conditions (p=0.0207 and p=0.0018, respectively; Table 2). Neither ApoA1-LXR PAs nor ApoA1 PAs increased AST levels in male mice in comparison to the PBS control (p=0.3117 and p=0.1348, respectively). Interestingly, female mice showed no significant differences in AST levels in comparison to the PBS control for the LXR (p=0.2002), scrambled PA (p=0.1636), or ApoA1-LXR PA (p=0.5832) treatments. No significant differences in blood levels of cholesterol, alanine aminotransferase, or alkaline phosphatase were observed between treatments or sex.

TABLE 2

Treatment study serum chemistry data. Data are shown as group medians with ranges in parentheses.

| Test/Tx | PBS | LXR | ApoA1 PA | Scr PA | ApoA1-LXR PA |
|---|---|---|---|---|---|
| All | N = 9 | N = 10 | N = 9 | N = 10 | N = 9 |
| Females | N = 5 | N = 5 | N = 4 | N = 5 | N = 5 |
| Males | N = 4 | N = 5 | N = 5 | N = 5 | N = 4 |
| Cholesterol (mg/dL) | 1755 (288-2932) | 2000.5 (803-3554) | 1619 (1128-2237) | 2003.5 (170-3091) | 1877 (829-2533) |
| | 611 (489-2932) | 2029 (803-2396) | 2020 (1768-2237) | 1980 (695-2636) | 2323 (1836-2533) |
| | 2233 (288-2535) | 1972 (1106-3554) | 1455 (1128-1619) | 2027 (170-3091) | 1600.5 (829-2360) |
| Aspartate Aminotransferase (AST, U/L) | 82 (8-290)*# | 135 (78-214) | 95 (52-216) | 154.5 (65-629) | 74 (32-145)*# |
| | 89 (8-290) | 142 (91-166) | 182.5 (138-216) | 153 (65-157) | 74 (32-145) |
| | 54.5 (27-82) | 102 (78-214) | 90 (52-95) | 199 (79-629) | 74.5 (46-109) |
| Alanine Aminotransferase (ALT, U/L) | 28 (4-81) | 40 (18-136) | 39 (6-88) | 35 (16-277) | 44 (18-122) |
| | 28 (22-81) | 33 (18-45) | 19 (6-88) | 22 (16-127) | 44 (25-85) |
| | 19.5 (4-49) | 47 (24-136) | 70 (28-87) | 205 (34-277) | 46 (18-122) |
| Alkaline phosphatase (U/L) | 50 (24-98) | 65.5 (8-78) | 46 (33-80) | 55.5 (26-97) | 58 (40-83) |
| | 33 (24-98) | 73 (8-78) | 68 (54-80) | 57 (45-77) | 66 (55-75) |
| | 53 (36-57) | 41 (40-77) | 40 (33-46) | 45 (26-97) | 56.5 (40-83) |
| Total Bilirubin (mg/dL) | 0.3 (0.1-0.5) | 0.4 (0.2-0.9) | 0.3 (0.2-0.5) | 0.3 (0.1-0.5) | 0.4 (0.1-0.7) |
| | 0.2 (0.1-0.3)* | 0.6 (0.5-0.9)$ | 0.45 (0.2-0.5) | 0.3 (0.1-0.5) | 0.4 (0.1-0.7) |
| | 0.4 (0.3-0.5) | 0.3 (0.2-0.3) | 0.2 (0.2-0.4) | 0.2 (0.2-0.3) | 0.35 (0.3-0.5) |
| Bilirubin - Conjugated (mg/dL) | 0 (0-0.1) | 0.05 (0-0.3) | 0.1 (0-0.2) | 0.1 (0-0.2) | 0.1 (0-0.3) |
| | 0 (0-0.1) | 0 (0-0.3) | 0.1 (0.1-0.2) | 0 (0-0.2) | 0.1 (0-0.3) |
| | 0 (0-0.1) | 0.1 (0-0.1) | 0 (0-0.1) | 0.1 (0-0.2) | 0.05 (0-0.1) |
| Bilirubin - Unconjugated (mg/dL) | 0.2 (0.1-0.5) | 0.3 (0.1-0.8) | 0.2 (0.1-0.4) | 0.15 (0-0.5) | 0.4 (0-0.5) |
| | 0.2 (0.1-0.2)* | 0.5 (0.3-0.8)$ | 0.3 (0.1-0.4) | 0.3 (0.1-0.5) | 0.4 (0-0.5) |
| | 0.4 (0.2-0.5) | 0.2 (0.1-0.3) | 0.2 (0.2-0.4) | 0.1 (0-0.3) | 0.35 (0.2-0.4) |
| Creatine Kinase (U/L) | 126 (80-351) | 137.5 (102-198) | 177 (84-575) | 144.5 (67-356) | 150 (32-250) |
| | 126 (101-351) | 136 (126-198) | 309.5 (167-575) | 146 (95-356) | 140 (32-165) |
| | 129.5 (80-166) | 138 (102-150) | 131 (84-182) | 143 (67-322) | 158.5 (103-250) |

TABLE 2-continued

Treatment study serum chemistry data. Data are shown as group medians with ranges in parentheses.

| Test/Tx | PBS | LXR | ApoA1 PA | Scr PA | ApoA1-LXR PA |
|---|---|---|---|---|---|
| All | N = 9 | N = 10 | N = 9 | N = 10 | N = 9 |
| Females | N = 5 | N = 5 | N = 4 | N = 5 | N = 5 |
| Males | N = 4 | N = 5 | N = 5 | N = 5 | N = 4 |
| Total Protein (g/dL) | 5.2 (4.3-5.6)^ | 5.45 (5.1-5.7) | 5.6 (5.1-6)* | 5.4 (2.5-5.7) | 5.4 (5.1-5.8) |
| | 4.5 (4.3-5.6) | 5.4 (5.1-5.7) | 5.45 (5.1-5.6) | 5.4 (4.7-5.7) | 5.4 (5.4-5.8) |
| | 5.45 (5.1-5.6) | 5.5 (5.3-5.7) | 5.8 (5.6-6) | 5.4 (2.5-5.7) | 5.55 (5.3-5.7) |
| Globulin (g/dL) | 2.5 (2.3-2.9) | 2.7 (2.1-3) | 3.2 (2.1-3.4)* | 2.35 (1.3-2.8) | 2.6 (2.1-2.8) |
| | 2.4 (2.3-2.5) | 2.3 (2.1-2.9) | 2.45 (2.1-2.8)& | 2.3 (2.2-2.5) | 2.4 (2.1-2.7) |
| | 2.65 (2.5-2.9) | 2.8 (2.7-3) | 3.3 (3.2-3.4) | 2.6 (1.3-2.8) | 2.65 (2.6-2.8) |
| Sodium (mmol/L) | 141 (134-156) | 139.5 (131-146) | 141.5 (137-145) | 138 (134-155) | 144 (136-147) |
| | 154 (134-156) | 140 (138-146) | 137 (137-140) | 138 (135-155) | 144 (136-147) |
| | 140 (137-148) | 139 (131-142) | 143 (141-145) | 138 (134-149) | 141 (138-146) |
| Potassium (mmol/L) | 4.4 (3.6-4.9)*% | 5.2 (3.8-9.6) | 4.75 (4.2-5.7) | 5.15 (4.4-5.6) | 5.1 (4.7-6.2) |
| | 4.3 (3.6-4.9) | 4.6 (3.8-9.6) | 4.8 (4.6-5.4) | 4.8 (4.7-5.3) | 5 (4.7-6.2) |
| | 4.75 (4.2-4.9) | 5.2 (5.2-6.1) | 4.7 (4.2-5.7) | 5.2 (4.4-5.6) | 5.2 (4.8-5.8) |
| Chloride (mmol/L) | 107 (97-118) | 103 (99-109) | 105 (102-106) | 100.5 (97-119) | 104 (100-109) |
| | 114 (97-118) | 102 (101-109) | 102 (102-105) | 100 (99-117) | 107 (102-109) |
| | 105 (103-112) | 104 (99-107) | 105 (103-106) | 101 (97-119) | 102 (100-105) |
| Bicarbonate and $CO_2$ (mmol/L) | 12 (8-14)^ | 12 (9-16) | 12 (11-15) | 13 (10-16) | 11 (9-15) |
| | 10 (8-13) | 10 (9-12) | 11.5 (11-12) | 14 (10-16) | 11 (9-15) |
| | 12 (11-14) | 14 (12-16) | 13 (11-15) | 13 (11-16) | 11.5 (10-13) |
| Blood Urea Nitrogen (mg/dL) | 23 (17-34) | 23 (18-32) | 19 (13-22) | 22 (14-31) | 24 (13-30) |
| | 22 (17-34) | 21.5 (18-24) | 21.5 (20-22) | 18.5 (14-26) | 19.5 (13-30) |
| | 26 (19-29) | 24 (20-32) | 16 (13-19) | 24 (18-31) | 24.5 (24-26) |
| Creatine (U/L) | 0 (0-0.1) | 0 (0-0.2) | 0 (0-0.1) | 0 (0-0.1) | 0 (0-0.2) |
| | 0 (0-0.1) | 0 (0-0.2) | 0 (0-0.1) | 0 (0-0.1) | 0 (0-0.2) |
| | 0 (0-0) | 0 (0-0) | 0 (0-0.1) | 0 (0-0.1) | 0 (0-0.1) |
| Glucose (mg/dL) | 226 (136-279) | 237 (134-332) | 196 (154-271) | 200.5 (29-424) | 210 (95-410) |
| | 226 (136-277) | 203 (134-226) | 204 (160-271) | 198 (184-333) | 210 (190-241) |
| | 202.5 (160-279) | 259 (248-332) | 196 (154-242) | 203 (29-424) | 228.5 (95-410) |

Black text: all, red text: female, blue text: male.
*p < 0.05 vs. LXR
p < 0.05 vs. Scr PA
^p < 0.05 vs. ApoA1 PA
%p < 0.05 vs. ApoA1-LXR PA
$p < 0.05 female LXR vs. male LXR
&p < 0.05 female ApoA1 PA vs male ApoA1 PA.
n = 21 male and 24 female blood samples analyzed per condition.

Discussion:

It was found that long-aspect ratio PAs containing an apolipoprotein A1-mimetic peptide, 4F, serve as effective nanocarriers to target LXR agonists to atherosclerotic plaque in vivo. Using an amphiphile control of the 4F peptide directly conjugated to the hydrophobic LXR drug, we found a lack of nanofiber formation. These results are in agreement with the importance of R-sheet forming peptides in PA nanofiber formation and subsequent targeting to diseased vasculature shown in the previous Examples. The present disclosure demonstrates that ApoA1 PA nanofibers with an incorporated LXR agonist can be used for safe, targeted delivery to areas of atherosclerotic plaque to reverse atherosclerosis in a preclinical in vivo model.

Example 4

LXR-Tethered PAs

Figure 28:
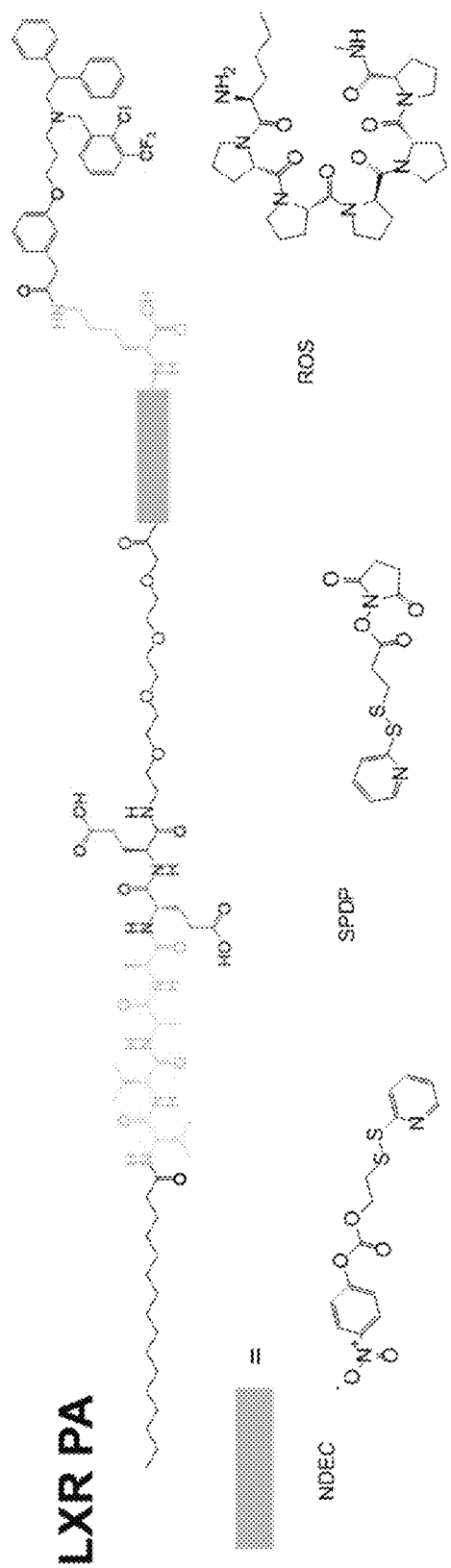
FIG. 28 shows exemplary structures for therapeutic PAs containing the LXR agonist GW3965 as the therapeutic agent (e.g. LXR PAs). The LXR agonist is tethered to the PA backbone through a lysine amino acid that is covalently bound to either an NDEC, SPDP, or proline linker.

Methods. Two linkages for tethering LXR agonists (e.g. GW3965) to the PA backbone were investigated. reactive oxygen species (ROS)-cleavable prolines and glutathione-cleavable succinimidyl 3-(2-pyridyldithio) propionate (SPDP). GW3965 was tethered to PAs using solid phase peptide synthesis and the PAs were characterized for GW3965 release. PAs containing GW3965 tethered to the PA backbone are referred to in this example as LXR-PAs. Exemplary structures of LXR PAs are shown in FIG. 28. To allow targeted delivery to atherosclerotic lesions, the niche-responsive LXR-PAs were coassembled with PAs containing apolipoprotein A1-derived peptide 4F (ApoA1-PAs), and the processing parameters that enabled nanofiber formation were determined. Lastly, the effect of nanofibers on macrophage viability and cholesterol efflux in vitro were examined.

Figure 30A:
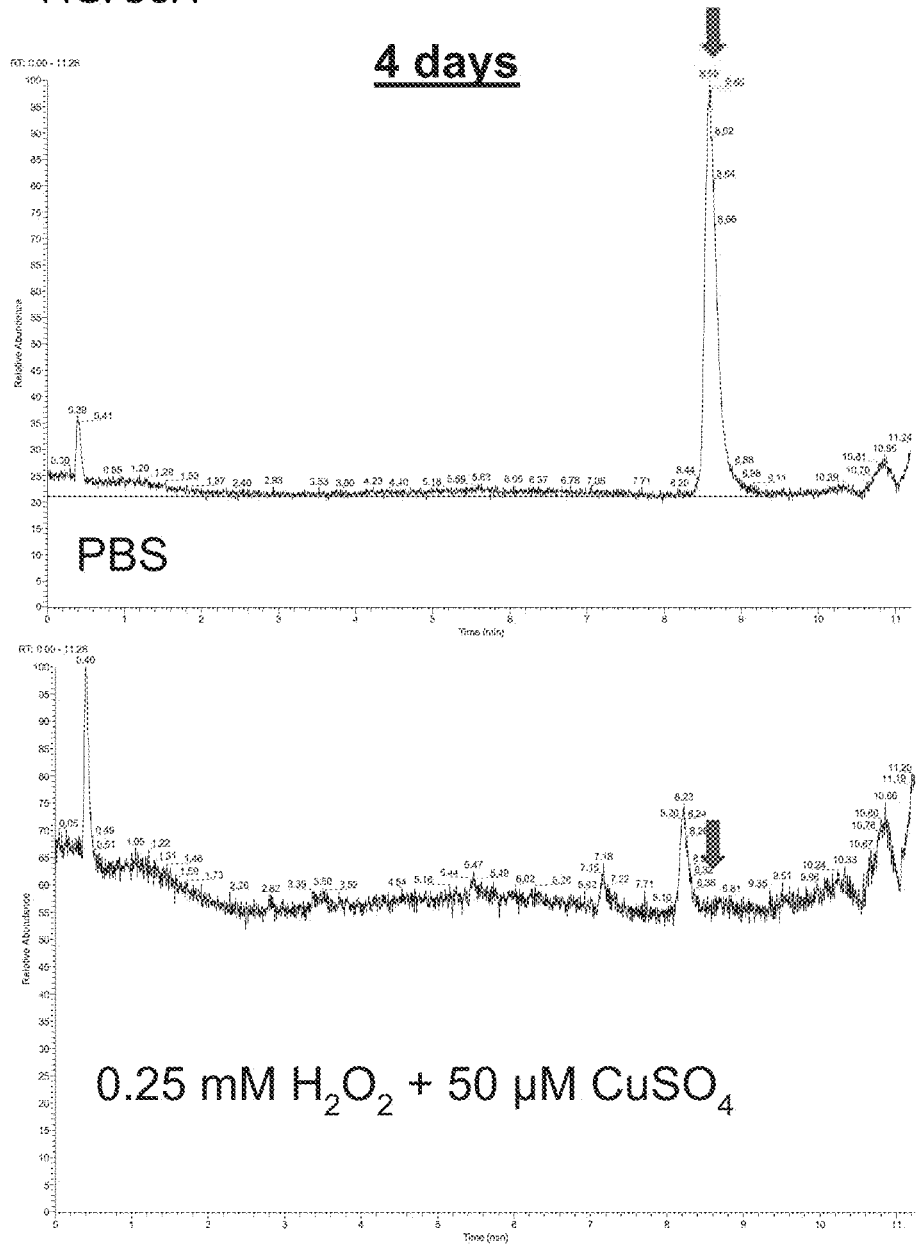
Figure 30B:
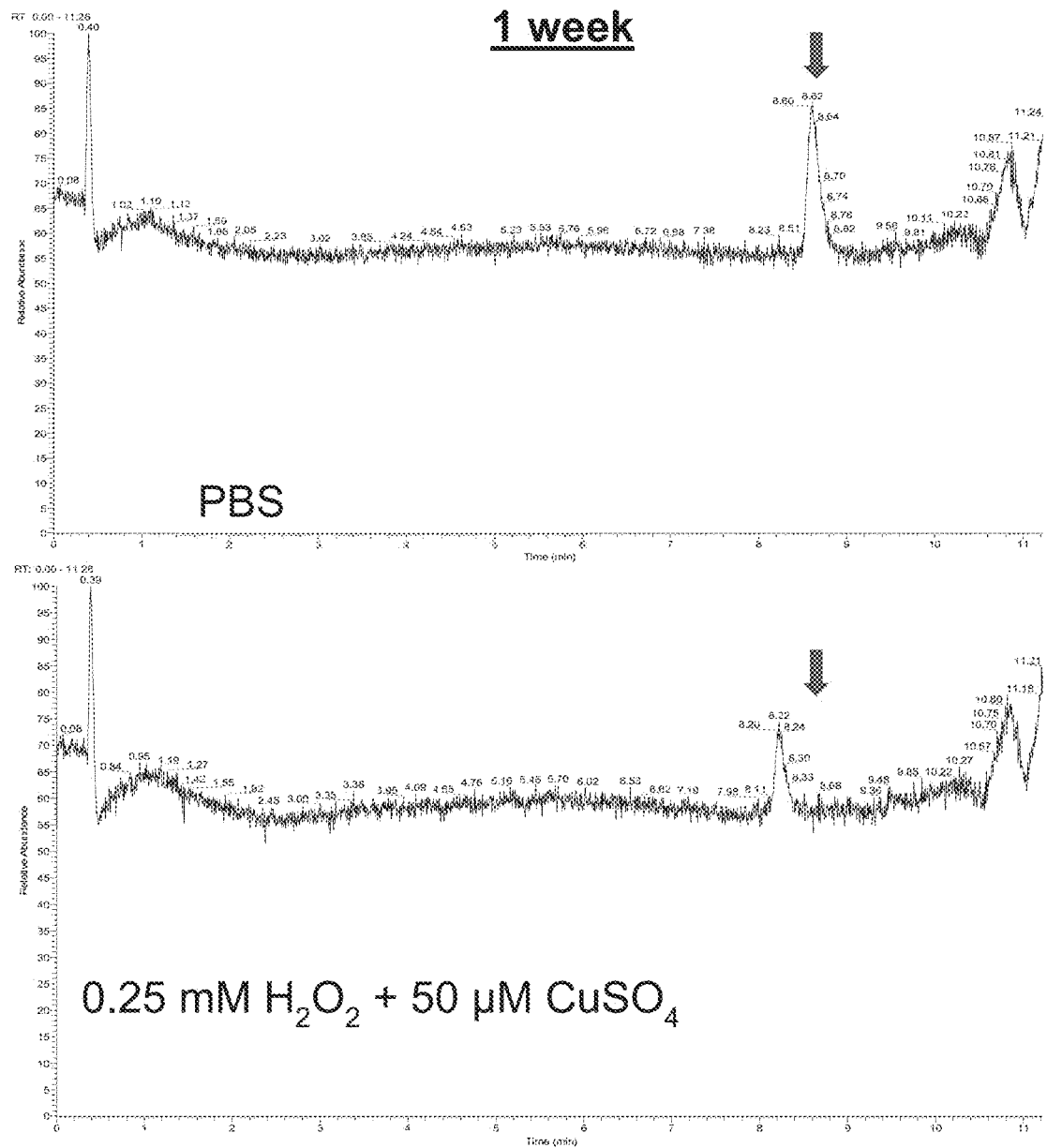
Figure 31A:
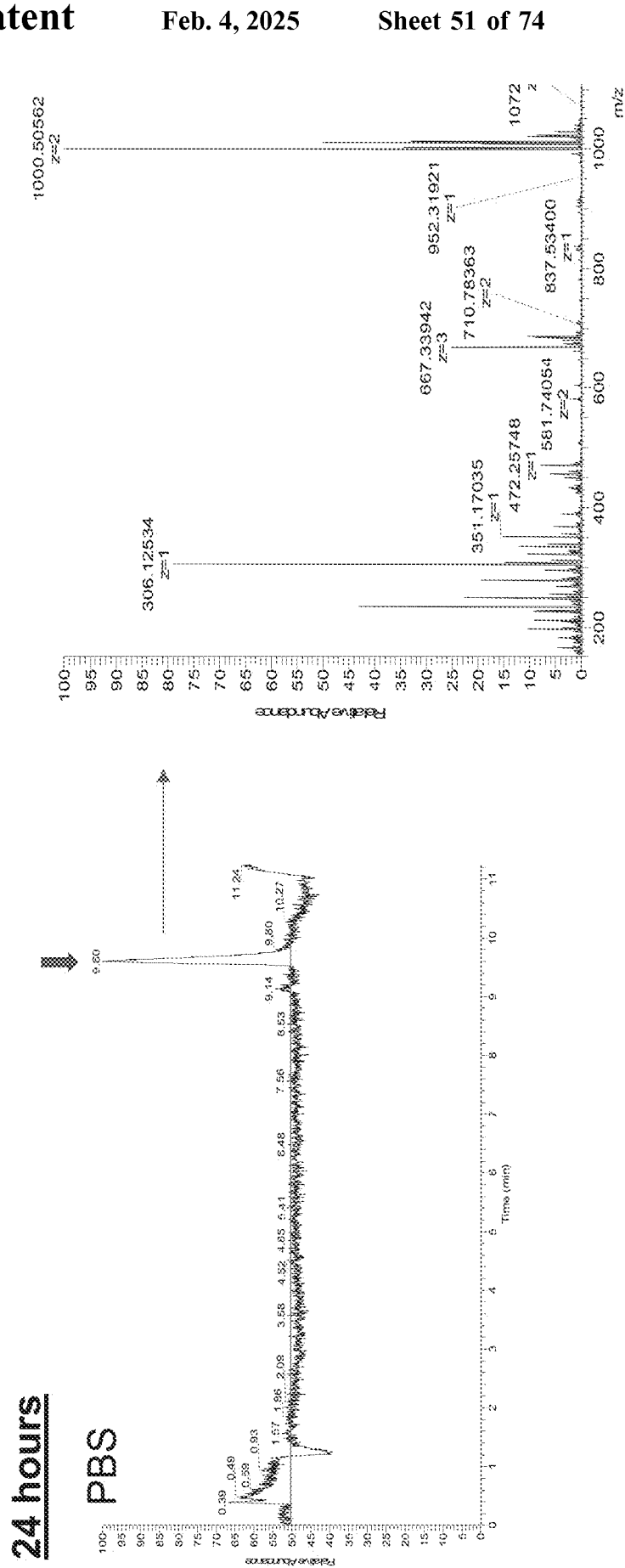
FIG. 31A-31C shows cleavage after treatment with PBS (FIG. 31A) or GSH (FIG. 31B, FIG. 31C) for SPDP-LXR PAs. Results after 24 hours are shown. Complete cleavage of the SPDP-LXR PA occurs by 24 hours of treatment with 10 mM of GSH, the expected intracellular concentration. Much less PA cleavage is seen at 0.1 mM GSH, the expected plasma concentration.
Figure 31B:
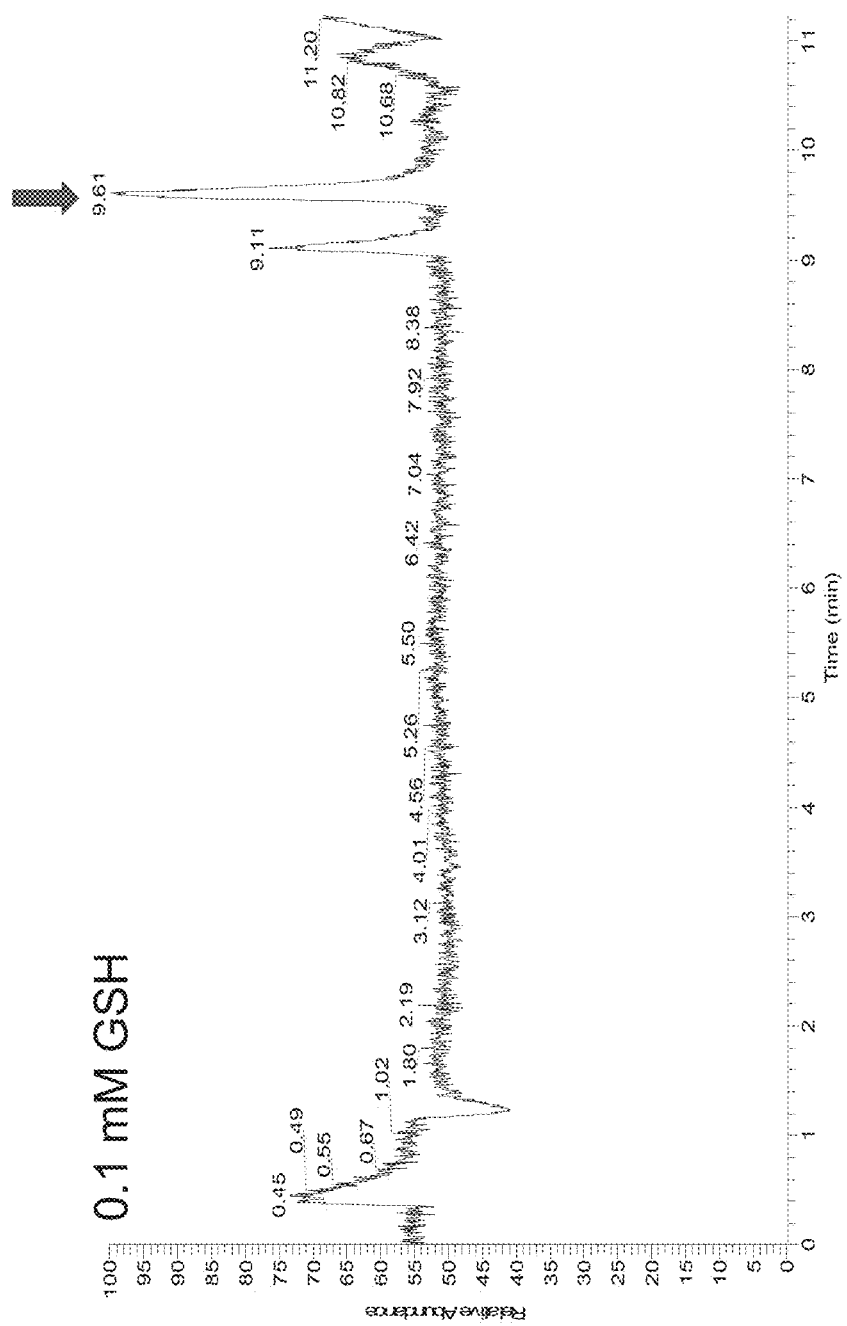
Figure 31C:
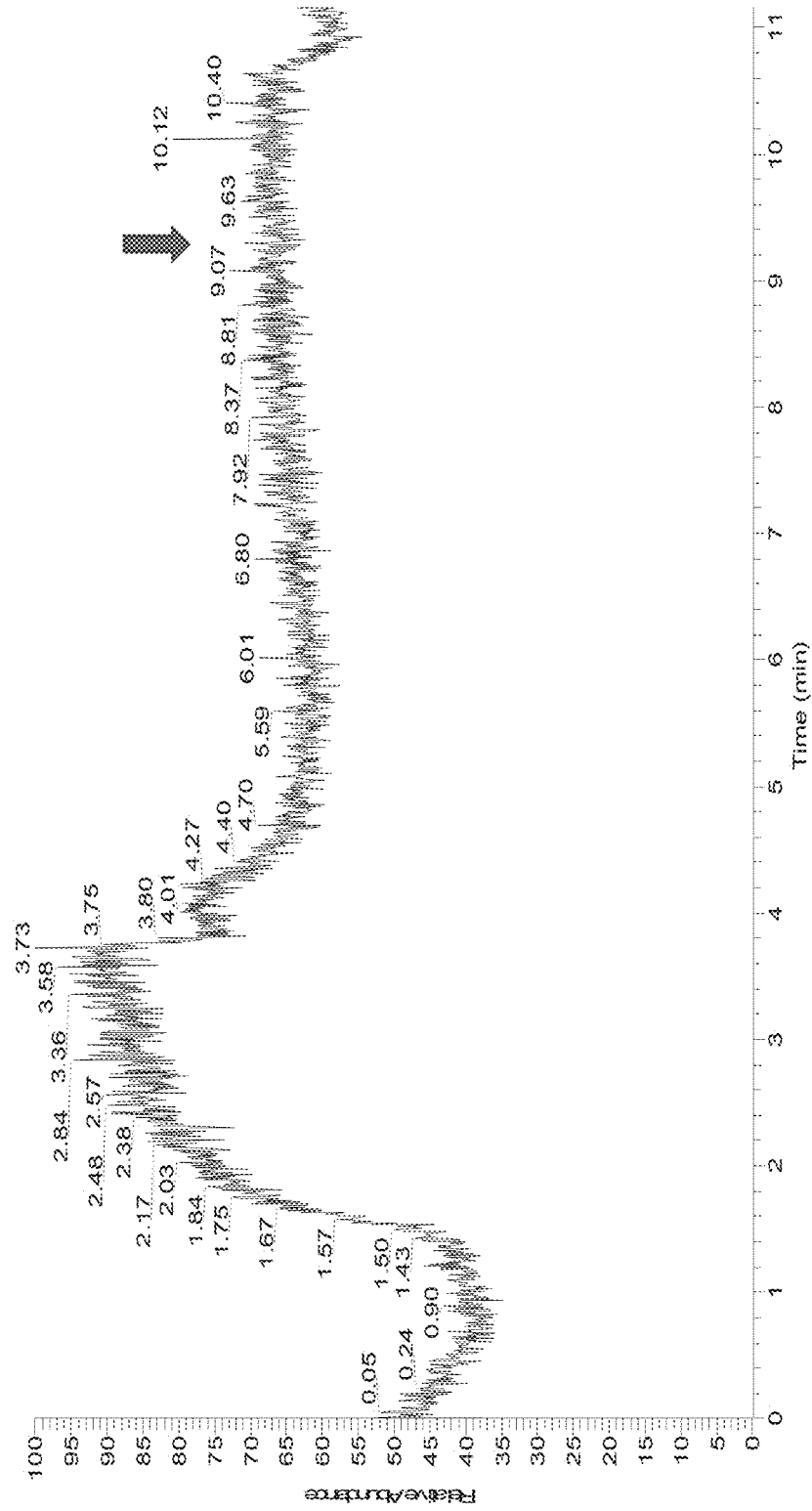
Figure 32A:
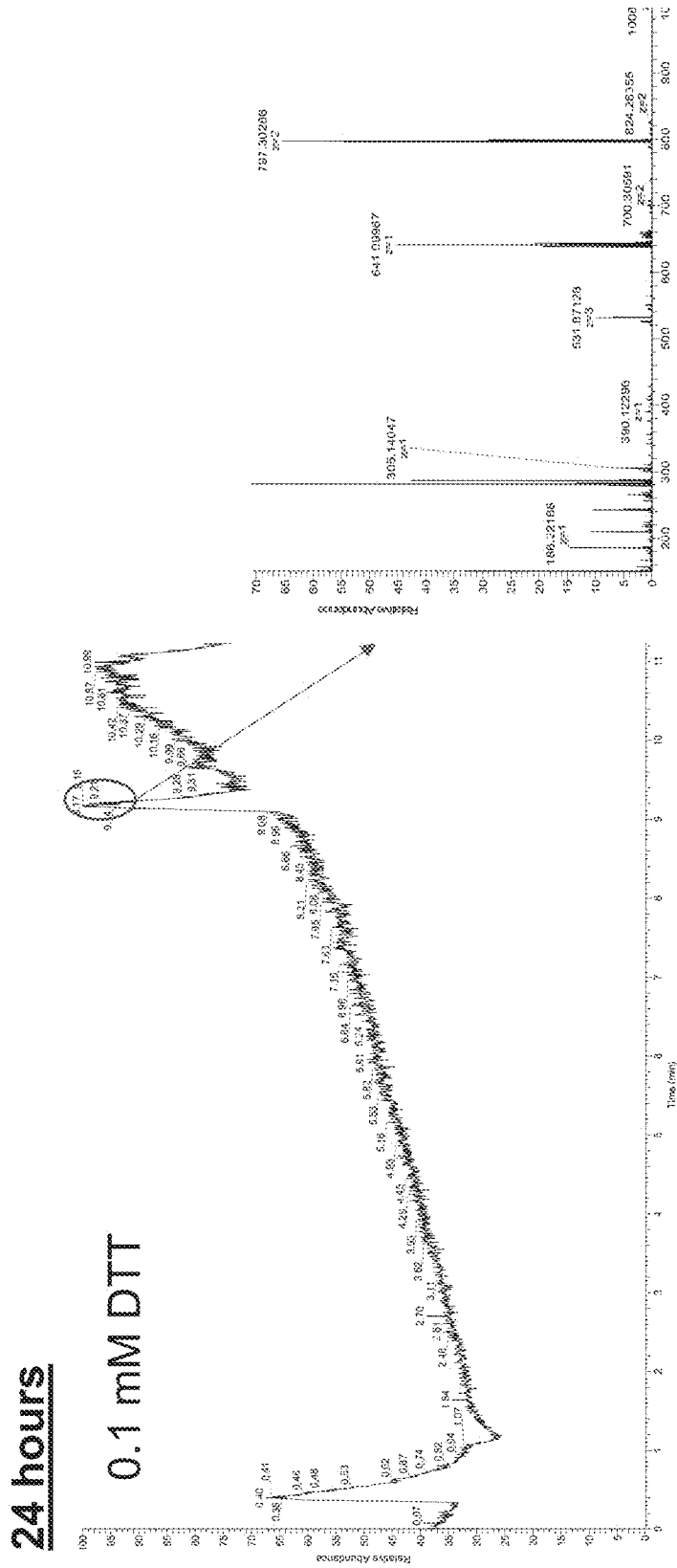
FIG. 32A-32B shows results for SPDP-LXR PAs after treatment with 0.1 mM DTT (FIG. 32A) or 10 mM DTT (FIG. 32B). Results after 24 hours are shown. The DTT allows more specific analysis disulfide reduction than GSH. In these images, the expected molecular weight of the cleavage product of 797.3 g/mol is shown from 10 mM DTT treatment.
Figure 32B:
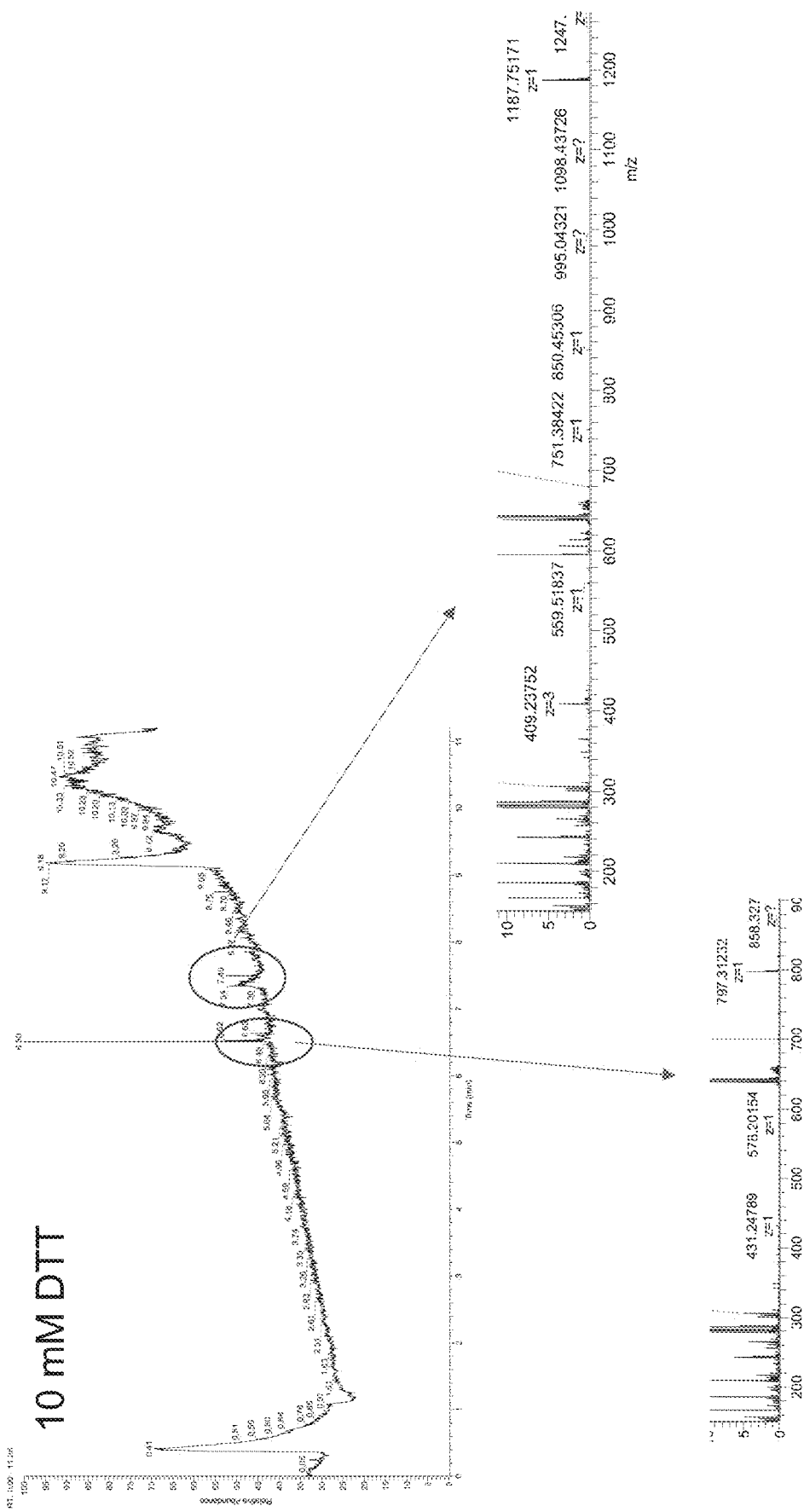
Figure 33C:
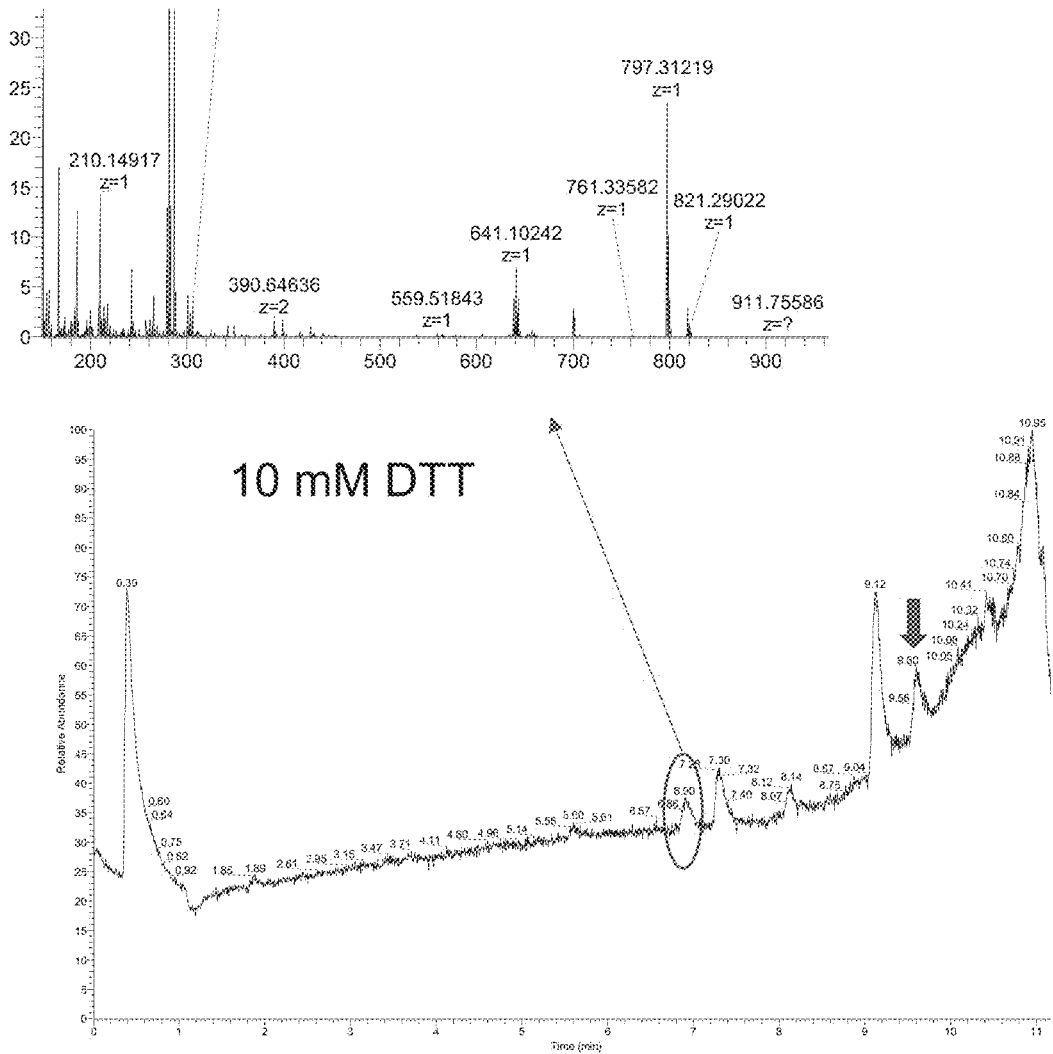

Results:

Cleavage assays: Cleavage after treatment with $H_2O_2$+ $CuSO_4$ was investigated for ROS-LXR PAs (e.g. peptide amphiphiles containing the LXR agonist GW3965 attached to the ROS-sensitive linker $KP_5K$ (SEQ ID NO: 10)) and SPDP-LXR PAs (e.g. peptide amphiphiles containing the LXR agonist GW3965 attached to the GSH-sensitive linker SPDP). Results for ROS-LXR PAs after 24 hours are shown in FIG. 29A-29B, results after 4 days and 1 week are shown in FIG. 30A and FIG. 30B, respectively. Results for SPDP-LXR PAs are shown in FIG. 31A-31C. Results after 24 hours are shown. Results for SPDP-LXR PAs after DTT treatment are shown in FIG. 32A-32B (24 hours) and FIG. 33A-33C (1 week). 46% cleavage of ROS-LXR PAs was observed after 24 hours of treatment with 250 μM $H_2O_2$+ $CuSO_4$, and 100% cleavage was observed by 4 days. In comparison, the SPDP-LXR PAs showed 100% cleavage in response to 24 hours of treatment with 10 mM glutathione.

Conditions for nanofiber formation: Conditions for nanofiber formation were investigated.

Figure 34A:
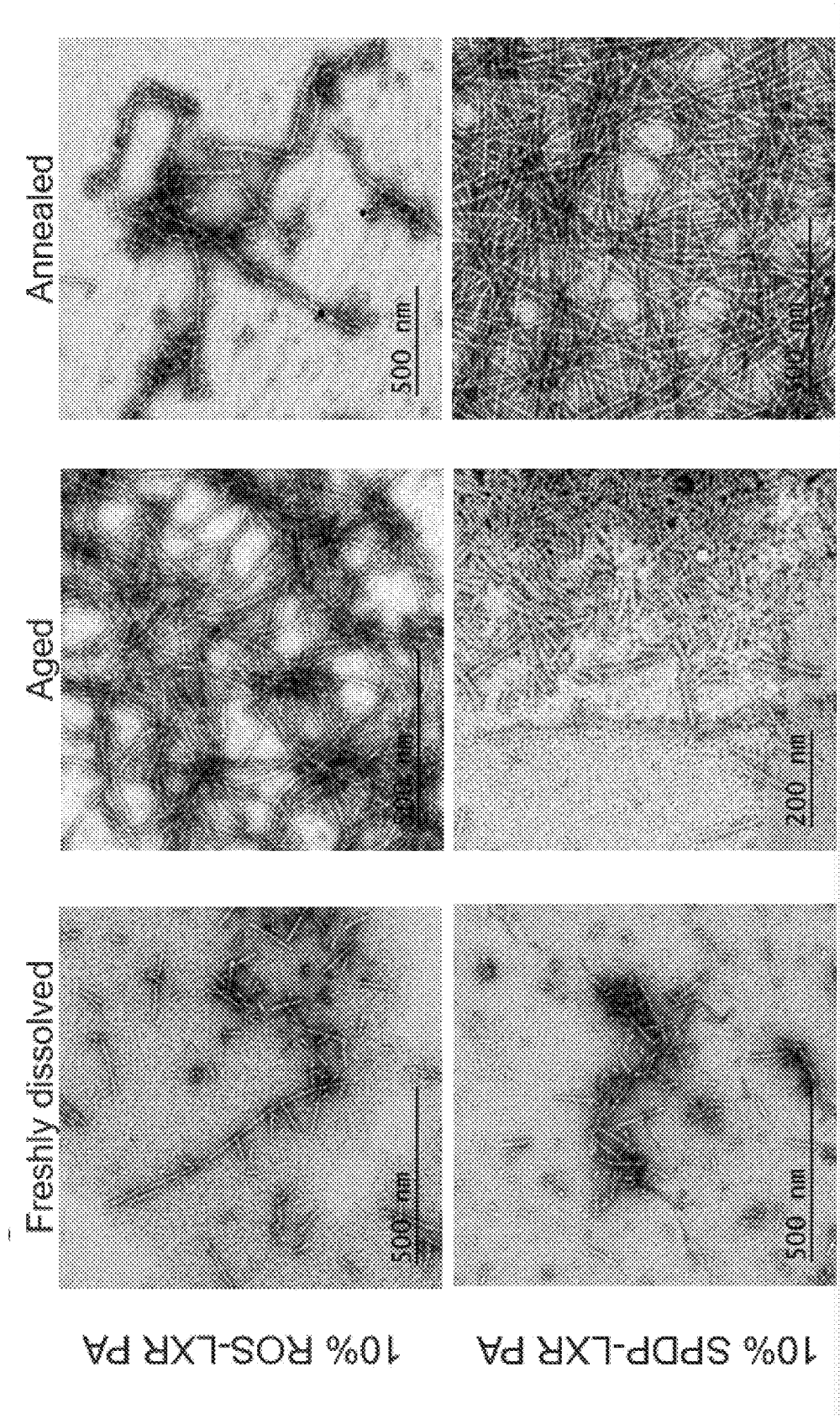
FIG. 34A-34B show conditions for nanofiber formation. Nanofibers were concentrated to 1 mM in PBS, co-assembled with 40 mol % PEG-ApoA1 PA, and 50 mol % E2 PA.
Figure 34B:
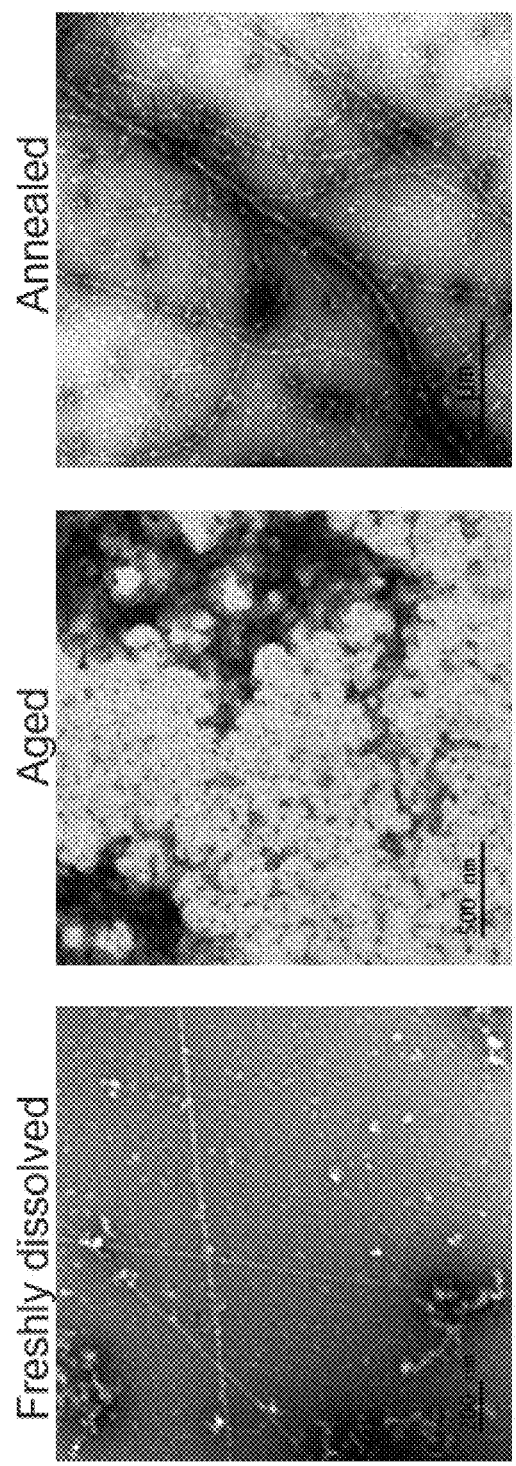

Results are shown in FIG. 34A-34B. Nanofibers were concentrated to 1 mM in PBS, co-assembled with 40 mol % PEG-ApoA1 PA (e.g. ApoA1 targeting PA), and 50 mol %

Figure 35:
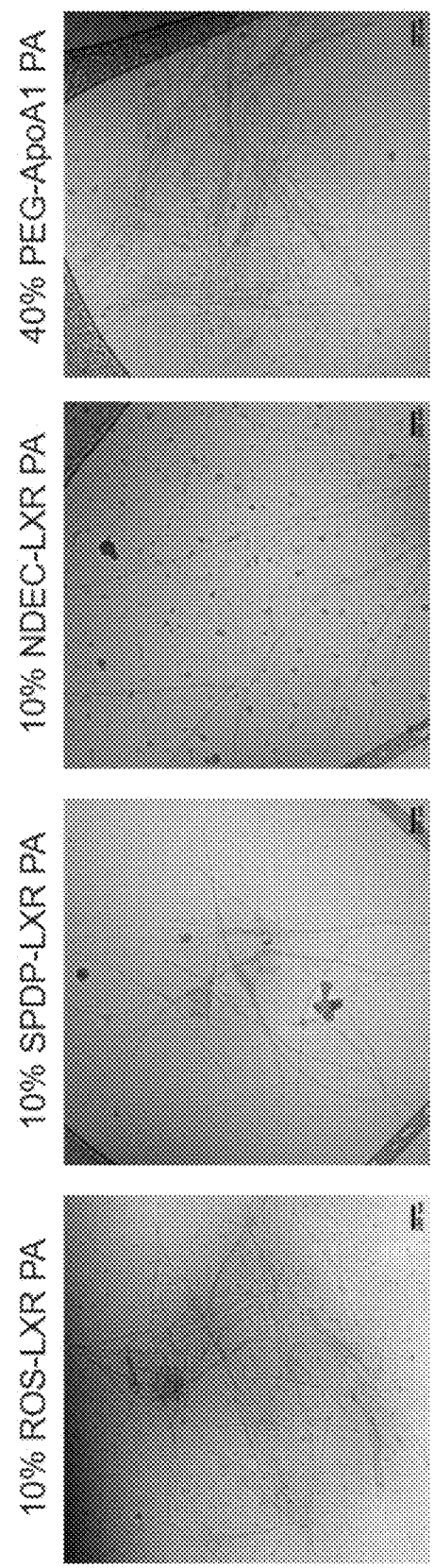
FIG. 35 shows CryoEM images of nanofibers formed in the presence of serum, indicating nanofiber formation is not disrupted by serum proteins.
Figure 36:
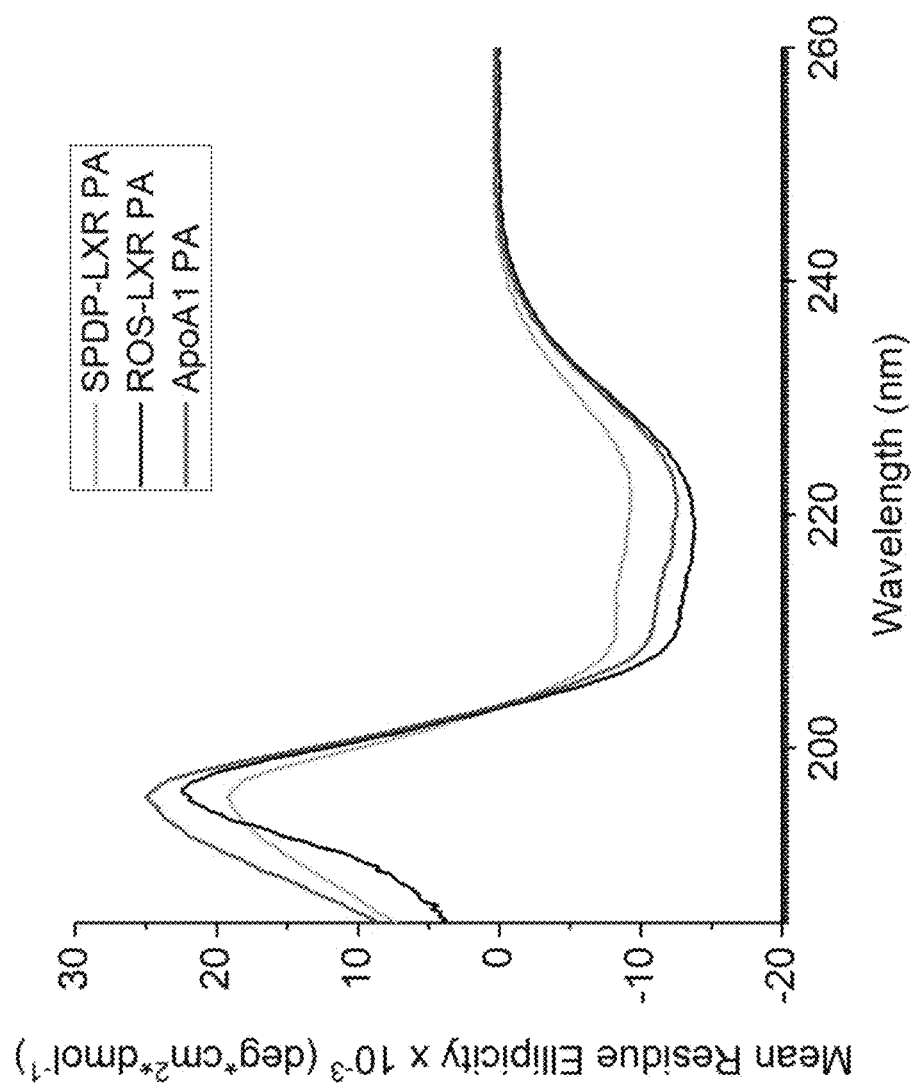
FIG. 36 shows conservation of secondary structure in PA coassemblies. Measurements were taken at 1 mM in 0.1 µM phosphate buffer, 37° C. ApoA1 PA=40 mol % PEG-ApoA1 PA, SPDP-LXR PA=10 mol % PEG-SPDP-LXR PA, ROS-LXR PA=10 mol % PEG-ROS-LXR PA. The data indicate the alpha helical secondary structure of the ApoA1 PA (4F peptide) that is critical for binding to oxidized lipids is not compromised in the SPDP-LXR and ROS-LXR PA coassemblies.
Figure 37A:
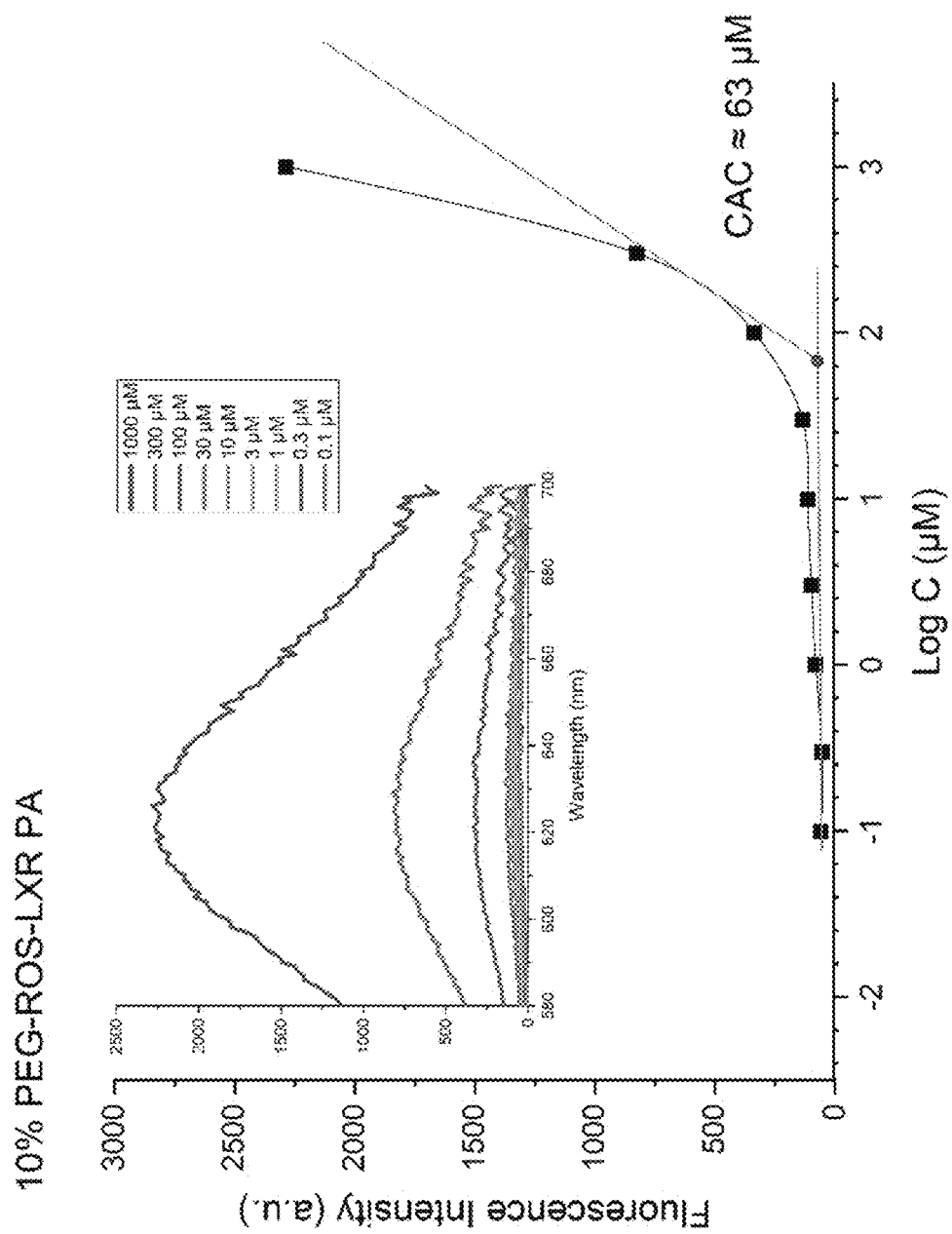
FIG. 37A-37D show the critical aggregation concentration results from the Nile Red Assay.
Figure 37B:
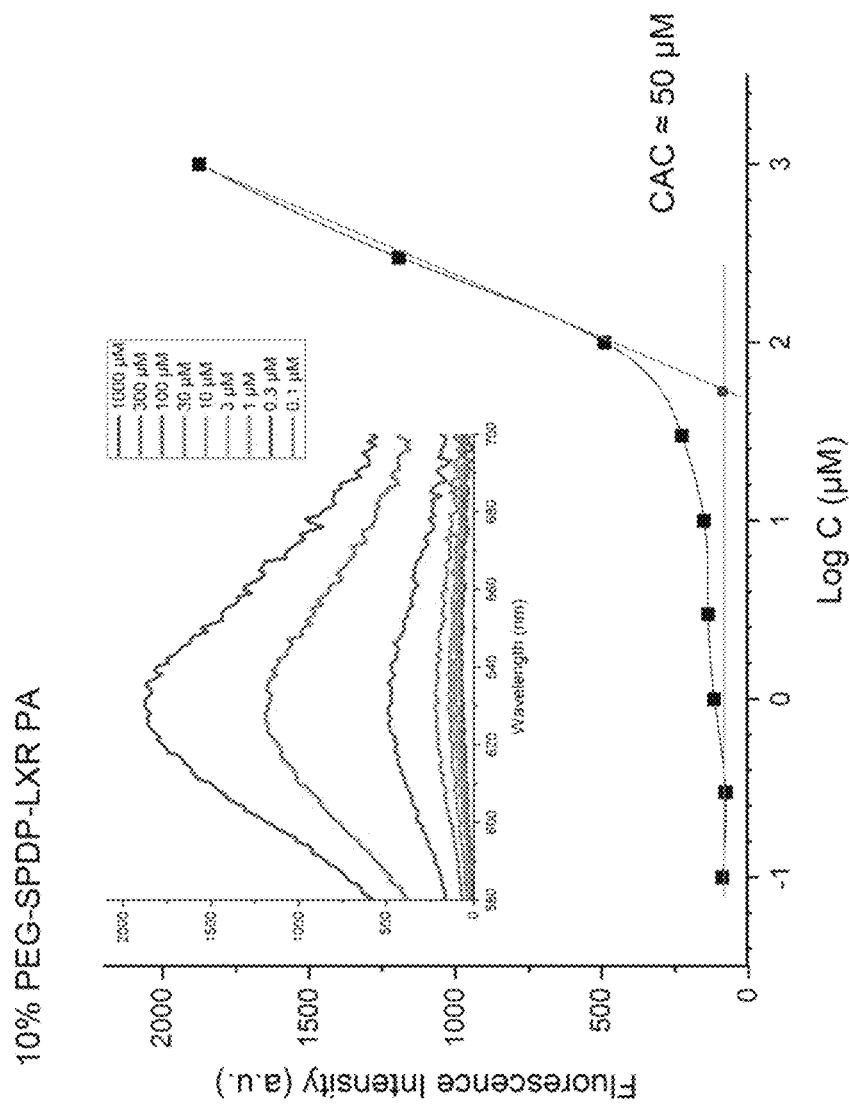
Figure 37C:
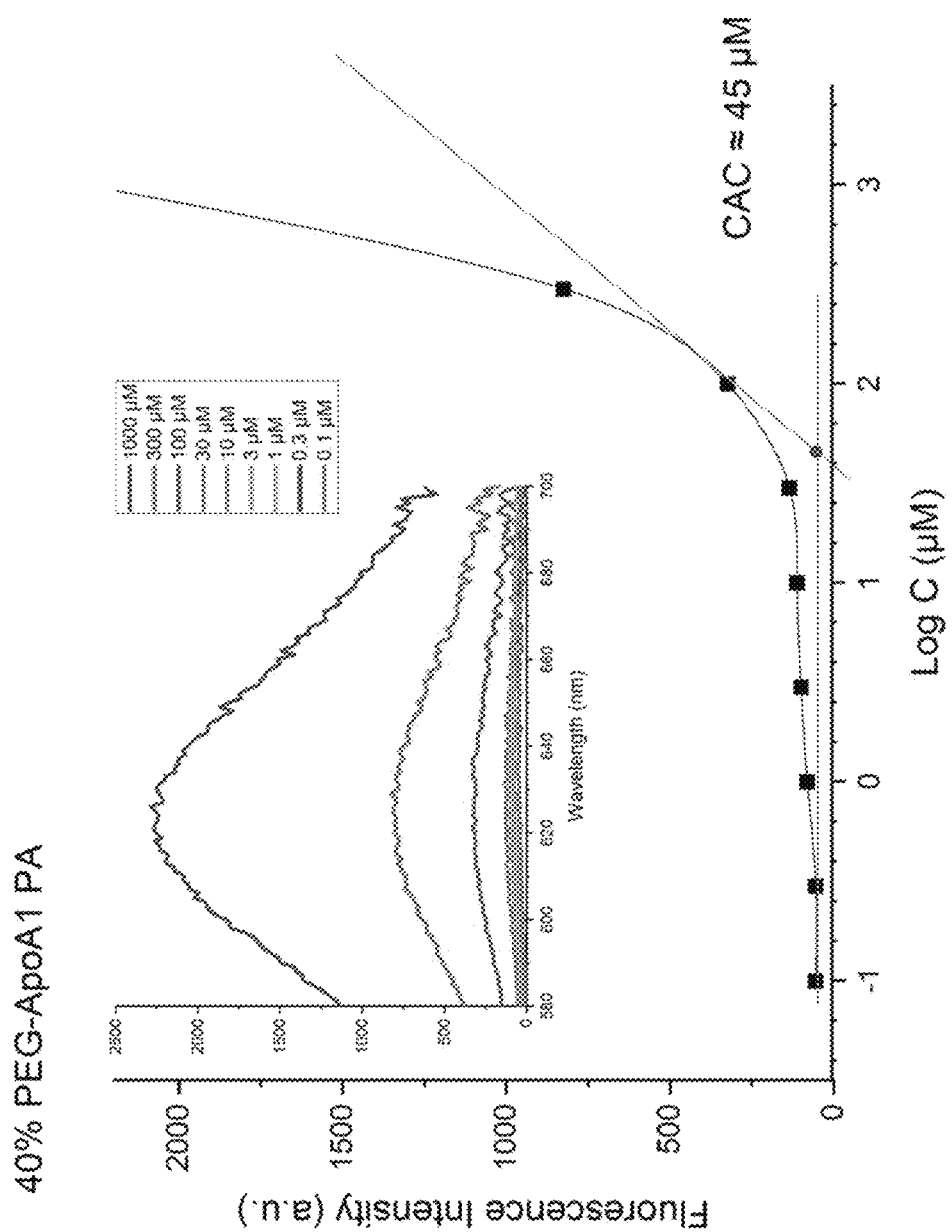
Figure 37D:
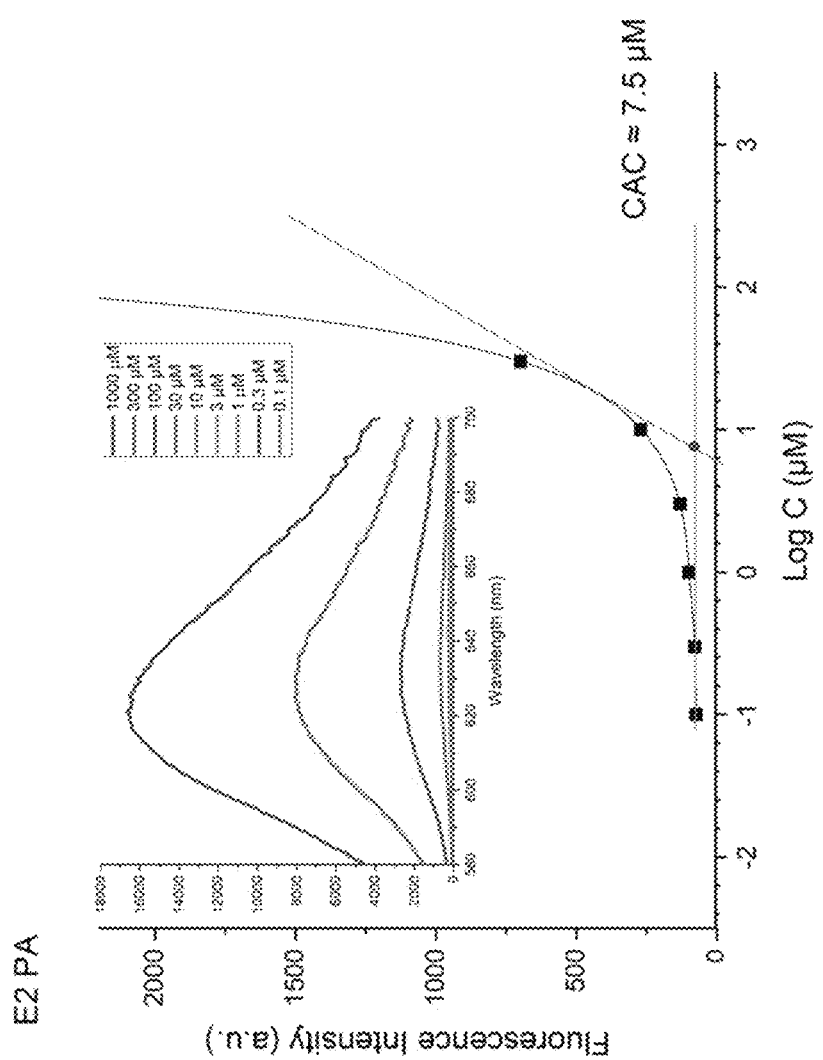

E2 PA (e.g. diluent PA). CryoEM images are shown in FIG. 35. At 10 mol %, the ROS-LXR PAs formed nanofibers upon co-assembly with 40 mol % ApoA1 PAs and 50 mol % diluent PA after 24 hours of aging at 4° C. Similarly, the SPDP-LXR PAs formed the best nanofibers at 10 mol % co-assembly, although annealing at 80° C. for 30 minutes was required. Additionally, the secondary structure of coassemblies was investigated. As shown in FIG. 36, secondary structure was conserved in LXR PA coassemblies (FIG. 36). A Nile Red assay was performed to determine the critical aggregation concentration. Results are shown in FIGS. 37A-37D.

Figure 38A:
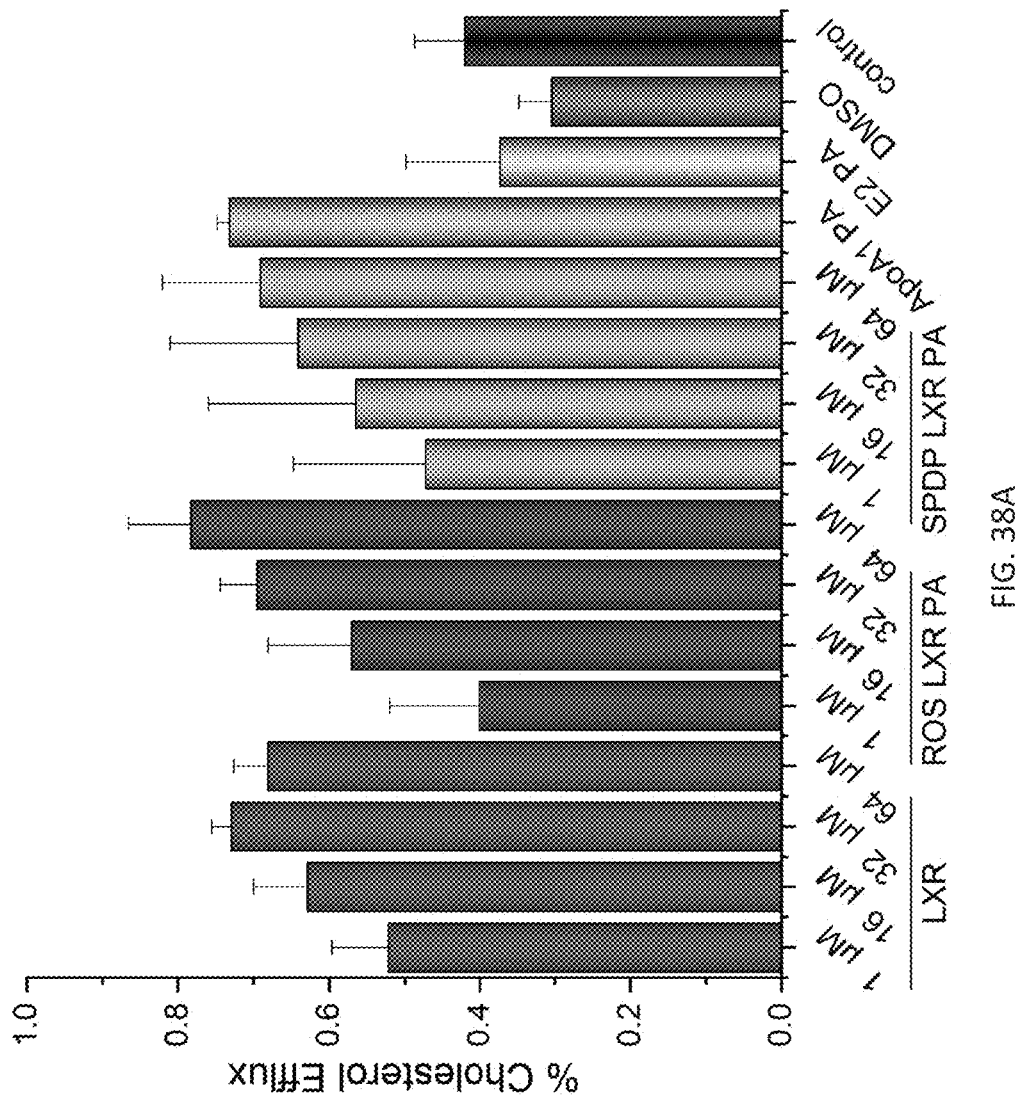
FIG. 38A-38B show the effect of LXR PAs on macrophage cholesterol efflux and viability. ROS-LXR and SPDP-LXR PAs represent 10 mol % co-assemblies, *p<0.05 vs. LXR, ^<0.05 vs. E2 PA, #p<0.05 vs. 1 µM LXR.
Figure 38B:
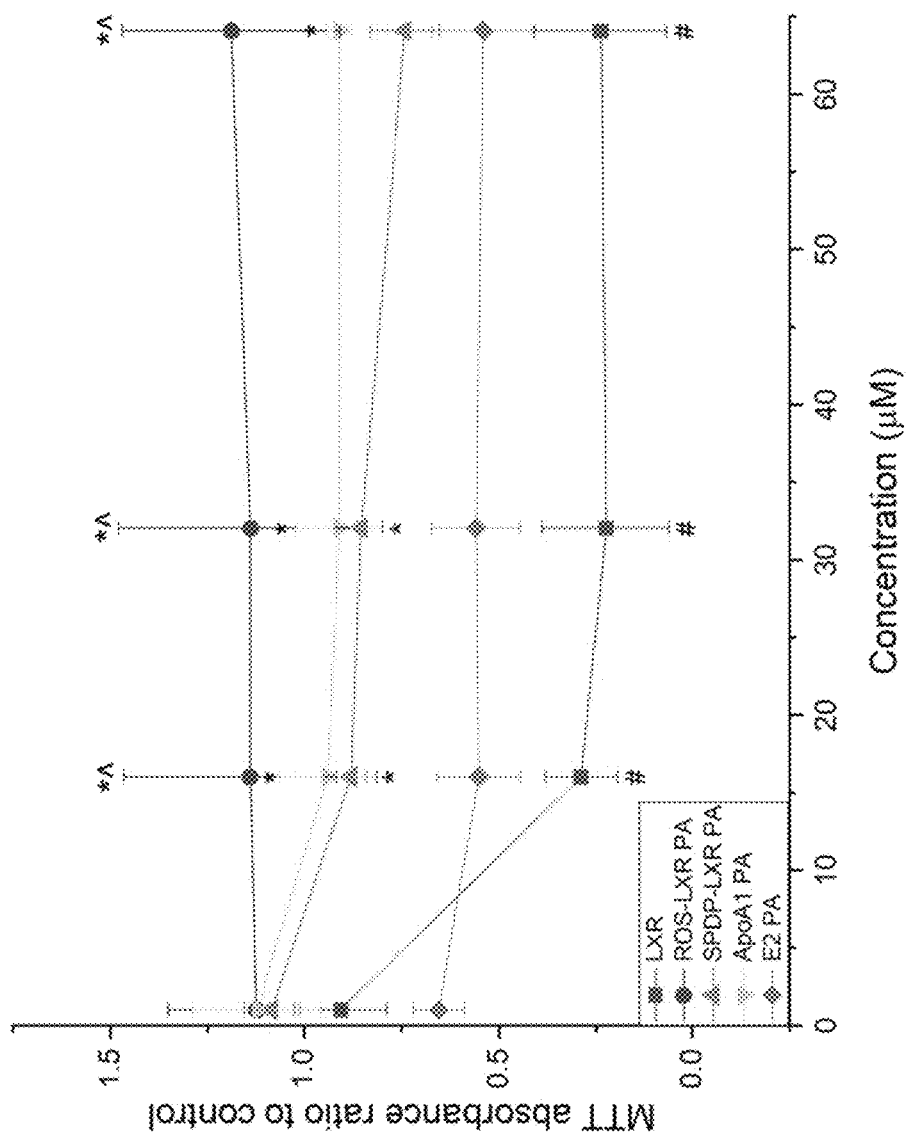
Figure 39A:
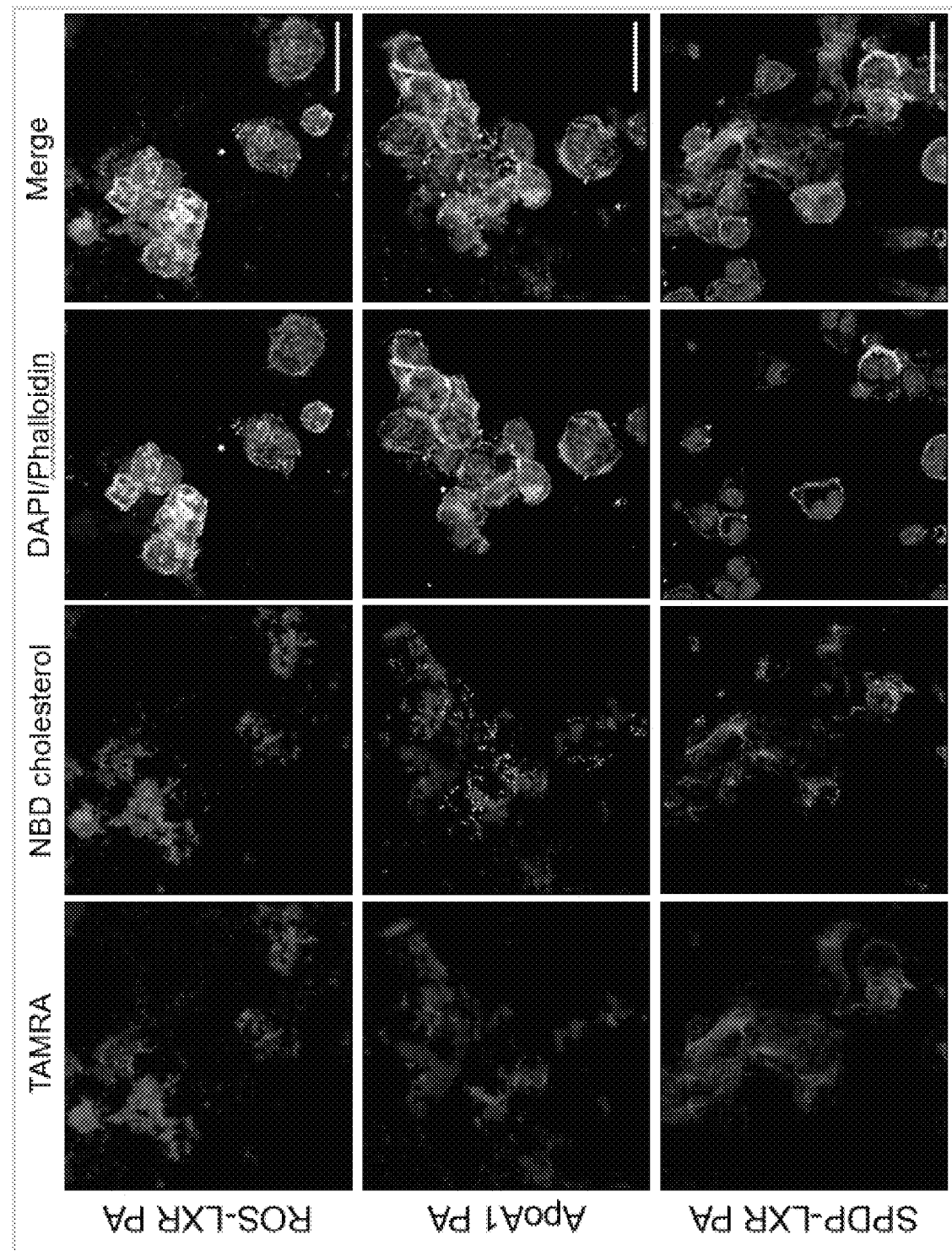
FIG. 39A-39B shows fluorescence microscopy images demonstrating co-localization of various PAs with cholesterol. The cholesterol is labeled with fluorescent dye (green), the PAs are co-assembled with backbone PA containing TAMRA dye (red), the nuclei are stained with DAPI (blue), and the cytoskeleton stained with phalloidin (white). Images are shown from 32 µM LXR or epitope equivalent, Scale bar=25 µm. Results are quantified in FIG. 39C. *p=0.0009, #p<0.02 vs. E2 PA M2 coefficient. M2 is the Manders coefficient that indicates the fraction of all cholesterol pixels that co-localize with PA pixels. These images indicate the ApoA1 PA and LXR PA co-assemblies act as receptors to the effluxed cholesterol.
Figure 39B:
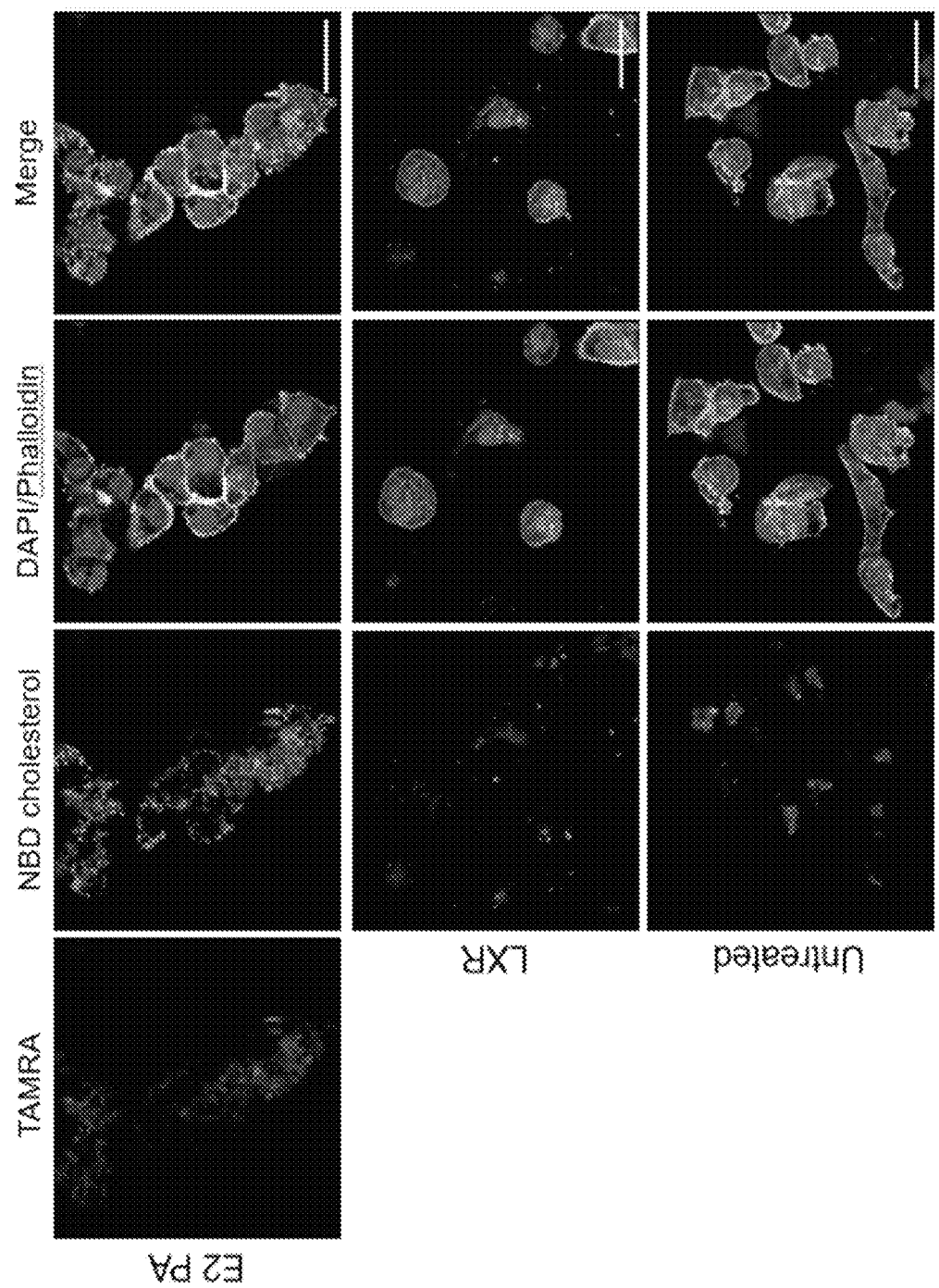
Figure 39C:
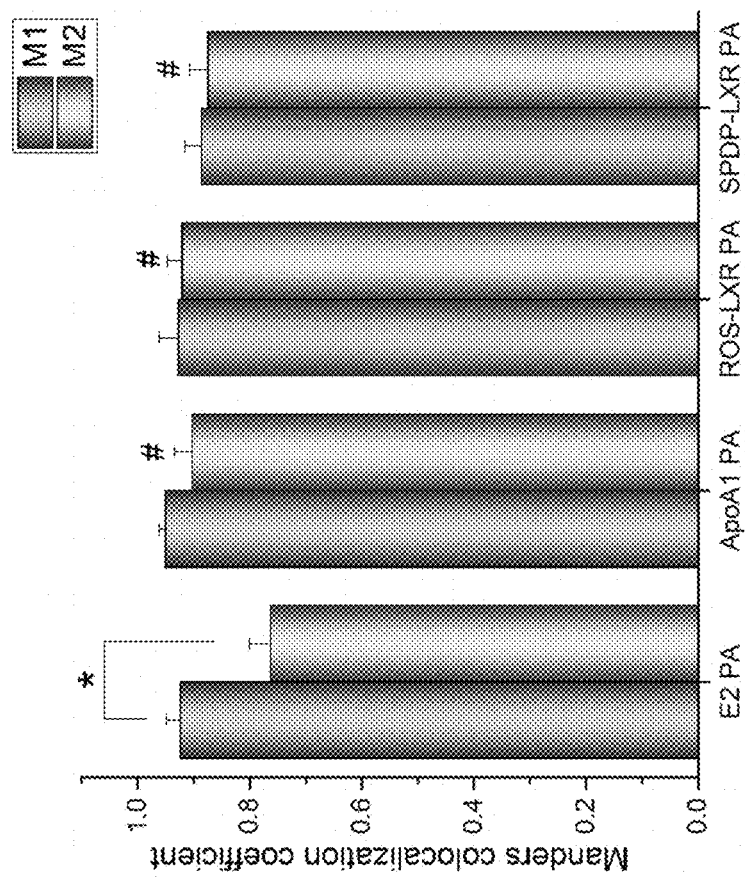
Figure 40:
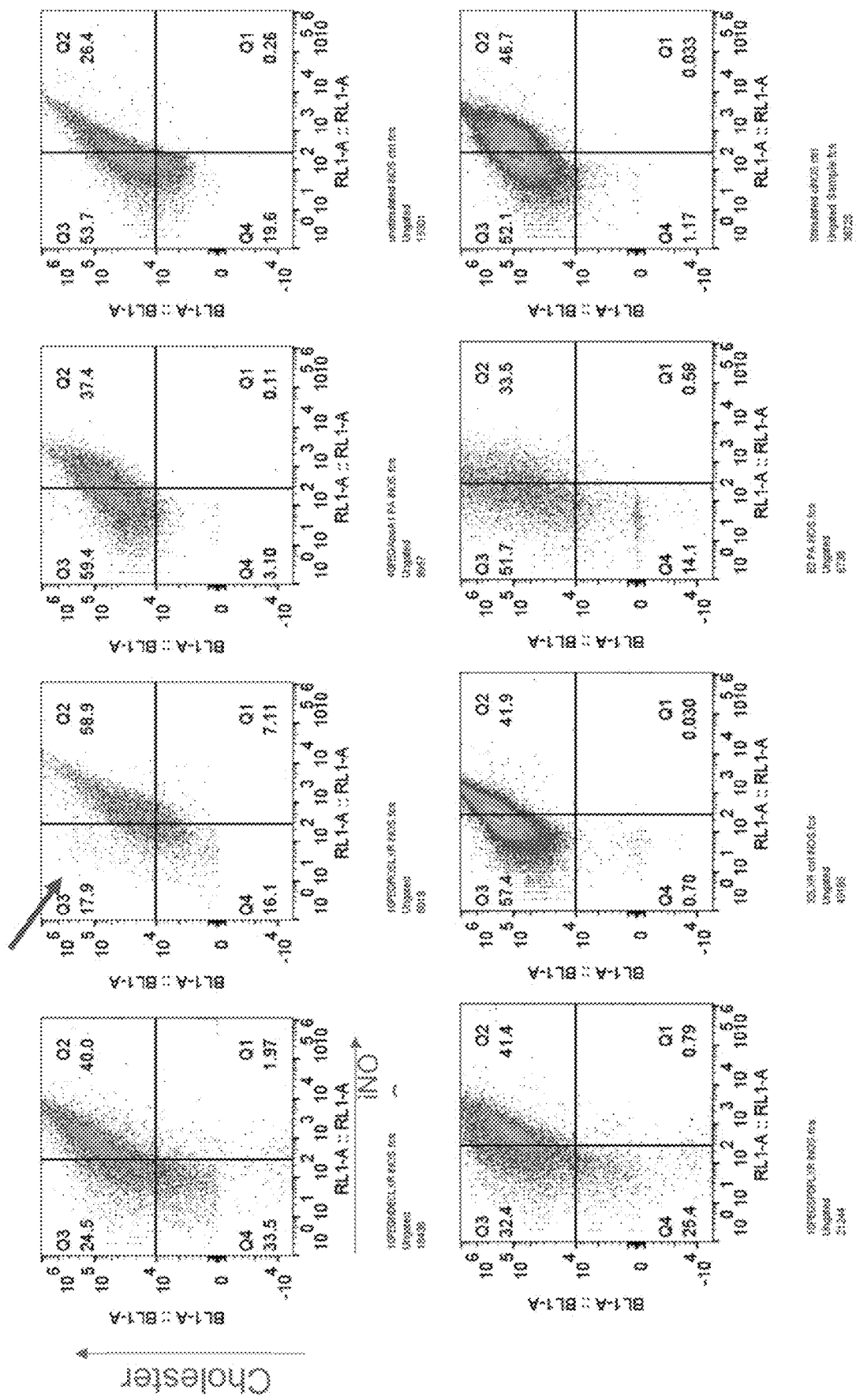
FIG. 40 shows flow cytometry data, demonstrating that 10% ROS-LXR PAs appear to increase cholesterol efflux under inflammatory conditions vs. other PAs and LXR controls.
Figure 41:
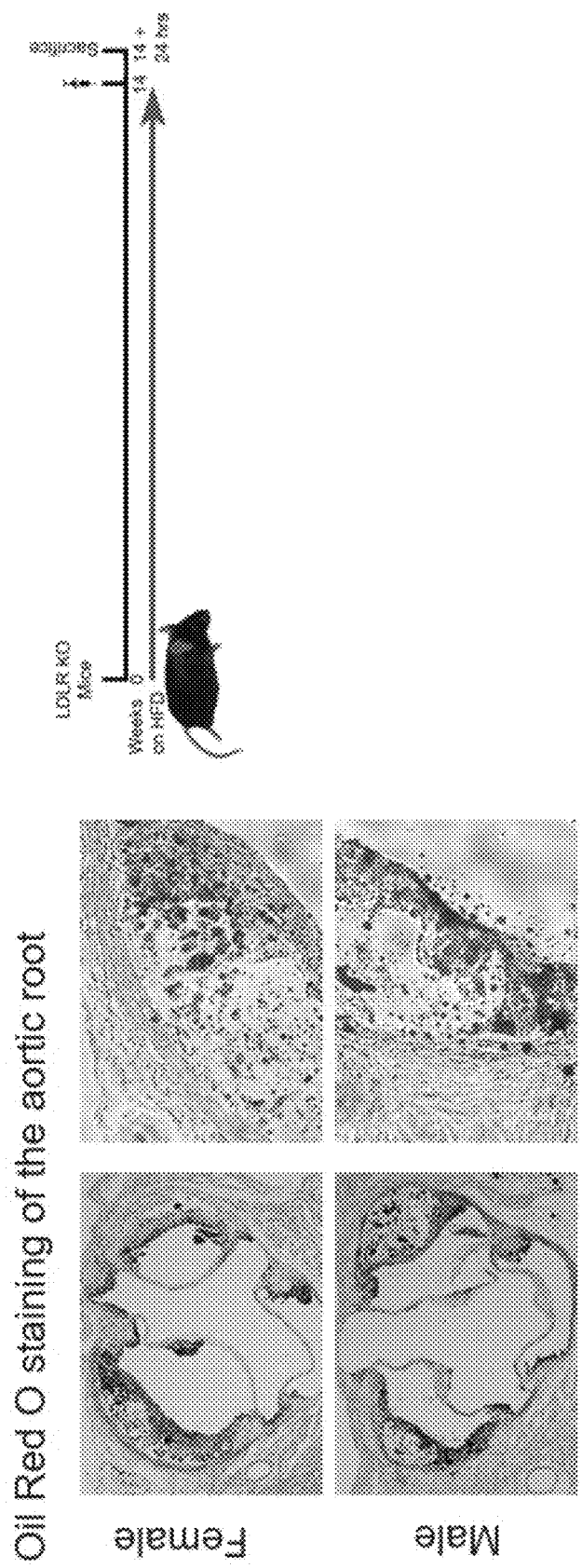
FIG. 41 show the results from in vivo experiments demonstrating LXR agonist targeting to the aortic root following injection with PA nanofibers.
Figure 42:
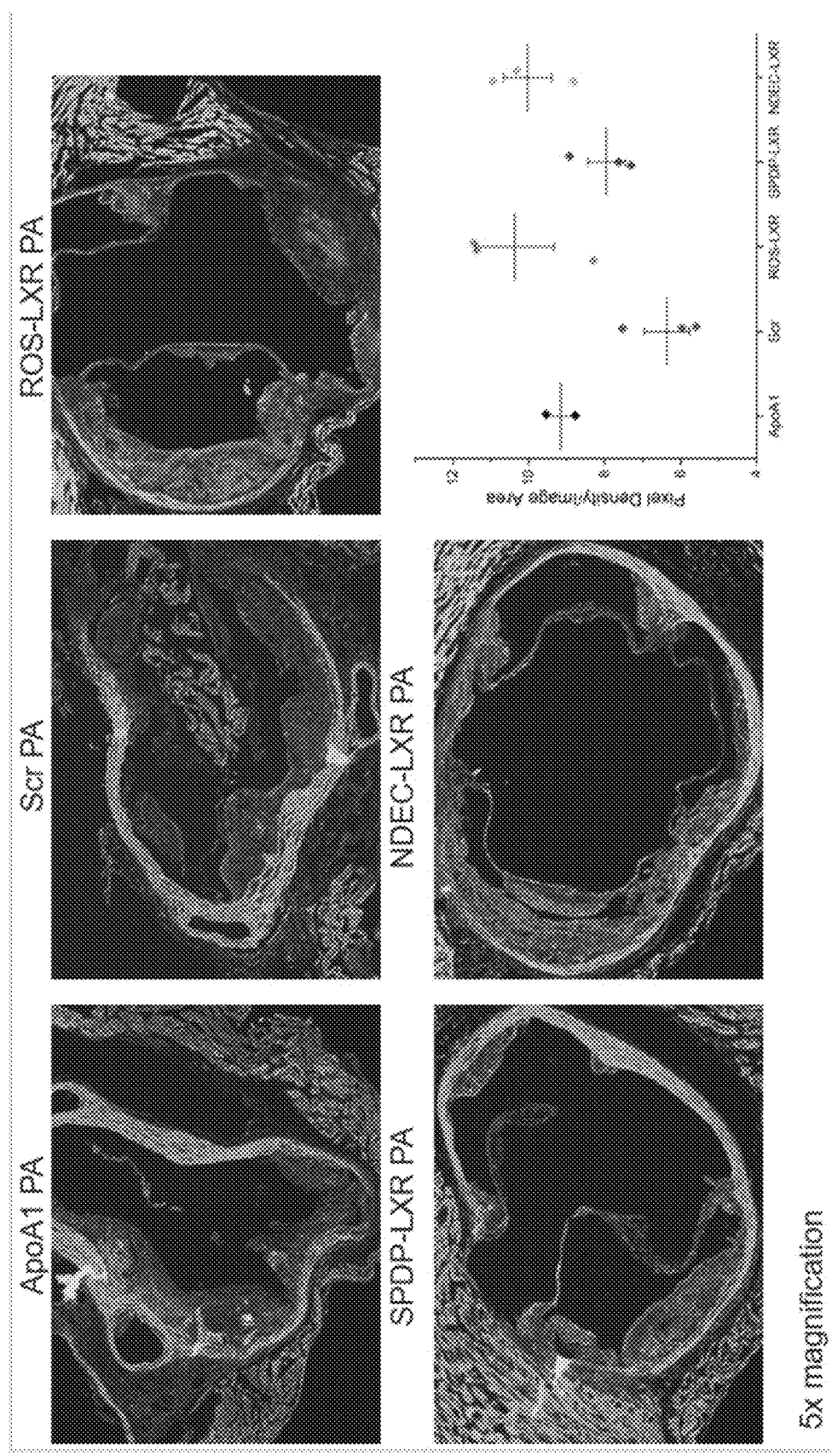
FIG. 42 show microscopy images demonstrating LXR PA targeting to the aortic root at 5× magnification.
Figure 43:
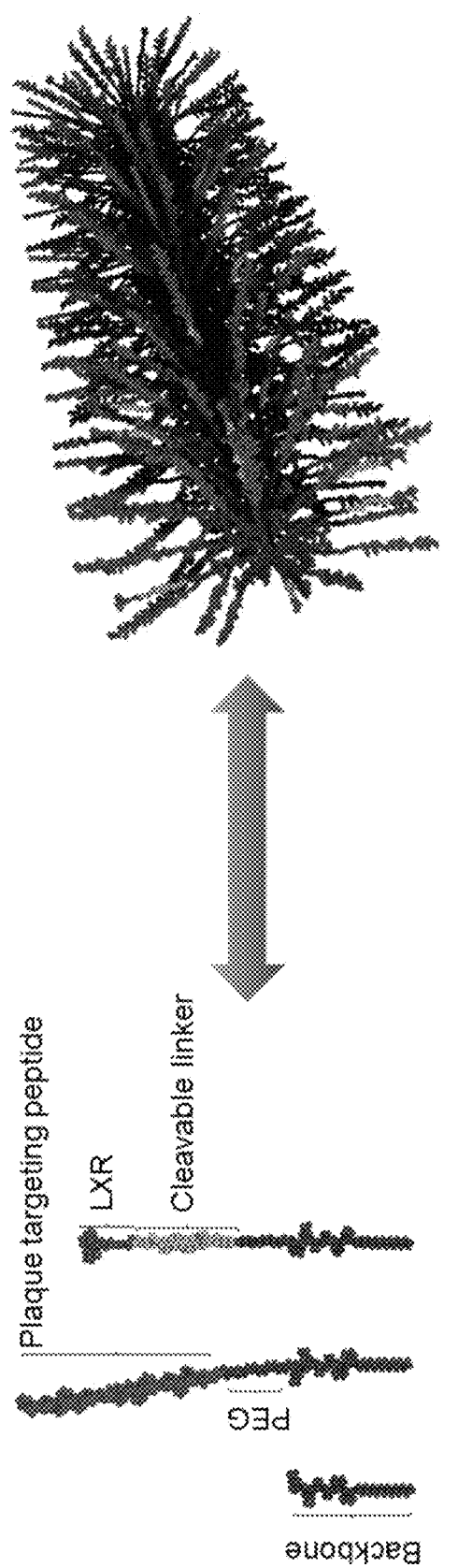
FIG. 43 shows a schematic of nanofibers comprising the ApoA1 targeting peptides and a therapeutic PA (e.g. LXR agonist PA).

Cholesterol Efflux: LXR refers to free LXR agonist, GW3965. ROS LXR PA and SPDP LXR PA represent 10 mol % coassemblies (e.g. nanofibers) with the 40 mol % PEG-ApoA1 PA (e.g. ApoA1 targeting PA), and 50 mol % E2 PA (e.g. diluent PA) as described above. The effect of nanofibers on macrophage cholesterol efflux and viability are shown in FIGS. 38A-38B. Both the ApoA1-ROS-LXR nanofiber (e.g. nanofiber containing an ApoA1 targeting PA and a ROS LXR PA) and ApoA1-SPDP-LXR nanofiber (e.g. nanofiber containing an ApoA1 targeting PA and an SPDP-LXR PA) were able to promote macrophage cholesterol efflux (>70%) to a similar extent as free LXR at concentrations >32 µM LXR (p>0.53) while improving cell viability by at least 3-fold. Colocalization studies were conducted by fluorescence microscopy. Images shown in FIG. 39A-39B demonstrate colocalization of various PAs with cholesterol. Results are quantified in FIG. 39C. The results demonstrate that the ApoA1 derived 4F peptide enables LXR PAs to serve as cholesterol acceptors. As shown in FIG. 40, 10% ROS-LXR PAs appear to increase cholesterol efflux under inflammatory conditions vs. other PAs and LXR controls. FIG. 41 shows in vivo experiments using LXR PAs. LDLR KO mice were used for in-vivo experiments. Mice were kept on a high fat diet for 14 days. Mice were subsequently injected with nanofibers comprising ApoA1 PAs and LXR PAs, and Oil Red O staining was performed to visualize localization of the nanofiber. Results are shown in FIG. 41, demonstrating that the LXR agonist was selectively delivered to the aortic root. Microscopy was also performed to further demonstrate localization of the agonist to the aortic root. Results are shown in FIG. 42.

Conclusion: These results demonstrate tethering LXR agonists to bioresponsive PAs has the potential to increase the safety of LXR agonists to alleviate plaque burden, and supports the use of PA nanofibers for atherosclerosis nanomedicine. The results show that LXR agonists (e.g. GW3965) can be tethered onto PAs and via linkages that cleave in response to ROS and GSH levels found in the atherosclerotic niche. These LXR PAs can be co-assembled with ApoA1 PAs to form nanofibers that promote cholesterol efflux from macrophage foam cells with reduced cytotoxicity vs. free LXR agonist. Moreover, ApoA1-LXR PAs demonstrate potential to target plaque in vivo.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

The invention claimed is:

1. A peptide amphiphile comprising a hydrophobic tail, a structural peptide segment, a charged peptide segment, and a therapeutic agent for the treatment of atherosclerosis in a subject, wherein:
   a) the hydrophobic tail comprises an 8-24 carbon alkyl chain ($C_{8-24}$),
   b) the structural peptide segment comprises $V_2A_2$ (SEQ ID NO: 8),
   c) the charged peptide segment comprises EE, EEE, or EEEE (SEQ ID NO: 11),
   d) the therapeutic agent is attached to the charged peptide segment by a cleavable linker selected from a ROS-sensitive proline linker, a glutathione-sensitive disulfide linker, and an MMP2/9-sensitive linker, and
   e) the therapeutic agent comprises an annexin A1 protein derivative or an LXR agonist, wherein the annexin A1 protein derivative is Ac2-26 or wherein the LXR agonist is selected from hypocholamide, T0901317, GW3965, N,N-dimethyl-3beta-hydroxy-cholenamide (DMHCA), T0901317, 22(R)-hydroxycholesterol and 24(S)-hydroxycholesterol.

2. The peptide amphiphile of claim 1, wherein the therapeutic agent comprises Ac2-26 or GW3965.

3. The peptide amphiphile of claim 1, wherein the cleavable linker comprises GGGPQGIWGQGK (SEQ ID NO: 1), KPPPPK (SEQ ID NO: 17), KPPPPPK (SEQ ID NO: 10), KPPPPPPK (SEQ ID NO: 18), KPPPPPPPK (SEQ ID NO: 19), KPPPPPPPPK (SEQ ID NO: 20), succinimidyl 3-(2-pyridyldithio)propionate (SPDP), or 4-nitrophenyl 2-(2-pyridyldithio)ethyl carbonate (NDEC).

4. The peptide amphiphile of claim 1, wherein the peptide amphiphile comprises $C_{8-24}$-$V_2A_2$(SEQ ID NO: 8)-$E_2$-$KP_5K$ (SEQ ID NO: 10)-AMVSEFLKQAWFIENEEQEYVQTVK (SEQ ID NO: 7), $C_{8-24}$-$V_2A_2$(SEQ ID NO: 8)-$E_2$-GGGPQGIWGQGK (SEQ ID NO: 1)-AMVSEFLKQAWFIENEEQEYVQTVK (SEQ ID NO: 7), $C_{8-24}$-$V_2A_2$(SEQ ID NO: 8)-$E_2$-$KP_5K$ (SEQ ID NO: 10)-GW3965, $C_{8-24}$-$V_2A_2$(SEQ ID NO: 8)-$E_2$-SDSP-GW3965, or $C_{8-24}$-$V_2A_2$(SEQ ID NO: 8)-$E_2$-NDEC-GW3965.

5. A nanofiber comprising the peptide amphiphile of claim 1 and one or more filler peptide amphiphiles, wherein the filler peptide amphiphiles comprise a hydrophobic tail, a structural peptide segment, and a charged peptide segment, and wherein the filler peptide amphiphiles do not comprise a targeting moiety or a therapeutic agent for the treatment of atherosclerosis in a subject.

6. A method of treating atherosclerosis in a subject, comprising providing to the subject the nanofiber of claim 5.

* * * * *

SEQUENCE LISTING

```
<160> NUMBER OF SEQ ID NOS: 20

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Gly Gly Gly Pro Gln Gly Ile Trp Gly Gln Gly Lys
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Asp Trp Phe Lys Ala Phe Tyr Asp Lys Val Ala Glu Lys Phe Lys Glu
1               5                   10                  15

Ala Phe

<210> SEQ ID NO 3
<211> LENGTH: 23
<212> TYPE: PRT
<213> ORGANISM: Artificial Sequence
```

```
<220> FEATURE:
<223> OTHER INFORMATION: Synthetic

<400> SEQUENCE: 3

Cys Gly Val Leu Glu Ser Phe Lys Ala Ser Phe Leu Ser Ala Leu Glu
1               5                   10                  15

Glu Trp Thr Lys Lys Leu Gln
            20

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Asp Trp Leu Lys Ala Phe Tyr Asp Lys Val Ala Glu Lys Leu Lys Glu
1               5                   10                  15

Ala Phe

<210> SEQ ID NO 5
<211> LENGTH: 37
<212> TYPE: PRT
<213> ORGANISM: Artificial Sequence
<220> FEATURE:
<223> OTHER INFORMATION: Synthetic

<400> SEQUENCE: 5

Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
            20                  25                  30

Leu Lys Glu Ala Phe
            35

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Phe Ala Glu Lys Phe Lys Glu Ala Val Lys Asp Tyr Phe Ala Lys Phe
1               5                   10                  15

Trp Asp

<210> SEQ ID NO 7
<211> LENGTH: 25
<212> TYPE: PRT
<213> ORGANISM: Artificial Sequence
<220> FEATURE:
<223> OTHER INFORMATION: Synthetic

<400> SEQUENCE: 7

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 8
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 8

Val Val Ala Ala
1

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Asp Trp Phe Ala Lys Asp Tyr Phe Lys Lys Ala Phe Val Glu Glu Phe
1               5                   10                  15

Ala Lys

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Lys Pro Pro Pro Pro Pro Lys
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic

<400> SEQUENCE: 11

Glu Glu Glu Glu
1

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Val Val Val Ala Ala Ala Glu Glu Glu
1               5

<210> SEQ ID NO 13
<211> LENGTH: 6
<212> TYPE: PRT
<213> ORGANISM: Artificial Sequence
<220> FEATURE:
<223> OTHER INFORMATION: Syntheic

<400> SEQUENCE: 13

Val Val Ala Ala Glu Glu
1               5

<210> SEQ ID NO 14
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 14

Val Val Val Ala Ala Ala
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Ala Ala Val Val
1

<210> SEQ ID NO 16
<211> LENGTH: 6
<212> TYPE: PRT
<213> ORGANISM: Artificial Sequence
<220> FEATURE:
<223> OTHER INFORMATION: Synthetic

<400> SEQUENCE: 16

Ala Ala Ala Val Val Val
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Lys Pro Pro Pro Pro Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Lys Pro Pro Pro Pro Pro Pro Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Lys Pro Pro Pro Pro Pro Pro Pro Lys
1               5

<210> SEQ ID NO 20
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 20

Lys Pro Pro Pro Pro Pro Pro Pro Pro Lys
1               5                   10
```